(12) United States Patent
Heffernan et al.

(10) Patent No.: US 8,734,788 B2
(45) Date of Patent: May 27, 2014

(54) COMPOSITION AND METHOD FOR TREATMENT OF REPERFUSION INJURY AND TISSUE DAMAGE

(75) Inventors: Mark Heffernan, Dublin (IE); Luke O'Neill, Dublin (IE); Peter McGuirk, Dublin (IE); Brian Keogh, Dublin (IE); Christopher Locher, Lexington, MA (US); Dominique De Kleijn, Utrecht (NL); Fatih Arslan, Utrecht (NL); Gerard Pasterkamp, Utrecht (NL)

(73) Assignee: OPSONA Therapeutics Ltd, Dublin (IE)

( * ) Notice: Subject to any disclaimer, the term of this patent is extended or adjusted under 35 U.S.C. 154(b) by 1150 days.

(21) Appl. No.: 12/671,810

(22) PCT Filed: Aug. 4, 2008

(86) PCT No.: PCT/EP2008/060249
§ 371 (c)(1),
(2), (4) Date: Aug. 16, 2011

(87) PCT Pub. No.: WO2009/019260
PCT Pub. Date: Feb. 12, 2009

(65) Prior Publication Data
US 2011/0293601 A1 Dec. 1, 2011
US 2012/0141466 A9 Jun. 7, 2012

Related U.S. Application Data

(60) Provisional application No. 61/038,555, filed on Mar. 21, 2008.

(30) Foreign Application Priority Data

Aug. 3, 2007 (IE) ..................................... 2007/0558

(51) Int. Cl.
*A61K 39/395* (2006.01)
*C07K 16/28* (2006.01)
*A61K 39/00* (2006.01)

(52) U.S. Cl.
CPC ............ *A61K 39/3955* (2013.01); *C07K 16/28* (2013.01); *C07K 16/2803* (2013.01); *C07K 16/2896* (2013.01); *A61K 2039/505* (2013.01); *C07K 2316/96* (2013.01); *C07K 2317/76* (2013.01)
USPC ...................... 424/130.1; 530/387.1

(58) Field of Classification Search
CPC ................. A61K 2039/505; C07K 2316/96; C07K 2317/76
See application file for complete search history.

(56) References Cited

U.S. PATENT DOCUMENTS

2004/0053841 A1 * 3/2004 Tracey et al. .................... 514/12
2005/0113345 A1 * 5/2005 Chow et al. .................... 514/114

FOREIGN PATENT DOCUMENTS

| EP | 1 293 566 A1 | 3/2003 |
| JP | 2005-511020 A | 4/2005 |
| WO | WO-2005/028509 A1 | 3/2005 |
| WO | WO-2005/039504 A2 | 5/2005 |
| WO | WO 2006/077471 A2 | 12/2005 |
| WO | WO-2009/004094 A2 | 1/2009 |

OTHER PUBLICATIONS

Zoppo et al. (Stroke, 2009, 40(8): 2945-2948).*
Van de Werf et al. (Eur Heart J., 2003, 24: 28-66).*
Zambahari et al. (Int. J. Clin. Pract., Mar. 2007, 61: 473-481).*
Jin et al. (Hepatobiliary Pancreat. Dis. Int., Jun. 2007, 6: 284-289).*
Shigeoka et al. (J. Immunol., May 2007, 178: 6252-6258).*
Tang et al. (PNAS, published online Aug. 10, 2007, 104: 13798-13803).*
Zeigler et al. (Biochem. Biophys. Res. Comm., May 2007, 359; 574-579).*
Boyd et al. (Cardiovascular Research, 2006, 72: 384-393).*
Brightbill et al. (Science, 1999, 285: 732-736).*
Flo et al. (J Immunol 2000; 164:2064-2069).*
Leemans et al., Renal-associated TLR2 mediates Ischemia/reperfusion injury in the kidney. J Clin Invest. Oct. 2005;115(10);2894-903.
Meng Antagonistic antibody prevents toll-like receptor 2-driven lethal shock-like syndromes. J Clin Invest. May 2004;113(10):1473-81.
Sakata et al., Toll-like receptor 2 modulates left ventricular function following ischemia-reperfuslon injury. Am J Physiol Heart Circ Physiol. Jan. 2007;292(1):H503-9. Epub Sep. 15, 2006.
Favre et al., Toll-like receptors 2-deficient mice are protected against postischemic coronary endothelial dysfunction. Arterioscler Thromb Vasc Biol. May 2007;27(5):1064-71. Epub Mar. 1, 2007.
Gao et al., p.38 MAPK inhibition reduces myocardial reperfusion injury via inhibition of endothelial adhesion molecule expression and blockade of PMN accumulation. Cardiovasc Res. Feb. 1, 2002;53(2):414-22.
Goshima, Effects of a Neutrophil Elastase Inhibitor and a Dual Inhibitor of Interleukin-1β and Tumor Necrosis Factor-α on Limb Ischemia-Reperfusion Injury in Rats. Jpn J Vasc Surg. 2002;11:7-14.
Bolli et al., *Myocardial Protection at a Crossroads The Need for Translation Into Clinical Therapy* (Circulation Research, Jul. 23, 2004, pp. 125-134).

* cited by examiner

Primary Examiner — Ilia Ouspenski
(74) Attorney, Agent, or Firm — Wolf, Greenfield & Sacks, P.C.

(57) ABSTRACT

The present invention provides compounds and methods for the treatment and prophylaxis of ischemia reperfusion injury. In particular the invention provides compounds which function to suppress Toll-like Receptor 2 biological function or expression.

20 Claims, 24 Drawing Sheets

Figure 1 – Cross section of the heart following administration of a p38 inhibitor (SB239063) as a positive control. IS = white + pale red appearing area. AAR = IS + red area. LV = AAR + blue area

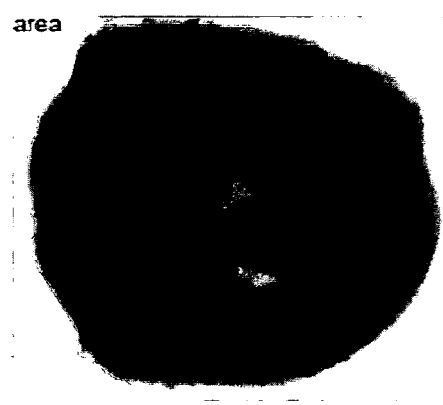
Figure 2 – Cross section of the heart following administration of PBS. IS = white + pale red appearing area. AAR = IS + red area
LV = AAR + blue area

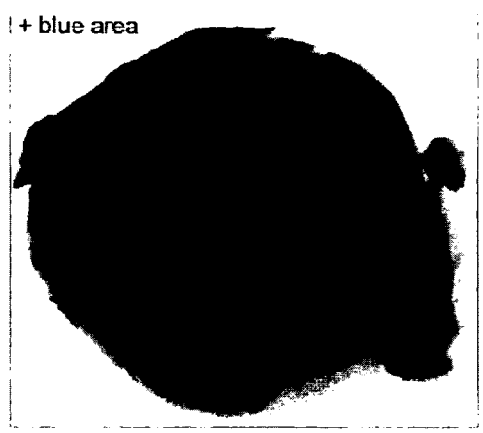
Figure 3 – Cross section of the heart following administration of an antibody of the IgG isotype as a negative control. IS = white + pale red appearing area. AAR = IS + red area. LV = AAR + blue area

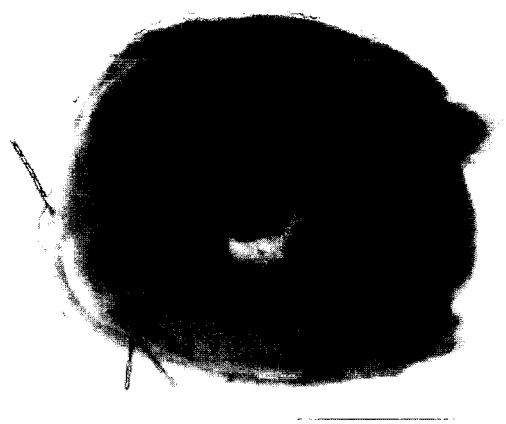
Figure 4 – Cross section of the heart following administration of the experimental OPN301 anti-TLR2 monoclonal antibody. IS = white + pale red appearing area. AAR = IS + red area. LV = AAR + blue area

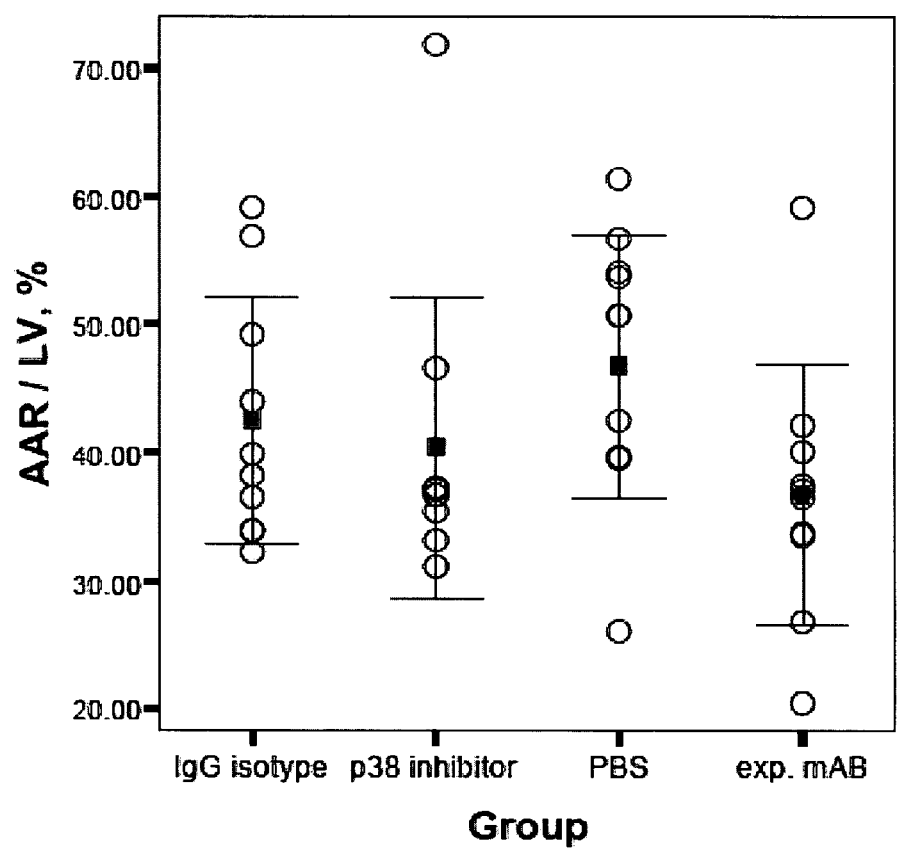
Figure 5 – Area At Risk (AAR) as a percentage of the total left ventricle. Error Bars show mean +/- 1.0 SD

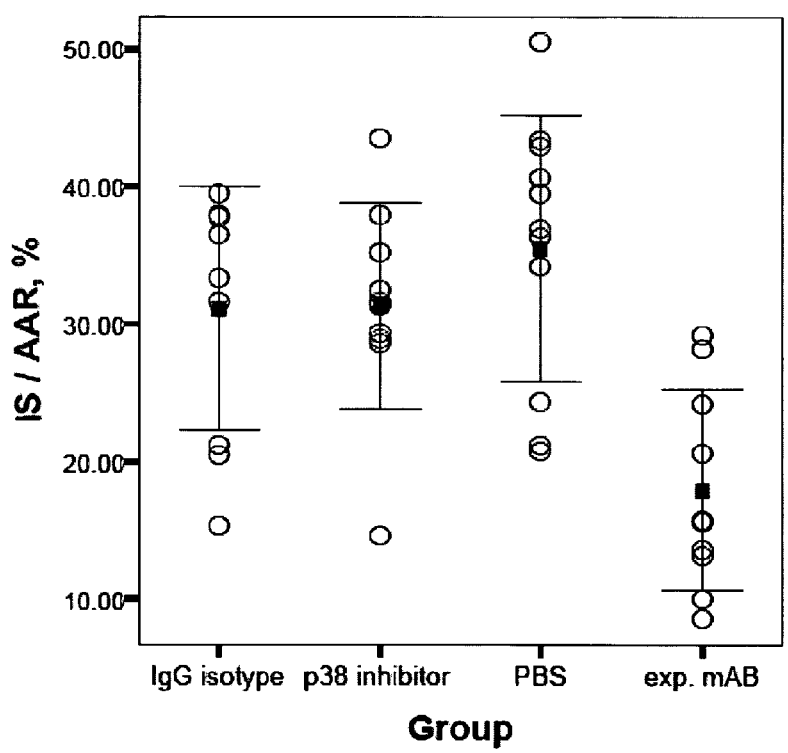
Figure 6 – Infarct size as a percentage of Area At Risk.
Error Bars show mean +/- 1.0 SD

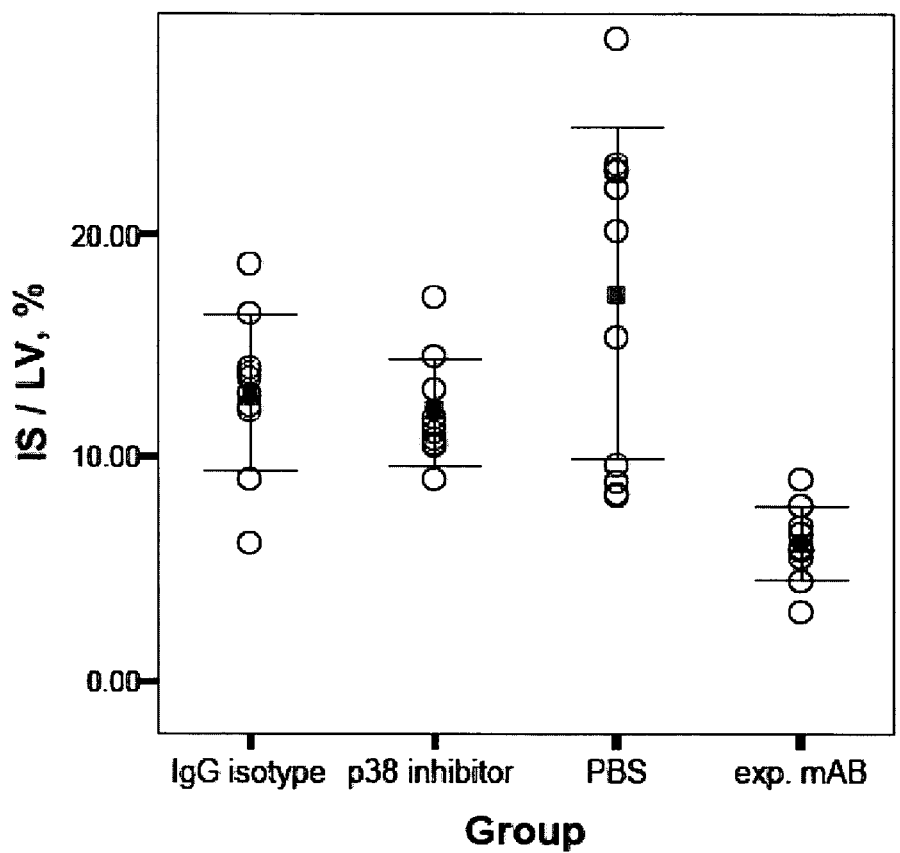
Figure 7 – Infarct size as a percentage of total Left Ventricle (LV). Error Bars show mean +/- 1.0 SD

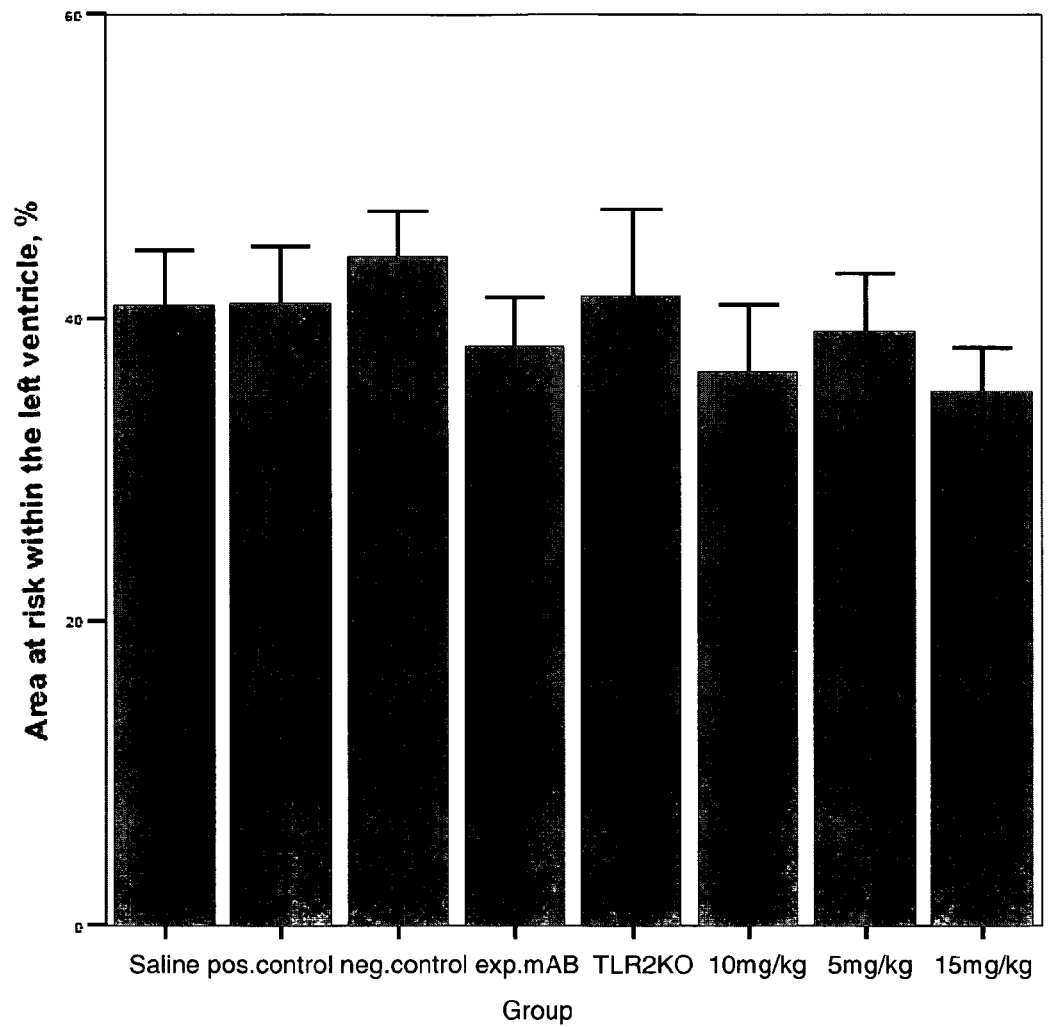
Figure 8 – Area at risk as a percentage of the left ventricle

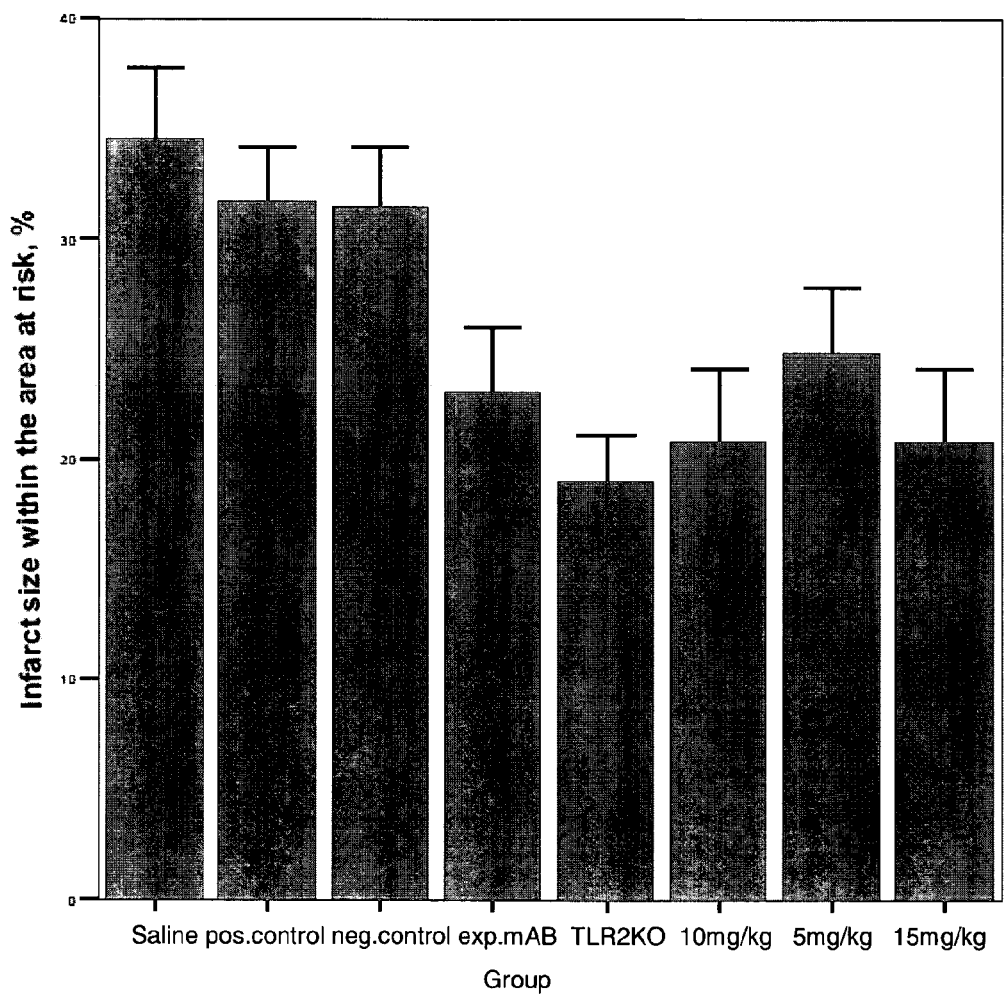
Figure 9 – Infarct size as a percentage of the area at risk

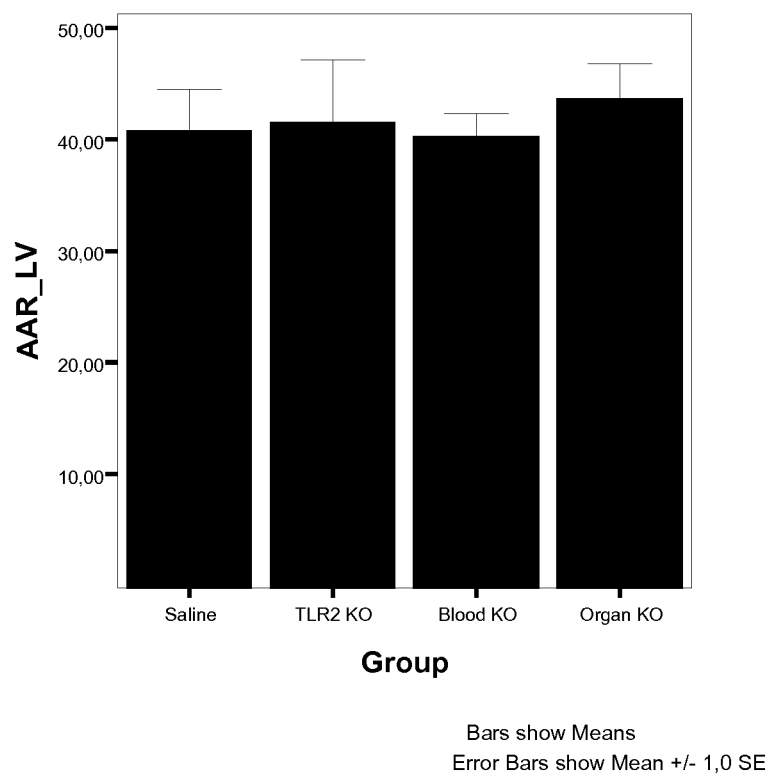
Figure 10. Area at risk as a percentage of the left ventricle

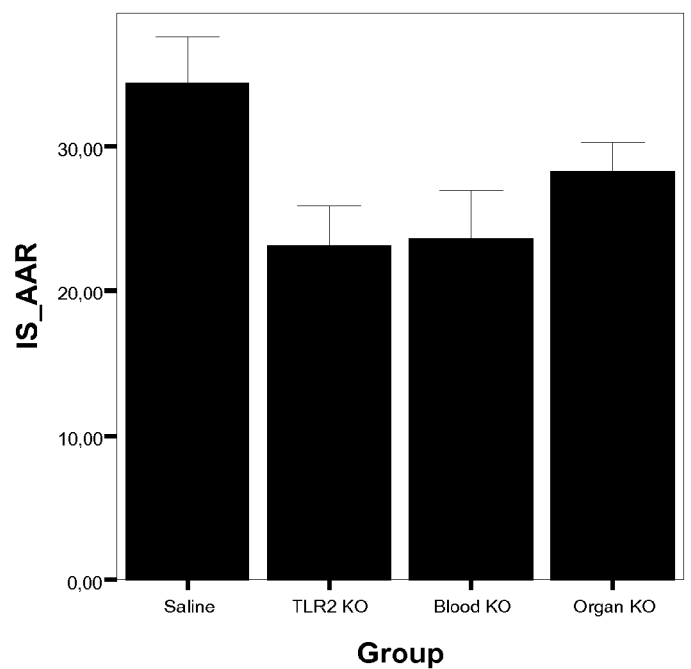
Figure 11. Infarct size as a percentage of the area at risk

```
  1 mphtlwmvwv lgviislske essnqaslsc drngickgss gslnsipsgl teavksldls
 61 nnrityisns dlqrcvnlqa lvltsngint ieedsfsslg slehldlsyn ylsnlssswf
121 kplssltfln llgnpyktlg etslfshltk lqilrvgnmd tftkiqrkdf agltfleele
181 idasdlqsye pkslksiqnv shlilhmkqh illleifvdv tssveclelr dtdldtfhfs
241 elstgetnsl ikkftfrnvk itdeslfqvm kllnqisgll elefddctln gvgnfrasdn
301 drvidpgkve tltirrlhip rfylfydlst lysltervkr itvenskvfl vpcllsqhlk
361 sleyldlsen lmveeylkns acedawpslq tlilrqnhla slektgetll tlknltnidi
421 sknsfhsmpe tcqwpekmky lnlsstrihs vtgcipktle ildvsnnnln lfslnlpqlk
481 elyisrnklm tlpdasllpm llvlkisrna ittfskeqld sfhtlktlea ggnnficsce
541 flsftqeqqa lakvlidwpa nylcdspshv rgqqvqdvrl svsechrtal vsgmccalfl
601 lilltgvlch rfhglwymkm mwawlqakrk prkapsrnic ydafvsyser daywvenlmv
661 qelenfnppf klclhkrdfi pgkwiidnii dsiekshktv fvlsenfvks ewckyeldfs
721 hfrlfeennd aailillepi ekkaipqrfc klrkimntkt ylewpmdeaq regfwvnlra
781 aiks
```

Figure 12. Amino acid sequence of human Toll-like Receptor 2 (SEQ ID NO:1)

```
  1 mlralwlfwi lvaitvlfsk rcsaqeslsc dasgvcdgrs rsftsipsgl taamksldls
 61 fnkityighg dlracanlqv lmlkssrint iegdafyslg slehldlsdn hlsslssswf
121 gplsslkyln lmgnpyqtlg vtslfpnltn lqtlrignve tfseirridf agltslnele
181 ikalslrnyq sqslksirdi hhltlhlses aflleifadi lssvrylelr dtnlarfqfs
241 plpvdevssp mkklafrgsv ltdesfnell kllryilels evefddctln glgdfnpses
301 dvvselgkve tvtirrlhip qfylfydlst vysllekvkr itvenskvfl vpcsfsqhlk
361 slefldlsen lmveeylkns ackgawpslq tlvlsqnhlr smqktgeill tlknltsldi
421 srntfhpmpd scqwpekmrf lnlsstgirv vktcipqtle vldvsnnnld sfslflprlq
481 elyisrnklk tlpdaslfpv llvmkirena vstfskdqlg sfpkletlea gdnhfvcsce
541 llsftmetpa laqilvdwpd sylcdspprl hghrlqdarp svlechqaal vsgvccalll
601 lillvgalch hfhglwylrm mwawlqakrk pkkapcrdvc ydafvsyseq dshwvenlmv
661 qqlensdppf klclhkrdfv pgkwiidnii dsiekshktv fvlsenfvrs ewckyeldfs
721 hfrlfdennd aailvllepi erkaipqrfc klrkimntkt ylewpldegq qevfwvnlrt
781 aiks
```

Figure 13. Amino acid sequence of murine Toll-like Receptor 2 (SEQ ID NO:2)

```
mphtlwmvwvlgviislskeessnqaslscdrngickgssgslnsips
glteavksldlsnnrityisnsdlqrcvnlqalvltsngintieedsf
sslgslehldlsynylsnlssswfkplssltflnllgnpyktlgetsl
fshltklqilrvgnmdtftkiqrkdfagltfleeleidasdlqsyepk
slksiqnvshlilhmkqhillleifvdtssveclelrdtdldtfhfs
elstgetnslikkftfrnvkitdeslfqvmkllnqisgllelefddct
lngvgnfrasdndrvidpgkvetltirrlhiprfylfydlstlyslte
rvkritvenskvflvpcllsqhlksleyldlsenlmveeylknsaced
awpslqtlilrqnhlaslektgetlltlknltnidisknsfhsmpetc
qwpekmkylnlsstrihsvtgcipktleildvsnnnlnlfslnlpqlk
elyisrnklmtlpdasllpmllvlkisrnaittfskeqldsfhtlktl
eaggnnficsceflsftqeqqalakvlidwpanylcdspshvrgqqvq
dvrlsvsech
```

Figure 14. Extracellular domain of human TLR2 (SEQ ID NO:3)

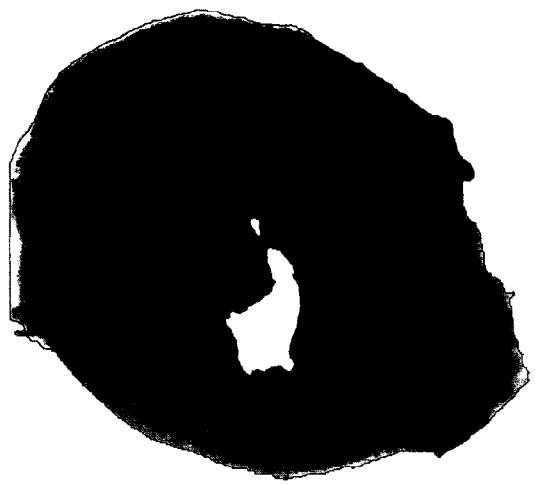
Figure 15 – Cross section of the heart following administration of a p38 inhibitor (SB239063) as a positive control

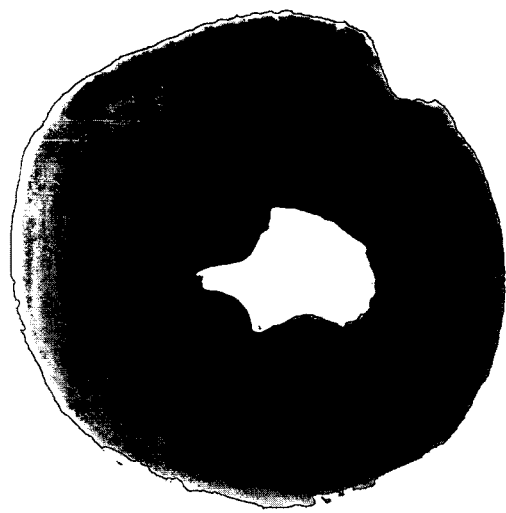
Figure 16 – Cross section of the heart following administration of PBS

Figure 17 – Cross section of the heart following administration of an antibody of the IgG isotype as a negative control

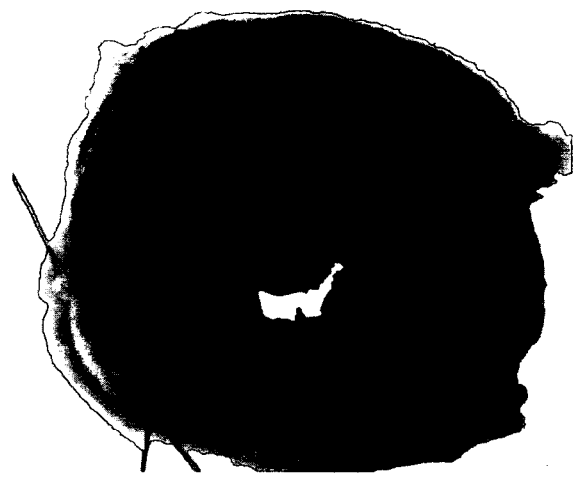
Figure 18 – Cross section of the heart following administration of the experimental OPN301 anti-TLR2 monoclonal antibody

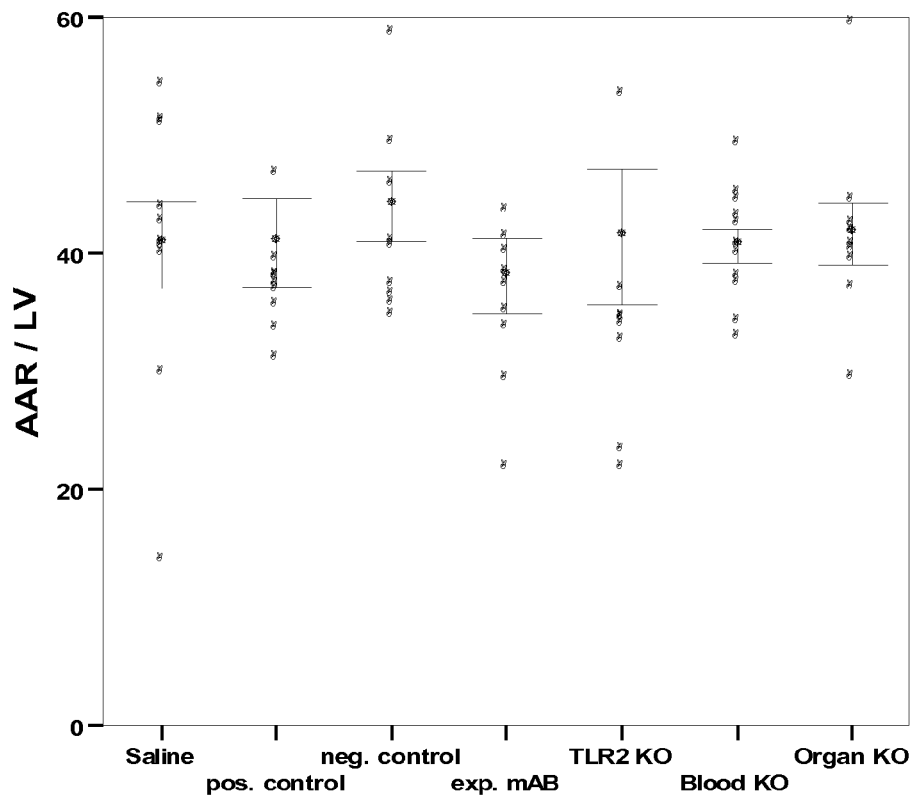
Pos. control=p38 inhibitor; neg. control=IgG isotype; exp. mAB=OPN-301
Error bars show mean +/- 1.0 SE
Figure 19 – Area At Risk (AAR) as a percentage of the total left ventricle. Error Bars show mean +/- 1.0 SD

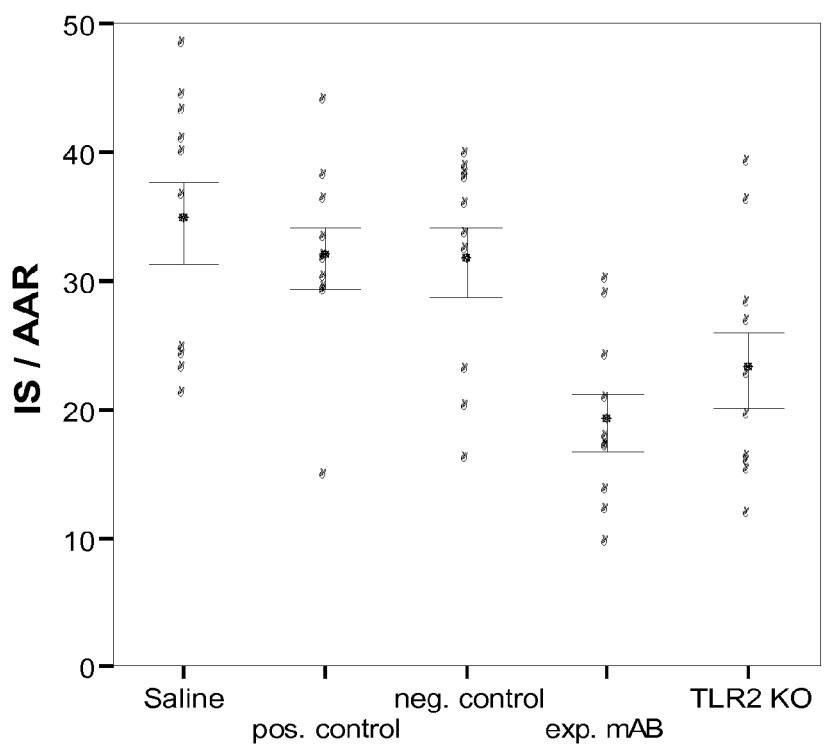
Figure 20 – Infarct size as a percentage of Area At Risk.
Error Bars show mean +/- 1.0 SD

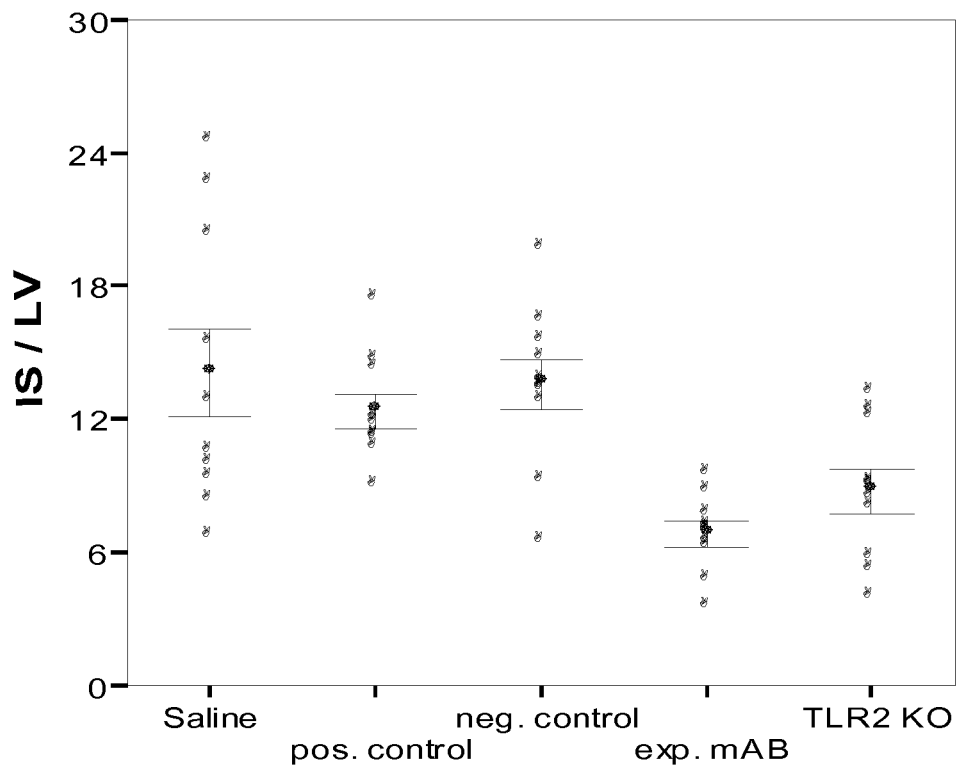
Figure 21 – Infarct size as a percentage of total Left Ventricle (LV). Error Bars show mean +/- 1.0 SD

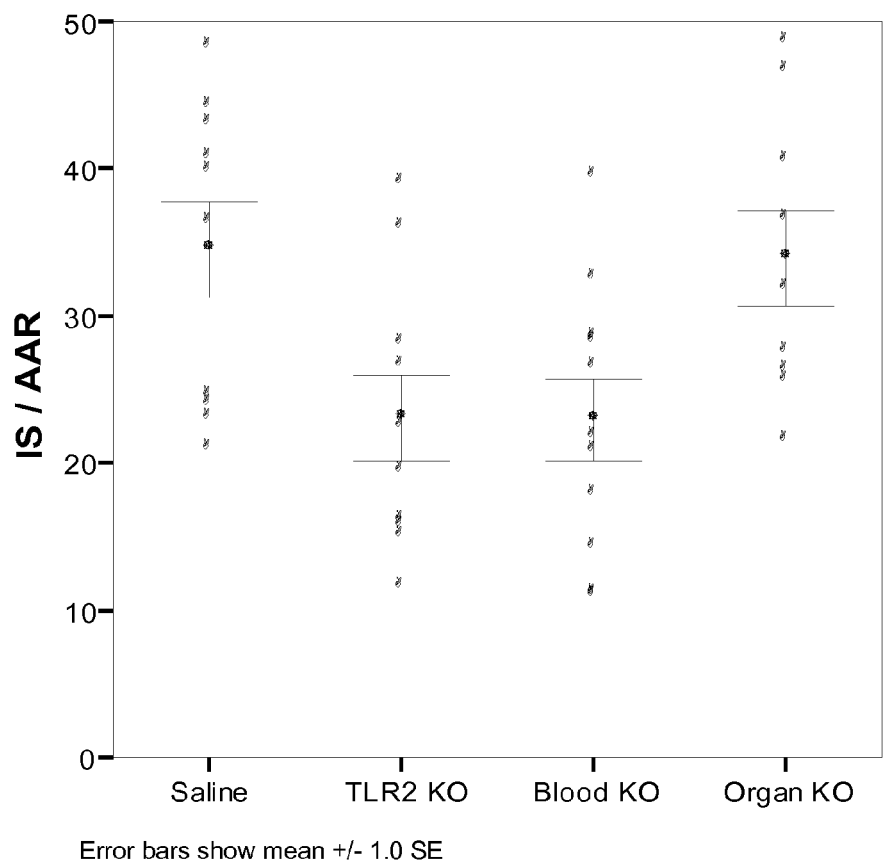
Figure 22. Infarct size as a percentage of the area at risk in chimeric mice

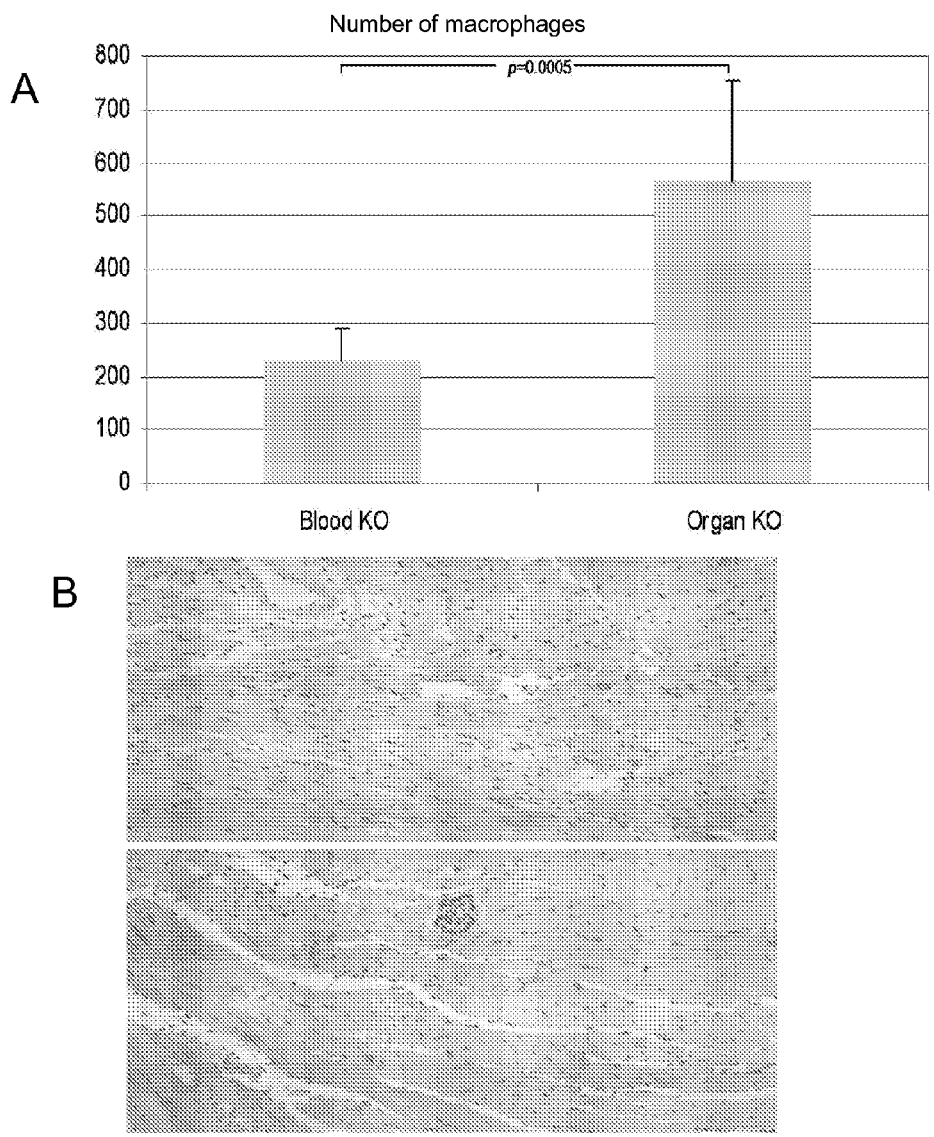
Figure 23: Number of macrophages in heart section from Blood KO and Organ KO chimeric mice after 30 minutes ischaemia followed by 24 hours of reperfusion

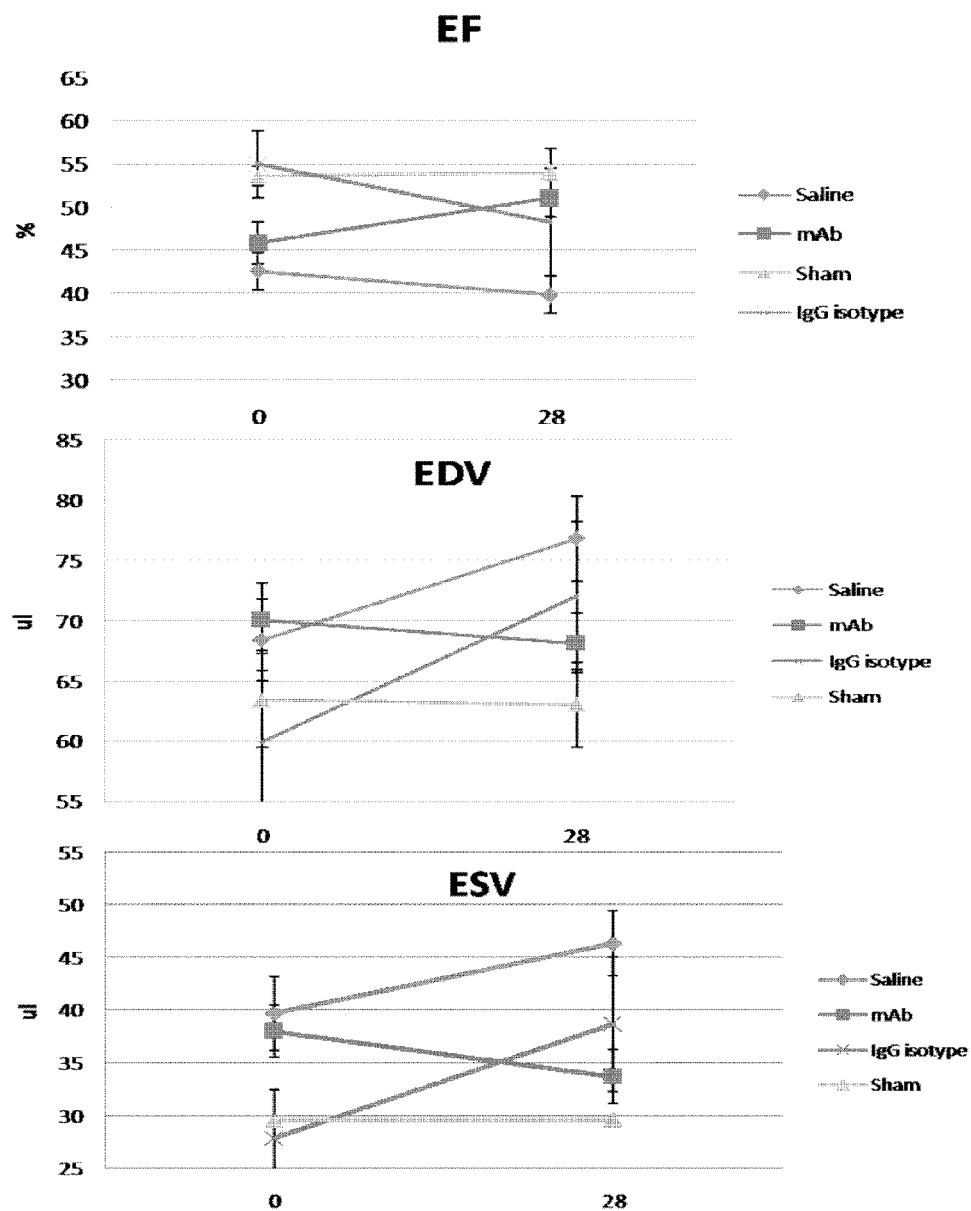
Figure 24 : Cardiac function and geometry at baseline (t=0) and post-infarction (t=28)

COMPOSITION AND METHOD FOR TREATMENT OF REPERFUSION INJURY AND TISSUE DAMAGE

CROSS REFERENCE TO RELATED APPLICATIONS

This application is a national stage filing under 35 U.S.C. §371 of international application PCT/EP2008/060249, filed Aug. 4, 2008, which was published under PCT Article 21(2) in English, and which claims the benefit under 35 USC §119 (e) of U.S. Provisional Application No. 61/038,555, filed Mar. 21, 2008, and also Ireland Application No. 2007/0558, filed Aug. 3, 2007, the disclosures of all of which are incorporated by reference herein in their entirety.

FIELD OF THE INVENTION

The present invention relates to a method for the treatment and prevention of ischemia reperfusion injury. In particular, the present invention identifies Toll-like Receptor 2 as a novel target for use in treating or preventing ischemia reperfusion injury. Blocking the functional activity of Toll-like Receptor 2 by an antagonistic agent downregulates the inflammatory processes which are associated with reperfusion injury, this resulting in an improved therapeutic outcome for the subject to whom the Toll-like Receptor 2 antagonistic agent is administered.

BACKGROUND TO THE INVENTION

Heart failure is the pathophysiological state in which the heart is unable to pump blood at a sufficient rate through the circulation system of the body. This condition can result in congestive heart failure, a condition which arises when excess fluid accumulates due to the reduced pumping function of the heart. Myocardial infarction occurs when an interruption of the blood supply to the tissues of the heart causes necrosis of the region of tissue where blood supply has been deprived.

Ischemia is caused when an organ or part of the body fails to receive a sufficient blood supply. An organ that is deprived of an adequate blood supply is said to be hypoxic. Reperfusion occurs when blood flow recommences to an organ following temporary deprivation.

Reperfusion injury relates to damage which occurs to a tissue or an organ upon the return of the blood supply to a tissue following a period of ischemia. The absence of oxygen and nutrients during the period of ischemia results in a period of inflammation and oxidative damage when circulation returns. Examples of ischemia reperfusion injury include hypoxia, stroke, heart attack, chronic kidney failure or organ transplantation.

The etiology of reperfusion injury is multifactorial, although it is strongly associated with the pro-inflammatory immune response. Specifically, the return of blood flow to an area previously deprived of blood flow can result in the onset of a number of pro-inflammatory processes such as leukocyte adhesion and infiltration, free radical release and cytokine production. Furthermore, damage to the membranes of cells in areas which have undergone ischemia may result in the release of further free radicals. Programmed cell death (apoptosis) may also occur, while the migration of leukocytes to the area of ischemia may cause a blockage in capillaries, this resulting in a restriction of blood flow and an associated risk of further ischemia. Accordingly, restoration of blood flow following a period of ischemia can actually be more damaging than the ischemic event itself.

Therapeutic strategies for the treatment of myocardial infarction, whether pharmacological or mechanical, aim to open, or keep open, the occluded coronary artery in order to restore blood flow and perfusion of the myocardial tissue. Early restoration of blood flow in the infarct related artery and reperfusion of endangered viable myocardium improves clinical outcome. Paradoxically however, reperfusion itself results in necrosis and acceleration of apoptosis in cardiomyocytes, referred to as ischemia/reperfusion (I/R) injury. Since complications due to loss of viable myocardial tissue are still common after myocardial infarction, reperfusion alone seems insufficient to save endangered myocardium.

Reperfusion activates an inflammatory response mediated by the innate immune system. This activation of the innate immune system also leads to death of cardiomyocytes due to the release of pro-inflammatory cytokines and hazardous cell-to-cell interactions between neutrophils and cardiomyocytes. The intracellular Nuclear Factor-kappa B (NF-kB) signaling pathway mediates the transcription of pro-inflammatory genes in myocardial ischemia/reperfusion (I/R) injury. Further, the reintroduction of oxygen results in a greater production of damaging free radicals, an increase in pro-inflammatory mediators, and the associated onset of necrosis. The severity of reperfusion may vary due to a number of factors such as duration of ischemia, severity of ischemia and speed of reperfusion.

Toll-like Receptors (TLRs) form a family of pattern recognition receptors which have a key role in activating the innate immune response. Eleven Toll-like Receptors have been identified in humans to date. The members of the Toll-like Receptor family are highly conserved, with most mammalian species having between 10 to 15 Toll-like Receptors. Each Toll-like Receptor recognises specific pathogen-associated molecular signatures. Toll-like Receptor 2 (TLR2, CD282, TLR-2) can be activated by peptidoglycan, lipoproteins and lipoteichoic acid.

Studies to date have not fully elucidated the complex interplay of regulatory and inflammatory mechanisms which are triggered during ischemia and reperfusion. Furthermore, the nature and variability of ischemic reperfusion injury as expressed in different animal models, different patients and different tissues, has created further obstacles in relation to identifying methods for therapeutic intervention and prevention of ischemia reperfusion.

Following extensive experimentation, the present inventors have surprisingly identified that Toll-like Receptor 2 has an important role in the onset and progression of the innate inflammatory immune which is associated with ischemia reperfusion injury in a tissue or organ which has undergone a period of ischemia. The inventors have identified that compounds which have a binding specificity for Toll-like Receptor 2, and which function as Toll-like Receptor 2 agonists have utility in preventing aberrant pro-inflammatory immune responses which are associated with the development of reperfusion injury. The inventors have therefore identified that a therapeutic approach for the prevention and treatment of ischemia reperfusion injury, mediated by suppressing Toll-like Receptor 2 activation and signalling, would be potentially significant, particularly as the conserved nature of Toll-like Receptor 2 would suggest that such a therapeutic approach would provide a global approach to the treatment of this condition in a wide variety of species, tissues and cell types.

SUMMARY OF THE INVENTION

According to a first aspect of the present invention there is provided a method of reducing one or more biological activities of Toll-like receptor 2 (TLR2) in a TLR2 expressing cell or tissue implicated in ischemia reperfusion injury, comprising:

contacting the cell or tissue with at least one antagonist of TLR2 activity or expression, in an amount sufficient to reduce one or more biological activities of TLR2 in the cell or tissue.

As herein defined, the term "a TLR2 expressing cell or tissue implicated in ischemia reperfusion injury" means a cell or tissue which causes the onset or progression of ischemia reperfusion injury, or of a cell type or tissue which is undergoing ischemia reperfusion injury.

In certain embodiments the TLR2 expressing cell or tissue is a cell or tissue of the myocardium. In certain embodiments the TLR2 expressing cell or tissue is a cell or tissue involved with a reperfusion induced cardiac inflammatory condition selected from the group comprising, but not limited to: myocardial ischemia, ischemic heart disease, hypertension myocardial ischemia, congestive heart failure, tissue ischemia, organ ischemia, acute coronary syndrome, hypertrophy, cerebral infarction, myocardial infarction, arrhythmia, ischemia reperfusion injury (I/R injury).

In certain embodiments the step of contacting the tissue and/or cell with the TLR2 antagonist occurs in a cell lysate, a reconstituted system or cells in culture. In certain embodiments the contacting step occurs on cells or a tissue present in a subject. In certain embodiments the TLR2 may be human TLR2 or murine TLR2.

In certain embodiments the method is performed on a human subject having, or at risk of having ischemia reperfusion injury.

In certain embodiments the at least one TLR2 antagonist is selected from the group comprising, but not limited to: a protein, a peptide, a peptidomimetic, a nucleic acid, a carbohydrate, a lipid, and a small molecule compound.

In certain embodiments the TLR2 antagonist is an antibody molecule. Typically the antibody has binding specificity to an epitope present on human TLR2, and in particular to an epitope comprising amino acid residues of the defined extracellular domain of TLR2. In certain embodiments the TLR2 antagonist binds to a non-continuous epitope comprising amino acid residues derived from the amino and carboxyl terminals of the amino acid sequence of human TLR2. In certain embodiments the TLR2 antagonist binds to an epitope on TLR2 comprising amino acid residues 19 to 39, or 538 to 549 of SEQ ID NO:1.

In certain embodiments the antibody is selected from the group consisting of, but not limited to: a human, humanised, chimeric, synthetic, camelid, shark or in-vitro antibody, which has binding specificity to TLR2. In certain further embodiments, a binding fragment may be used, said binding fragment being derived from any of the aforementioned antibodies. In certain embodiments the antibody is an antibody binding fragment selected from the group consisting of a Fab, scFv, Fv, dAb, and fragment. In certain embodiments the antibody molecule comprises two complete heavy chains, and two complete light chains, or an antigen-binding fragment thereof. In certain embodiments, the antibody is of the isotype IgG, IgA, IgM. In embodiments where the antibody is of the isotype IgG, the antibody may be of the subtype IgG1, IgG2 or IgG3.

In certain embodiments, the antibody is a murine IgG1 anti-TLR2 antibody (mouse Toll-like Receptor 2 (TLR2) antibody, derived from hybridoma clone T2.5, HyCult Biotechnology b.v., Cell Sciences, Canton, USA: catalogue number 1054), or a humanised version thereof.

In certain embodiments the TLR2 antagonist inhibits the expression of at least one nucleic acid which encodes for the TLR2 protein. In certain embodiments the TLR2 antagonist is selected from the group comprising, but not limited to: anti-sense oligonucleotides, triple helix molecules, anti-sense DNA, anti-sense RNA, ribozyme, iRNA, miRNA, siRNA, shRNA molecule.

In certain embodiments, more than one TLR2 antagonistic compound is administered to the cell, tissue or subject. For example, a TLR2 specific TLR2 antagonistic antibody may be administered to prevent the activation of TLR2, while an inhibitory nucleic acid may also be administered to inhibit the expression of TLR2.

According to a yet further aspect of the invention there is provided a method for the treatment and/or prophylaxis of ischemia reperfusion injury or a condition caused thereby or associated therewith, the method comprising the steps of:

providing a therapeutically effective amount of an agent which modulates the function of Toll-like Receptor 2, and administering said compound to a subject in need of such treatment.

As herein defined, the term 'modulates the function' means that the agent changes or alters one or more of the biological functional activities of Toll-like Receptor 2. In certain embodiments, the modulation of Toll-like Receptor 2 function means that the agent inhibits the functional activation of Toll-like Receptor 2 following the binding of a TLR2 specific ligand and/or inhibits or suppresses the downstream intracellular signalling mediated by Toll-like Receptor 2 following activation by a TLR2 ligand, or the like. Modulation of the function of TLR2 may further extend to a suppression or inhibition of the expression of Toll-like Receptor 2 protein, or the inhibition or blocking of the expression of a gene which encodes Toll-like Receptor 2, hence, an agent which modulates TLR2 function may further inhibit the expression of the TLR2 protein, or block the expression of the TLR2 gene product.

As defined herein, an 'agent' which modulates TLR2 is a compound which suppresses or blocks the activation or function of Toll-like Receptor 2. The 'agent' may be an antagonist compound which inhibits or blocks the binding of a ligand or binding compound to Toll-like Receptor 2. For example, the 'agent' may be a Toll-like Receptor 2 binding agent which binds to the extracellular domain of Toll-like Receptor 2, said agent inhibiting the binding of activating ligands which have binding specificity for TLR2. Further, the 'agent' may be a compound which inhibits or suppresses intracellular signalling mediated by Toll-like Receptor 2 following ligand binding and/or Toll-like Receptor 2 activation. The 'agent' may further be a compound which modulates Toll-like Receptor 2 protein or gene expression, for example by inhibiting the expression of a gene encoding a Toll-like Receptor 2 protein. Such a compound may also be known as a TLR2 modulator agent.

In certain embodiments, the 'agent' which modulates TLR2 function may be a binding compound which has binding specificity or which specifically binds Toll-like Receptor 2. In certain embodiments, the binding compound may be selected from the group comprising, but not limited to: a protein, a peptide, a peptidomimetic, a nucleic acid, a polynucleotide, a polysaccharide, an oligopeptide, a carbohydrate, a lipid, an aptamer, a small molecule compound, and a naturally occurring compound, such as a plant derived compound or mimetic, analogue or derivative thereof.

In certain embodiments, the agent is a binding compound which binds to Toll-like Receptor 2 at a binding site other than the known TLR2 ligand binding site, and which, upon binding to TLR2, causes a change in the confirmation of Toll-like Receptor 2, which leads to an inhibition of Toll-like Receptor 2 activation and/or TLR2 agonistic ligand binding.

The term "specifically binds" or "binding specificity" refers to the ability of a TLR2 modulator agent or TLR2 binding compound to bind to a target epitope present on TLR2 with a greater affinity than it binds to a non-target epitope. In certain embodiments, specific binding refers to binding to a particular target epitope which is present on TLR2 with an affinity which is at least 10, 50, 100, 250, 500, or 1000 times greater than the affinity for a non-target epitope. In certain embodiments, binding affinity is determined by an affinity ELISA assay. In certain embodiments, affinity is determined by a BIAcore assay. In certain embodiments, binding affinity is determined by a kinetic method. In certain embodiments, affinity is determined by an equilibrium/solution method.

According to one embodiment, TLR2 modulators, including TLR2 binding agents, such as TLR2 antagonists, bind to TLR2 with high affinity, this being defined as a binding affinity which for example, has an affinity constant of at least about $10^7$ $M^{-1}$, typically about $10^8$ $M^{-1}$, and more typically, about $10^9$ $M^{-1}$ to $10^{10}$ $M^{-1}$ or stronger; and which modulates, e.g., reduces and/or inhibits, one or more TLR2 biological activities in a TLR2 responsive cell and/or tissue.

In certain embodiments, the TLR2 modulator agent is targeted to Toll-like Receptor 2 expressed on the cells or tissues which are likely to undergo reperfusion following a period of ischemia. Such targeting may be by any suitable means known to the person skilled in the art, such as localised delivery, the use of a delivery vector, or a targeting means, such as an antibody which has binding specificity for a cell surface target expressed on the cell or tissue which is to be targeted. Examples of exemplary TLR2 activities that can be modulated, e.g., inhibited or reduced, using the methods and compositions of the invention include, but are not limited to, one or more of the following: (i) inhibiting or suppressing TLR2 expression, (ii) inhibiting TLR2 ligand binding and associated TLR2 activation, and (iii) inhibiting or suppressing intracellular signalling mediated by TLR2.

Accordingly, in a further aspect, the invention provides a method of modulating a function (e.g., altering one or more biological activities of TLR2) in a TLR2-responsive cell and/or tissue (e.g., a tissue which has undergone ischemia, which may undergo ischemia, or which may undergo reperfusion). The method includes contacting the TLR2-responsive cell and/or TLR2-responsive tissue with a TLR2 modulator agent, e.g., a TLR2-binding agent, for example an antagonist of human TLR2 activity or expression, in an amount sufficient to modulate the function of the TLR2-responsive cell or tissue, or the biological activity of TLR2 in the cell or tissue. In one embodiment, the contacting step can be effected in vitro, for example in a cell lysate or in a reconstituted system. Alternatively, the subject method can be performed on cells in culture, e.g., in-vitro or ex-vivo. For example, cells, such as purified or recombinant cells, can be cultured in-vitro and the contacting step can be effected by adding the TLR2 modulator to the culture medium. Typically, the TLR2-responsive cell is a mammalian cell, such as a human cell. In some embodiments, the TLR2-responsive tissue is a tissue which has undergone ischemia and which may undergo reperfusion, or is a cellular population associated therewith. In other embodiments, the method can be performed on cells present in a subject, e.g., as part of an in-vivo protocol, or in an animal subject (including, e.g., a human subject, or an in-vivo animal model). The in-vivo protocol can be therapeutic or prophylactic, and the inflammatory model can be, for example, a genetically modified model, such as an animal model having overexpressed TLR2, or a mutation or deletion in a TLR receptor. For in vivo methods, the TLR2 modulator, alone or in combination with another agent, can be administered to a subject suffering from an autoimmune disease such as rheumatoid arthritis, in an amount sufficient to modulate, one or more TLR2 mediated activities or functions in the subject. In some embodiments, the amount or dosage of the TLR2 modulator that is administered can be determined prior to administration by testing in-vitro or ex-vivo, the amount of TLR2 modulator required to alter, e.g., decrease or inhibit, one or more functional activity of TLR2, said functional activity typically being one or more TLR2 biological activities described herein.

In certain embodiments where inhibition, reduction or diminution of one or more TLR2 biological activities is desired, the TLR2-responsive cell and/or tissue is contacted with a TLR2 antagonist, e.g., by administering the TLR2 antagonist to the subject. In one embodiment, the TLR2 antagonist interacts with, e.g., binds to, a TLR2 polypeptide or mRNA involved in the expression of the TLR2 protein, and reduces or inhibits one or more TLR2 activities. Typically, the TLR2 antagonized is a mammalian TLR2 (or a functional variant thereof), e.g., human TLR2 or murine TLR2. In certain embodiments, the TLR2 antagonized includes the human TLR2 sequence as defined in FIG. 12 (SEQ ID NO:1) (comprising the 784 amino acid full length human Toll-like Receptor sequence as defined as Genbank Accession Number MC 34133 (URL www.ncbi.nlm.nih.gov)) or of the murine TLR2 sequence comprising the amino acid sequence defined in FIG. 13 (SEQ ID NO:2) (Genbank Accession Number NP_036035 (*Mus musculus*)), or a portion thereof, and/or an amino acid sequence substantially homologous thereto, in particular having at least 90% sequence homology identity, or to an amino acid sequence encoded by a nucleotide sequence.

As herein defined, the term "Toll-like Receptor 2 activation" means the binding of Toll-like Receptor 2 by a ligand, wherein the ligand acts as an agonist and activates Toll-like Receptor 2 in order to induce an intracellular signalling cascade. Intracellular signalling mediated following Toll-like Receptor 2 activation and signalling results in the activation of transcription factors and the expression of genes which mediate a pro-inflammatory immune response.

In certain embodiments the TLR2 modulator agent inhibits the interaction between Toll-like Receptor 2 and a Toll-like Receptor 2 agonist ligand.

In certain embodiments, the TLR2 modulator agent that suppresses Toll-like Receptor 2 activation and/or signalling is a compound which acts as a Toll-like Receptor 2 antagonist. Typically, antagonism of Toll-like Receptor 2 function is achieved by the binding of the Toll-like Receptor 2 modulator agent to Toll-like Receptor 2 in such a way that ligand binding to Toll-like Receptor 2 is prevented. This inhibition of Toll-like Receptor 2 ligand binding may be achieved by a number of means, for example, through partially or fully blocking the Toll-like Receptor 2 ligand binding site, or by inducing a conformational change upon binding to or association with Toll-like Receptor 2 which results in the Toll-like Receptor 2 ligand binding site being altered in a manner which prevents Toll-like Receptor 2 ligand binding, for example due to a conformational change of the tertiary structure of the Toll-like Receptor 2 ligand binding site which prevents TLR2 ligand binding.

In certain embodiments, the TLR2 modulator agent binds to at least one epitope present on TLR2, wherein binding to this epitope results in an inhibition of TLR2 function, most typically TLR2 activation or TLR2 mediated downstream signalling. As herein defined, an "epitope" refers to a plurality of amino acid residues which encode for the TLR2 protein which are capable of being recognised by, and bound to by, a binding compound such as a ligand, small molecule, antibody or the like. Epitopes are generally comprised of chemically active surface groups and have specific three dimensional structural characteristics, as well as specific charge characteristics, the aforementioned contributing to the three dimensional structure of the epitope.

Typically, the TLR modulator agent antagonises the functional activity of TLR2 and as such binds to an epitope known as an inhibiting epitope or an inhibitory epitope. An "inhibiting" or "inhibitory" epitope means an epitope present on TLR2 that, when bound by a binding compound such as a small molecule or an antibody, results in the loss of biological activity of TLR2, for example due to the binding compound preventing the binding of TLR2 by a TLR2 agonist. The epitope that is present on TLR2, and which is bound by the binding compounds in order to antagonise TLR2 function, may comprise 5 or more amino acid residues.

In certain embodiments, the TLR2 modulator agents of the invention recognise a continuous epitope. In further embodiments, the epitope is a discontinuous epitope which comprises residues derived from both the N-terminal (amino terminal) and C-terminal (carboxy terminal) portions of the mature Toll-like receptor 2 (TLR2) protein. In certain embodiments, the epitope may comprise residues 19 to 39 as determined from the 586 amino acid sequence of the extracellular domain of Toll-like Receptor 2 as shown in SEQ ID NO: 3 (FIG. 1$). Such an epitope may be further defined with reference to the amino acids which it comprises, said epitope comprising at least amino acid residues KEESSNQASLSCDRNGICKGS (SEQ ID NO:4) of the extracellular domain of TLR2 as defined in SEQ ID NO:3. Further, the binding epitope may further comprise amino acids residues 538 to 549 of Toll-like Receptor 2 as present at the C-terminal region of the amino acid sequence of SEQ ID NO:1, this sequence comprising the amino acids CSCEFLSFTQEQQ (SEQ ID NO:5). The TLR2 modulatory agent binding site may further be defined by amino acid residues 19 to 39, or 538 to 549 of SEQ ID NO:1, or by amino acid residues 19 to 39 and 538 to 549 of SEQ ID NO:1.

The reduction, inhibition or antagonism of Toll-like Receptor 2 functional activity may occur regardless of whether Toll-like Receptor 2 forms a heterodimer with another Toll-like Receptor, such as Toll-like Receptor 1, Toll-like Receptor 6 or another Toll-like Receptor, such as Toll-like Receptor 4 or Toll-like Receptor 10. By the term "Toll-like Receptor 2 activation and downstream mediated signaling" it is meant any intracellular signaling pathway which is induced by activation of TLR2. The signaling pathway may be a TLR2 specific pathway, or may be a "shared" signalling pathway, for example where the signalling pathway may be activated by other sources, for example, by means of the activation of receptors other than TLR2 which contribute to the activation of mediators of the immune response such as the transcription factor NF-kappaB.

TLR2 is known to dimerise into 2 functional heterodimers. In particular, TLR2 is known to form a heterodimer with either Toll-like Receptor 1 or Toll-like Receptor 6. It is possible that further heterodimers are formed with Toll-like Receptor 4 (TLR4, TLR-4) and Toll-like Receptor 10 (TLR10, TLR-10). It is thought that this dimerisation is associated with a discrimination that results in the binding of TLR2 by different microbial-derived ligands. In addition, the ectodomain of TLR2 may form a soluble heterodimer with CD14 in the circulatory system and in mammalian milk.

The inventors have recognised that, in order to provide a therapeutic approach which is comprehensive in suppressing TLR2-mediated inflammation during or following reperfusion following ischemia, that it would be desirable to provide a binding compound which has binding specificity for TLR2, regardless of whether a heterodimer is formed between TLR2 and another TLR, such as, for example, TLR1, TLR6, TLR4 or TLR10. In this regard, following extensive experimentation, the inventors have identified a conformational, discontinuous epitope comprised of amino acid residues present at both the N-terminal and C-terminal of the TLR2 protein which, when bound, suppresses TLR2 functional activity. Binding of this epitope by a TLR2 antagonistic binding compound serves to suppress the function of TLR2 irrespective of whether TLR2 forms a heterodimer with TLR1, TLR4, TLR6 or TLR10.

Accordingly, in certain further embodiments, the TLR2 modulator agent provided by the present invention may have at least one of the following characteristics: (i) it is a monoclonal antibody, (ii) it is a human-derived or in-vitro generated antibody, (iii) it binds to a conformational, discontinuous epitope of human or murine TLR2 comprising the amino acids of SEQ ID NO:4 and/or SEQ ID NO:5 and mediates TLR2 functional suppression irrespective of whether a heterodimer is formed between TLR2 and TLR1, TLR6, TLR4 or TLR10, (iv) it binds to the epitope present on the extracellular domain of TLR2 with an affinity constant (Ka) of at least $10^{-6}$M.

In certain embodiments, the TLR2 modulator agent which suppresses or inhibits Toll-like Receptor 2 function and/or signalling and/or expression is selected from at least one of the group comprising, but not limited to: proteins, peptides, peptidomimetics, nucleic acids, polynucleotides, polysaccharides, oligopeptides, carbohydrates, lipids, small molecule compounds, and naturally occurring compounds.

Typically, the agent which modulates TLR2 function is a TLR2 antagonist. In certain embodiments, the TLR2 antagonist is a binding compound selected from the group consisting of a protein, a peptide, a peptidomimetic, a nucleic acid, a carbohydrate, a lipid, and a small molecule compound.

In certain embodiments, the TLR2 antagonist is an antibody or a binding fragment derived therefrom. In certain embodiments, the antibody is selected from the group consisting of: a monoclonal antibody, a polyclonal antibody or a synthetic antibody. In certain further embodiments, the antibody is selected from the group comprising; a human, humanised, camelid, in vitro generated antibody to human TLR2. The antibody may be of an isotype selected from the group consisting of IgG, IgA, IgM, and IgE. The antibody may bind to an inhibitory epitope present on TLR2 with a dissociation constant (Kd) of from about $10^{-7}$M to about $10^{-11}$M.

In certain embodiments the TLR2 modulatory agent is a soluble form of recombinant Toll-like Receptor 2. In particular the soluble form of TLR2 is a fusion protein substantially comprising the extracellular domain on the TLR2 protein conjoined to a secondary protein. In certain embodiments, the secondary protein may be an Fc domain of an antibody, or a fragment thereof.

In certain further embodiments, the TLR2 modulatory agent is an inhibitory nucleic acid which inhibits expression of the TLR2 protein. In certain embodiments the inhibitory nucleic acid protein is selected from the group consisting of: anti-sense oligonucleotides, triple helix molecules, anti-sense DNA, anti-sense RNA, ribozyme, iRNA, miRNA, siRNA, and shRNA.

In certain embodiments, the methods of the invention are used to administer a therapeutically effective amount of a TLR2 modulator agent to a subject in need of such treatment in order to reduce or inhibit one or more TLR2 biological activities in a TLR2 expressing cell or tissue of the myocardium, thereby treating the condition.

In certain embodiments, the methods of the invention may be used for the treatment or prevention of ischemia reperfusion injury which may result from at least one condition selected from the group consisting of hypoxia, stroke, heart attack, chronic kidney failure or organ transplantation in a subject.

In certain embodiments, the methods may comprise the further step of administering a therapeutically effective amount of at least one secondary therapeutic compound for use in the treatment or prevention of ischemia/reperfusion injury or an associated condition. Typically, said secondary therapeutic compound may be selected from the group consisting of: a glucocorticoid, a cytostatic, an anti-metabolite, an anti-CD2 antibody or related binding fragment, an anti-CD20 antibody, an anti-TNF-alpha antibody, cyclosporine, tacrolimus, sirolimus or FTY720.

In certain further embodiments, said secondary therapeutic compound may be selected from the group consisting of: an HMG-CoA reductase inhibitor, a vasodilatory agent, a diuretic, an angiotensin converting enzyme inhibitor, a beta-blocker, an angiotensin II receptor antagonist, a calcium channel blocker, an anticoagulant, an adenosine diphosphate receptor antagonist such as ticlopidine or clopidogrel bisulfate, a glycoprotein IIb/IIIa receptor antagonist such as bivalirudin, argatroban or heparin, a beta adrenergic receptor agonist, an antithrombolytic agent, an antioxidant, and an alpha blocker.

In certain embodiments, the secondary therapeutic agent may be administered simultaneously, sequentially or separately to the at least one TLR2 modulator agent.

In certain embodiments, the TLR2 modulatory compound is administered to a subject prior to, during, or following the subject undergoing a surgical procedure selected from the group consisting of; angioplasty, cardiac bypass surgery, thrombolysis, endarterectomy, organ transplantation and coronary artery bypass grafting (CABG). In certain embodiments, the method is performed on a subject prior to, during or following the occurrence of an ischemic event occurring in a cell or tissue. In certain embodiments, the method is performed on a subject during or following the occurrence of reperfusion. In certain embodiments, the method is performed on a subject during an acute window time period which is clinically determined following an ischemic event.

In certain embodiments, the methods of this aspect of the invention prevent ischemia reperfusion injury and accordingly inhibit organ damage following or during reperfusion. In certain further embodiments, the method of this aspect of the invention prevents ischemia reperfusion injury through the suppression or inhibition of a pro-inflammatory immune response which is mediated by signalling through Toll-like Receptor 2 (TLR2, TLR-2, CD282) and which is causative of cell, tissue or organ injury, during or following reperfusion following ischemia of the cell, tissue or organ.

According to a yet further aspect of the invention there is provided a pharmaceutical composition for use in the treatment and prophylaxis of ischemia reperfusion injury or a condition associated therewith comprising an agent which modulates the function or expression of Toll-like Receptor 2 along with at least one pharmaceutically acceptable carrier, diluent, solubilizer, emulsifier, preservative and/or adjuvant.

In certain embodiments the TLR2 modulator agent is a compound which is a TLR2 antagonist selected from the group consisting of: a polyclonal antibody, a monoclonal antibody, a humanized antibody, a chimeric antibody or antibody fragment, an aptamer, a fusion protein and a peptidomimetic.

In certain embodiments, the TLR2 modulator agent is a soluble form of the TLR2 receptor. Said soluble form of TLR2 may be recombinant.

In certain embodiments the TLR2 modulator agent is an inhibitory nucleic acid based compound which inhibits the expression of TLR2.

In certain embodiments, the pharmaceutical composition may further comprise a secondary therapeutic agent, such as, but not limited to: an immune suppressor, which may be at least one of the group consisting of, but not limited to: a glucocorticoid, in particular a glucocorticoid which suppresses the expression of a cytokine; a cytostatic such as an alkylating agent, an anti-metabolite such as methotrexate; an antibody or related binding fragment, such as an anti-CD3 antibody such as OKT-3, an anti-CD20 antibody, the anti-TNF-alpha antibody infliximab (REMICADE™), etanercept (ENBREL™) or adalimumab (HUMIRA™); a drug compound which acts on immunophilins such as cyclosporine, tacrolimus or sirolimus; or a small molecule, such as FTY720 or a therapeutic cardiovascular compound comprising at least one or more of; an HMG-CoA reductase inhibitor, a vasodilatory agent, a diuretic, an angiotensin converting enzyme inhibitor, a beta-blocker, an angiotensin II receptor antagonist, a calcium channel blocker, an anticoagulant, an adenosine diphosphate receptor antagonist such as ticlopidine or clopidogrel bisulfate, a glycoprotein IIb/IIIa receptor antagonist such as bivalirudin, argatroban or heparin, a beta adrenergic receptor agonist, an antithrombolytic agent, an antioxidant, and an alpha blocker.

In certain embodiments, the Toll-like Receptor 2 modulator agent is orally administered to the subject at a dose of from about 1 mg/kg to about 10 mg/kg of the subject's body weight per day. In certain embodiments, the dose of the Toll-like Receptor 2 modulator agent is from about 100 mg per day to about 1000 mg per day. In certain further embodiments, the dose of the Toll-like Receptor 2 modulator agent is from about 200 mg per day to about 300 mg per day.

In certain embodiments, the Toll-like Receptor 2 modulator agent is administered to the subject parenterally with a dosage range of between about 0.001 mg/kg to 1.0 mg/kg of the mammal's body weight.

In certain embodiments, the Toll-like Receptor 2 modulator agent is administered to the subject for a time, and under conditions sufficient to down regulate the level and/or activity of Toll-like Receptor 2.

A yet further aspect of the present invention provides a method for treating or preventing a cardiac disease or a disease condition related thereto, the method comprising the steps of:
  providing a therapeutically effective amount of an agent which modulates the function of Toll-like Receptor 2, and
  administering said compound to a subject in need of such treatment.

In certain embodiments the cardiac inflammatory condition is selected from the group consisting of, but not limited to: myocardial ischemia, ischemic heart disease, hypertension myocardial ischemia, congestive heart failure, tissue ischemia, organ ischemia, acute coronary syndrome, hypertrophy, cerebral infarction, myocardial infarction, arrhythmia, ischemia reperfusion injury (I/R).

In certain embodiments the agent which modulates TLR2 function is a TLR2 antagonist. In certain embodiments the TLR2 antagonist is a binding compound selected from the group consisting of, but not limited to: a protein, a peptide, a peptidomimetic, a nucleic acid, a carbohydrate, a lipid, and a small molecule compound.

In certain embodiments the TLR2 modulator agent is a compound which is a TLR2 antagonist selected from the group consisting of: a polyclonal antibody, a monoclonal antibody, a humanized antibody, a chimeric antibody or antibody fragment, an aptamer, a fusion protein and a peptidomimetic.

In certain embodiments, the TLR2 modulator agent is a soluble form of the TLR2 receptor. Said soluble form of TLR2 may be produced by recombinant techniques.

In certain embodiments the TLR2 modulator agent is an inhibitory nucleic acid based compound which inhibits the expression of TLR2. In certain embodiments the inhibitory nucleic acid may be selected from the group consisting of: anti-sense oligonucleotides, triple helix molecules, anti-sense DNA, anti-sense RNA, ribozyme, iRNA, miRNA, siRNA, and shRNA.

In certain embodiments the TLR2 antagonist is an antibody or a binding fragment derived therefrom. The antibody may be selected from the group consisting of: a monoclonal antibody, a polyclonal antibody or a synthetic antibody.

In certain embodiments, the method may further comprise the step of administering a secondary therapeutic compound as described hereinbefore.

Accordingly, a further aspect of the present invention provides a method of preventing tissue or organ damage resulting from reperfusion, the method comprising the step of:
  providing a therapeutically effective amount of an inhibitory nucleic acid, which blocks the expression of the Toll-like Receptor 2 protein, and
  administering the same to a subject in need of such treatment.

In certain embodiments, the inhibitory nucleic acid may include, but is not limited to; anti-sense oligonucleotides, anti-sense DNA, anti-sense RNA, ribozyme, iRNA, miRNA, siRNA, shRNA.

In certain embodiments, the reperfusion occurs following a period of ischemia of said organ or tissue.

As herein defined, the terms "blocks" and "blocking" when used in relation to Toll-like Receptor 2 gene expression mean silencing the expression of at least one gene which results in the expression of the Toll-like Receptor 2 protein.

Gene silencing is the switching off of the expression of a gene by a mechanism other than genetic modification. Gene silencing can be mediated at the transcriptional level or at the post-transcriptional level. Transcriptional gene silencing can results in a gene being inaccessible to transcriptional machinery, and can be mediated, for example, by means of histone modifications. Post-transcriptional gene silencing results from the mRNA of a gene being destroyed, thus preventing an active gene product, such as a protein, in the present case the TLR2 protein.

Accordingly, in one embodiment this aspect of the present invention provides for the administration to a subject of an effective amount of an inhibitory nucleic acid molecule such as an RNAi (RNA interference) agent, for example an interfering ribonucleic acid (such as siRNA or shRNA) or a transcription template thereof, such as a DNA encoding an shRNA to at least one cell type, tissue or organ present in the subject in order to block the expression of the TLR2 protein.

In certain further embodiments, the inhibitory nucleic acid molecule may be an antisense RNA molecule. Antisense causes suppression of gene expression and involves single stranded RNA fragments which physically bind to mRNA, this blocking mRNA translation. Techniques for the preparation of appropriate nucleic acid for use an inhibitory nucleic acid are well known to the person skilled in the art.

According to a further aspect of the invention there is provided the use of an inhibitory nucleic acid which blocks the expression of the Toll-like Receptor 2 protein in the preparation of a medicament for the treatment of cellular, tissue or organ damage resulting from reperfusion.

A yet further aspect of the invention provides an inhibitory nucleic acid for use in blocking the expression of the Toll-like Receptor 2 for treating cellular, tissue or organ damage resulting from reperfusion.

In certain embodiments, the reperfusion occurs following a period of ischemia.

In certain embodiments the inhibitory nucleic acid is selected from the group consisting of: anti-sense oligonucleotides, anti-sense DNA, anti-sense RNA, ribozyme, iRNA, miRNA, siRNA, shRNA.

According to a yet further aspect of the present invention there is provided a pharmaceutical composition for the treatment of cellular, tissue or organ damage caused by ischemia/reperfusion injury, the composition comprising a therapeutically effective amount of an inhibitory nucleic acid which blocks the expression of Toll-like Receptor 2, along with at least one pharmaceutically acceptable carrier, diluent, solubiliser, emulsifier, preservative and/or adjuvant.

In certain embodiments the inhibitory nucleic acid is selected from the group consisting of, but not limited to: anti-sense oligonucleotides, anti-sense DNA, anti-sense RNA, ribozyme, iRNA, miRNA, siRNA, shRNA.

In certain embodiments the pharmaceutical composition may further comprise at least one immunosuppressor compound. In certain embodiments, the immunosuppressor (also known as an immunosuppressant) may be at least one of the group consisting of, but not limited to: a glucocorticoid, in particular a glucocorticoid which suppresses the expression of a cytokine; a cytostatic such as an alkylating agent, an anti-metabolite such as methotrexate; an antibody or related binding fragment, such as an anti-CD3 antibody such as OKT-3, an anti-CD20 antibody, the anti-TNF-alpha antibody infliximab (REMICADE™), etanercept (ENBREL™) or adalimumab (HUMIRA™); a drug compound which acts on immunophilins such as cyclosporine, tacrolimus or sirolimus; or a small molecule, such as FTY720.

Techniques for the preparation of appropriate nucleic acids for use as inhibiting nucleic acids which block the expression of Toll-like Receptor 2 are well known to the person skilled in the art.

In certain embodiments, the inhibitory nucleic acid is administered to a subject prior to, during, or following the subject undergoing a surgical procedure selected from the group consisting of, but not limited to; angioplasty, cardiac bypass surgery, thrombolysis, organ transplantation, endarterectomy, and coronary artery bypass grafting (CABG).

In certain further embodiments, the inhibitory nucleic acid is administered to a subject before, during or following an ischemic event. In certain embodiments, inhibitory nucleic acid is administered to a subject during or following reperfusion. In certain embodiments, the inhibitory nucleic acid is administered to a subject during an acute window following an ischemic event.

In certain embodiments, the inhibitory nucleic acid is administered to a subject prior to, during, or following the subject undergoing a surgical procedure being or relating to the transplantation of cells, tissues or at least one organ.

Typically, said method is performed in order to prevent, or limit a TLR2-mediated immune response which causes tissue damage, and in particular cell or tissue damage which results from reperfusion.

In a further aspect, the invention extends to the provision of at least one aptamer with binding specificity to Toll-like Receptor 2, which causes blocking or suppression of the functional activity of Toll-like Receptor 2. Techniques for the selection of suitable aptamers will be well known to the person skilled in the art, for example, using SELEX technology.

Accordingly, in various further embodiments, the present invention extends to a method of identifying and isolating nucleic acid ligands which have binding specificity for Toll-like Receptor 2, the method comprising the steps of:
  (a) providing a candidate mixture of nucleic acids
  (b) contacting a cell expressing Toll-like Receptor 2 with the candidate nucleic acid mixture
  (c) selecting nucleic acids which have an increased affinity to Toll-like Receptor 2 relative to the other candidate nucleic acids,
  (d) amplifying the selected nucleic acids in order to provide at least one nucleic acid with affinity for Toll-like Receptor 2, and
  (e) selecting at least one nucleic acid therefrom which has a high affinity and specificity for Toll-like Receptor 2.

The inventors have further identified that suppression of the function of Toll-like Receptor 2 can be achieved by means of reducing the amount of ligand which is available to bind to and activate membrane bound Toll-like Receptor 2. A reduction in the amount of ligand which is available to bind membrane bound Toll-like Receptor 2 results in a downregulation of Toll-like Receptor 2 mediated signalling and thus of TLR2-mediated activation of the pro-inflammatory immune response. In particular, the inventors have identified the utility of a soluble peptide which is either a soluble form of Toll-like Receptor 2 or a functional fragment thereof in suppressing Toll-like Receptor 2 mediated activation of a pro-inflammatory response. Said suppression results from the soluble form of Toll-like Receptor 2 or truncated non-membrane form of Toll-like Receptor 2 competing with the membrane bound form of TLR2 for TLR2 specific binding ligands. This competitive binding results in the soluble or truncated forms of TLR2 effectively "mopping up" available Toll-like Receptor 2 ligand. An associated reduction in the binding and activation of membrane bound Toll-like Receptor 2 results in a downregulation of the Toll-like Receptor 2 mediated pro-inflammatory immune response.

Accordingly, the administration of a soluble form of Toll-like Receptor 2 has utility in methods for suppressing the pro-inflammatory immune response which contributes to tissue injury during and following ischemia reperfusion.

Accordingly, a further aspect of the present invention provides a method for treating and/or preventing ischemia reperfusion injury of a cell, tissue or organ, the method comprising the steps of:
  providing a therapeutically effective amount of a soluble form of Toll-like Receptor 2 or a soluble fragment thereof which is capable of binding to a Toll-like Receptor 2 ligand, and
  administering a therapeutically effective amount of said compound to a subject in need of such treatment.

The amino acid sequence of the extracellular domain (ectodomain) of human Toll-like Receptor 2 is provided herein as SEQ ID NO:3 (FIG. 14). The extracellular domain of the human form of Toll-like Receptor 2 comprises 587 amino acid resides, specifically amino acids 1-587 of the defined 784 amino acid full length human Toll-like Receptor sequence as defined as Genbank Accession Number AAC 34133 (URL www.ncbi.nlm.nih.gov). As herein defined, the ectodomain of TLR2 is the portion of the membrane bound form of TLR2 which extends into the extracellular space.

In certain embodiments the soluble form of TLR2 is prepared by a recombinant technique. A soluble form of Toll-like Receptor 2 typically comprises the extracellular domain of TLR2 only, and hence the intracellular and transmembrane domains of Toll-like Receptor 2 as defined in Genbank Accession Number AAC 34133 are absent. In certain embodiments, the soluble form of Toll-like Receptor 2 may comprise amino acids 1 to 587 of the defined human Toll-like Receptor 2 sequence. The soluble Toll-like Receptor 2 sequence may be modified by means of the addition, deletion or substitution of 1 or more amino acid residues. Accordingly, in certain embodiments, the soluble form of the Toll-like Receptor 2 is derived from the extracellular domain of the determined membrane bound form of Toll-like Receptor 2 as defined herein in SEQ ID NO:3. In further embodiments, the soluble form of the Toll-like Receptor 2 is derived from a truncated form of the full length membrane bound Toll-like Receptor 2 amino acid sequence as defined herein in SEQ ID NO:3 (FIG. 14), wherein said truncated form exhibits the functional characteristics of (i) being soluble, and (ii) being capable of being bound by a ligand which has binding specificity to at least one epitope which is present on the membrane bound form of Toll-like Receptor 2.

In certain embodiments, in addition to a deletion and/or substitution of the amino acids residues relating to the intracellular and/or transmembrane domains defined from the membrane bound form of TLR2, a deletion and/or substitution may further be made to the amino acid residues of the extracellular domain. Any such deletion and/or substitution of the amino acid residues of the extracellular domain of the TLR2 may be made so long as the modified form of TLR2 is capable of binding a ligand which can bind to at least one epitope present on the membrane bound form of TLR2.

In certain embodiments, the soluble form of Toll-like Receptor 2 (sTLR2) may be targeted to an organ, tissue or cell which has undergone reperfusion following ischemia, or which is undergoing reperfusion following ischemia, or to at least one specific cell type which is undergoing ischemia, and which may, in due course, undergo reperfusion. The targeting of sTLR2 in this way is advantageous as systemic administration of sTLR2 may result in global immunosuppression of the TLR2 receptor and accordingly TLR2 mediated signalling which may be undesirable in some instances.

Targeting of soluble forms of sTLR2 may be provided through the formation of a fusion protein, wherein said fusion protein is comprised of a soluble portion of the TLR2 receptor, typically the extracellular domain or a portion thereof, conjoined to a secondary peptide, typically the Fc receptor binding protein is derived from the heavy chain of an immunoglobulin, typically a human immunoglobulin. The Fc domain has been extensively used to prolong the circulatory half-life of therapeutic proteins.

In certain embodiments, the soluble form of sTLR2 may be administered prior to, during, or following the subject undergoing a surgical procedure selected from the group consisting of, but not limited to; angioplasty, cardiac bypass surgery, thrombolysis, organ transplantation, endarterectomy, and coronary artery bypass grafting (CABG).

In certain further embodiments, the soluble form of sTLR2 may be administered to a subject before, during or following an ischemic event. In certain embodiments the soluble form of sTLR2 may be administered to a subject during or following the occurrence of reperfusion. In certain embodiments, the soluble form of sTLR2 may be administered to a subject during an acute window following an ischemic event.

In certain embodiments, the soluble form of sTLR2 may be administered to a subject prior to, during, or following the subject undergoing a surgical procedure being or relating to the transplantation of cells, tissues or at least one organ. Typically, said method is performed in order to prevent, or limit a TLR2-mediated immune response which causes tissue damage.

A yet further aspect of the present invention provides a kit comprising a pharmaceutical preparation comprising an agent which suppresses the function, expression or signalling mediated by a membrane bound form of Toll-like Receptor 2 along with instructions for the administration of said preparation.

In certain embodiments, the instructions may specify that the preparation should be administered to a subject prior to, during, or following a surgical procedure selected from the group comprising, but not limited to; bypass surgery, thrombolysis, endaterectomy and angioplasty.

The present invention further extends to screening assays for use in identifying compounds which are capable of preventing reperfusion damage to cells, tissues or organs during or following reperfusion, wherein said reperfusion damage is mediated by activation of TLR2 or by signalling through the TLR2 pathway by means of suppressing the function of Toll-like Receptor 2.

A yet further aspect of the present invention provides a screening method for the identification of compounds which suppress Toll-like Receptor 2 mediated inflammation and associated cell, tissue or organ damage occurring during or following reperfusion, the method comprising:

providing membrane bound Toll-like Receptor 2 receptor along with a ligand which has binding specificity thereto, bringing a candidate compound into contact with Toll-like Receptor 2, exposing Toll-like Receptor 2 to a Toll-like Receptor 2 ligand, determining the binding of the Toll-like Receptor 2 ligand to Toll-like Receptor 2, wherein the inhibition of binding of Toll-like Receptor 2 by the Toll-like Receptor 2 ligand indicates that said candidate compound is a modulator of Toll-like Receptor 2 activation and signalling.

In certain embodiments, the compounds which suppress Toll-like Receptor 2 mediated inflammation and associated cell, tissue or organ damage occurring during or following reperfusion are TLR2 agonists.

A further aspect of the present invention provides a modulator agent identified according to the foregoing aspect of the invention for use in the suppression of a TLR2-mediated inflammatory response for the prevention or treatment of reperfusion injury.

As herein defined, reperfusion injury refers to damage to tissue caused when blood supply returns to a tissue following a period of ischemia. Reperfusion injury is thought to be associated with the ischemic cascade of the brain, this being involved in stroke and brain trauma, hence the TLR2 modulator agents of the invention, in preventing reperfusion injury may also serve to prevent stroke and/or brain trauma.

The inventors have further recognised the utility of the methods and TLR2 modulatory agents of the present invention for use in improving transplantation of cells, tissues or an organ to a subject by preventing immunological rejection of the transplanted donor cells, or tissues in the recipient Generally, during the transplantation procedure, a donor organ, tissue or cell mass is subjected to prolonged ischemia due to a lack of a blood supply and thus, oxygen levels within the donor organ, tissue or cell mass are depleted. The immune response, which is believed to be a major contributing factor to reperfusion injury, may further contribute to the more general immune response which results in graft rejection which is mounted by the host following the transplantation procedure.

Accordingly, a yet further aspect of the present invention provides a method for suppressing an aberrant immune response which may contribute to the rejection of a transplanted tissue, organ or cell mass by a recipient, the method comprising the steps of providing a therapeutically effective amount of an agent which modulates Toll-like Receptor 2 activation and/or signalling, and administering a therapeutically effective amount of said compound to a subject in need of such treatment.

A yet further aspect of the present invention provides for the use of an agent which suppresses the function of Toll-like Receptor 2 in the preparation of a medicament for use in preventing an aberrant immune response which causes rejection of a donor organ which is received by a recipient following a transplantation surgical procedure.

The inventors have further identified the utility of the methods and compounds of the present invention for the treatment of cardiac diseases which are associated with, or related to, ischemic reperfusion injury.

Accordingly, a further aspect of the present invention provides a method for treating or preventing a cardiac disease or a disease condition related thereto, the method comprising the steps of:

providing a therapeutically effective amount of a Toll-like Receptor 2 suppressor agent and administering the same to a subject in need of said treatment.

In certain embodiments, the cardiac inflammatory condition may be at least one condition selected from the group comprising: myocardial ischemia, ischemic heart disease, hypertension myocardial ischemia, congestive heart failure, tissue ischemia, organ ischemia, acute coronary syndrome, hypertrophy, cerebral infarction, myocardial infarction, arrhythmia, ischemia reperfusion injury (I/R).

According to a further aspect of the present invention, there is provided a pharmaceutical composition for the treatment of a cardiac disease or a disease or inflammatory condition related thereto, the composition comprising a binding compound which has binding specificity for Toll-like Receptor 2 and which inhibits the function thereof, along with at least one pharmaceutically acceptable carrier, diluent, solubilizer, emulsifier, preservative and/or adjuvant.

In certain embodiments, the cardiac disease or disease condition related thereto may be at least one condition selected from the group comprising: myocardial ischemia, ischemic heart disease, hypertension myocardial ischemia, congestive heart failure, tissue ischemia, organ ischemia, acute coronary syndrome, hypertrophy, cerebral infarction, myocardial infarction, arrhythmia, ischemic reperfusion injury (I/R), atherosclerosis, allograft vasculopathy, hypertension, congestive heart failure.

In certain embodiments, the pharmaceutical composition may further comprise a secondary therapeutic agent, such as, but not limited to: an immune suppressor, which may be at least one of the group consisting of, but not limited to: a glucocorticoid, in particular a glucocorticoid which suppresses the expression of a cytokine; a cytostatic such as an alkylating agent, an anti-metabolite such as methotrexate; an antibody or related binding fragment, such as an anti-CD3 antibody such as OKT-3, an anti-CD20 antibody, the anti-TNF-alpha antibody infliximab (Remicade), etanercept (ENBREL) or adalimumab (HUMIRA); a drug compound which acts on immunophilins such as cyclosporine, tacrolimus or sirolimus; or a small molecule, such as FTY720 or a therapeutic cardiovascular compound comprising at least one or more of; an HMG-CoA reductase inhibitor, a vasodilatory agent, a diuretic, an angiotensin converting enzyme inhibitor, a beta-blocker, an angiotensin II receptor antagonist, a calcium channel blocker, an anticoagulant, an adenosine diphosphate receptor antagonist such as ticlopidine or clopidogrel bisulfate, a glycoprotein IIb/IIIa receptor antagonist such as bivalirudin, argatroban or heparin, a beta adrenergic receptor agonist, an antithrombolytic agent, an antioxidant, and an alpha blocker.

A yet further aspect of the present invention provides for the use of a binding agent, which has binding specificity for Toll-like Receptor 2, and that functions to suppress the function of Toll-like Receptor 2 in the preparation of a medicament for the treatment of inflammation associated with cardiac disease.

BRIEF DESCRIPTION OF THE FIGURES

The present invention will now be described with reference to the following examples which are provided for the purpose of illustration and are not intended to be construed as being limiting on the present invention wherein:

FIG. 1 shows a cross section of the heart following administration of a p38 inhibitor (SB239063) as a positive control;

FIG. 2 shows a cross section of the heart following administration of PBS;

FIG. 3 shows a cross section of the heart following administration of an antibody of the IgG isotype as a negative control;

FIG. 4 shows a cross section of the heart following administration of the experimental anti-TLR2 antagonistic monoclonal antibody OPN-301;

FIG. 5 shows a graph of the Area At Risk (AAR) as a percentage of the total Left Ventricle (LV);

FIG. 6 shows infarct size as a percentage of the Area At Risk (AAR);

FIG. 7 shows infarct size as a percentage of the total Left Ventricle (LV);

FIG. 8 shows infarct size as a percentage of the total Left Ventricle (LV);

FIG. 9 shows infarct size as a percentage of the Area At Risk (AAR);

FIG. 10 shows the area at risk (Aar) as a percentage of the left ventricle;

FIG. 11 shows infarct size as a percentage of the area at risk;

FIG. 12 shows the amino acid sequence of human Toll-like Receptor 2 (SEQ ID NO:1);

FIG. 13 shows the amino acid sequence of human Toll-like Receptor 2 (SEQ ID NO:2);

FIG. 14 shows the extracellular domain of human Toll-like Receptor 2 (SEQ ID NO:3);

FIG. 15 shows a second cross section of the heart following administration of a p38 inhibitor (SB239063) as a positive control;

FIG. 16 shows a second cross section of the heart following administration of PBS;

FIG. 17 shows a second cross section of the heart following administration of an antibody of the IgG isotype as a negative control;

FIG. 18 shows a second cross section of the heart following administration of the experimental anti-TLR2 antagonistic monoclonal antibody OPN-301;

FIG. 19 shows a second graph of the Area At Risk (AAR) as a percentage of the total Left Ventricle (LV);

FIG. 20 shows a second graph of infarct size as a percentage of the Area At Risk (AAR);

FIG. 21 shows a further infarct size as a percentage of the total Left Ventricle (LV);

FIG. 22 shows infarct size as a percentage of the total Left Ventricle (LV);

FIG. 23A shows a graph of the number of macrophages in a heart section from blood KO and organ KO chimeric mice after 30 minutes ischemia followed by 24 hours of reperfusion. Representative images from heart sections stained for macrophages (red cells with blue nuclei). The difference in density of cells with stained membranes;

FIG. 23B shows representative images from heart sections stained for microphages, representative images from heart sections stained for macrophages (red cells with blue nuclei). The difference in density of cells were stained membranes; and FIG. 24 shows cardiac function and geometry and baseline (t=0) and post-infarction (t=28).

DETAILED DESCRIPTION OF THE INVENTION

The present invention relates to modulator agents which are specific for Toll-like Receptor 2 (TLR2) which inhibit the biological function of TLR2 or which block the expression of TLR2 for use in preventing tissue or organ damage which results from reperfusion following ischemia.

As herein defined, Toll-like Receptor 2 may be also referred to as TLR2, TLR-2 or CD282. Typically, the Toll-like Receptor 2 is human Toll-like Receptor 2. Alternatively, the Toll-like Receptor 2 is murine Toll-like Receptor 2. In further embodiments, the Toll-like Receptor 2 is a homologue or orthologue of human TLR2 which is derived from any mammal other than a human or mouse, for example, a cow or rat. In certain further embodiments, the compound which suppresses TLR2 function is cross-reactive, in that it mediates the suppression of Toll-like Receptor 2 function in Toll-like Receptor 2 derived from different species.

The term "epitope" as used herein relates to a portion of a macromolecule which is capable of being bound by a specific binding ligand, in this case, a portion of a polypeptide, in particular Toll-like Receptor 2. Epitopes may be defined from contiguous or non-contiguous sequences of amino acid residues comprised within a polypeptide sequence. The term "contiguous epitope" defines an epitope comprised of a linear series of amino acid residues within a polypeptide which define the epitope. A "non-contiguous epitope" is an epitope that is comprised of a series of amino acid residues that are non-linear in alignment, such that the residues are spaced or grouped in a non-continuous manner along the length of a polypeptide sequence. A non-continuous epitope can be a discontinuous epitope wherein the amino acid residues are grouped into 2 linear sequences, or alternatively the non-continuous epitope can be a discontinuous scattered epitope wherein the residues which contribute to the epitope are provided in 3 or more groups of linear amino acid sequences arranged along the length of the polypeptide.

Antibodies

An "antibody" is an immunoglobulin, whether natural or partly or wholly synthetically produced. The term also covers any polypeptide, protein or peptide having a binding domain that is, or is homologous to, an antibody binding domain. These can be derived from natural sources, or they may be partly or wholly synthetically produced. Examples of antibodies are the immunoglobulin isotypes and their isotypic subclasses and fragments which comprise an antigen binding domain such as Fab, scFv, Fv, dAb, Fd, and a bi-specific antibody.

In certain embodiments, the antibody may be a camelid antibody, in particular a camelid heavy chain antibody. Further, the antibody fragment may be a domain antibody or a nanobody derived from a camelid heavy chain antibody. In certain embodiments the antibody may be a shark antibody or a shark derived antibody.

In certain embodiments, the antibody is an "isolated antibody", this meaning that the antibody is (1) free of at least some proteins with which it would normally be found, (2) is essentially free of other proteins from the same source, e.g., from the same species, (3) is expressed by a cell from a different species, or (4) does not occur in nature.

As antibodies can be modified in a number of ways, the term "antibody" should be construed as covering any binding member or substance having a binding domain with the required specificity. The antibody of the invention may be a monoclonal antibody, or a fragment, derivative, functional equivalent or homologue thereof. The term includes any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in European Patent Application Publication Number EP 0,120,694 and European Patent Application Publication Number EP 0,125,023.

The constant region of the antibody may be of any suitable immunoglobulin subtype, however it is preferred that the antibody subtype is IgG1. However, in alternative embodiments, the subtype of the antibody may be of the class IgA, IgM, IgD and IgE where a human immunoglobulin molecule is used. Such an antibody may further belong to any subclass e.g. IgG1, IgG2a, IgG2b, IgG3 and IgG4.

Fragments of a whole antibody can perform the function of antigen binding. Examples of such binding fragments are; a Fab fragment comprising of the VL, VH, CL and CH1 antibody domains; an Fv fragment consisting of the VL and VH domains of a single antibody; a F(ab')2 fragments, a bivalent fragment comprising two linked Fab fragments; a single chain Fv molecule (scFv), wherein a VH domain and a VL domain are linked by a peptide linker which allows the two domains to associate to form an antigen binding site; or a bi-specific antibody, which may be multivalent or multispecific fragments constructed by gene fusion.

A fragment of an antibody or of a polypeptide for use in the present invention, for example, a fragment of a TLR2 specific antibody, generally means a stretch of amino acid residues of at least 5 to 7 contiguous amino acids, often at least about 7 to 9 contiguous amino acids, typically at least about 9 to 13 contiguous amino acids, more preferably at least about 20 to 30 or more contiguous amino acids and most preferably at least about 30 to 40 or more consecutive amino acids.

A "derivative" of such an antibody or polypeptide, or of a fragment of a TLR2 specific antibody means an antibody or polypeptide modified by varying the amino acid sequence of the protein, e.g. by manipulation of the nucleic acid encoding the protein or by altering the protein itself. Such derivatives of the natural amino acid sequence may involve insertion, addition, deletion and/or substitution of one or more amino acids, preferably while providing a peptide having TLR2 binding activity. Preferably such derivatives involve the insertion, addition, deletion and/or substitution of 25 or fewer amino acids, more preferably of 15 or fewer, even more preferably of 10 or fewer, more preferably still of 4 or fewer and most preferably of 1 or 2 amino acids only.

In certain embodiments, humanized antibodies are also provided. Humanized antibodies may be produced, for example, by the method of Winter as described in U.S. Pat. No. 5,585,089.

A humanised antibody may be a modified antibody having the hypervariable region of a monoclonal antibody such as a TLR2 specific antibody and the constant region of a human antibody. Thus the binding member may comprise a human constant region.

The variable region other than the hypervariable region may also be derived from the variable region of a human antibody and/or may also be derived from a monoclonal antibody such as a TLR2 specific antibody. In such case, the entire variable region may be derived from murine monoclonal antibody a TLR2 specific antibody and the antibody is said to be chimerised. Methods for making chimeric antibodies are known in the art. Such methods include, for example, those described in U.S. patents by Boss (Celltech) and by Cabilly (Genentech). See U.S. Pat. Nos. 4,816,397 and 4,816,567, respectively.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, European Patent Application No 0,184,187, GB Patent Application No. 2,188,638A or European Patent Application No. 0,239,400. A hybridoma or other cell producing an antibody may be subject to genetic mutation or other changes, which may or may not alter the binding specificity of antibodies produced.

In certain embodiments, where the TLR2 inhibitory compound or the TLR2 binding compound is an antibody, or an antibody binding fragment, wherein the antibody is administered to a subject in a therapeutically effective amount. In certain embodiments, the therapeutically effective amount comprises the antibody in a range chosen from 1 µg/kg to 20 mg/kg, 1 g/kg to 10 mg/kg, 1 µg/kg to 1 mg/kg, 10 µg/kg to 1 mg/kg, 10 µg/kg to 100 pg/kg and 500 pg/kg to 1 mg/kg.

Production of Antibodies

The antibodies provided by the present invention may be provided by a number of techniques. For example, a combinatorial screening technique such as a phage display-based biopanning assay may be used to in order to identify amino acid sequences which have binding specificity to the binding epitopes of the invention. Such phage display biopanning techniques involve the use of phage display libraries, which are utilised in methods which identify suitable epitope binding ligands in a procedure which mimics immune selection, through the display of antibody binding fragments on the surface of filamentous bacteria. Phage with specific binding activity are selected. The selected phage can thereafter be used in the production of chimeric, CDR-grafted, humanised or human antibodies.

In further embodiments, the antibody is a monoclonal antibody, which may be produced using any suitable method which produces antibody molecules by continuous cell lines in culture. Suitable methods will be well known to the person skilled in the art and include, for example, the method of Kohler and Milstein (Kohler et al. Nature, 256, 495-497. 1975). Chimeric antibodies or CDR-grafted antibodies are further provided within the scope of the present invention. In certain embodiments, the antibodies of the invention may be produced by the expression of recombinant DNA in host cell.

In certain embodiments, the monoclonal antibodies may be human antibodies, produced using transgenic animals, for example, transgenic mice, which have been genetically modified to delete or suppress the expression of endogenous murine immunoglobulin genes, with loci encoding for human heavy and light chains being expressed in preference, this resulting in the production of fully human antibodies.

In certain embodiments, the binding compound is a binding fragment which is derived from an antibody, for example, an antibody binding fragment, such as a Fab, F(ab')2, Fv or a single chain Fv (scFV).

In certain embodiments, the binding compound comprises a polyclonal antibody, a chimeric antibody, a synthesized or synthetic antibody, a fusion protein or fragment thereof, or a natural or synthetic chemical compound or a peptidomimetic. Methodologies for producing antibodies which have an affinity and binding specificity for the TLR2 epitope of the present invention are described hereinbefore.

The antibodies or antibody fragments of and for use in the present invention may also be generated wholly or partly by chemical synthesis. The antibodies can be readily prepared according to well-established, standard liquid or, preferably, solid-phase peptide synthesis methods, general descriptions of which are broadly available and are well known by the person skilled in the art. Further, they may be prepared in solution, by the liquid phase method or by any combination of solid-phase, liquid phase and solution chemistry.

Another convenient way of producing antibodies or antibody fragments suitable for use in the present invention is to express nucleic acid encoding them, by use of nucleic acid in an expression system.

Nucleic acid for use in accordance with the present invention may comprise DNA or RNA and may be wholly or partially synthetic. In a preferred aspect, nucleic acid for use in the invention codes for antibodies or antibody fragments of the invention as defined above. The skilled person will be able to determine substitutions, deletions and/or additions to such nucleic acids which will still provide an antibody or antibody fragment of the present invention.

Nucleic acid sequences encoding antibodies or antibody fragments for use with the present invention can be readily prepared by the skilled person using the information and references contained herein and techniques known in the art (for example, see Sambrook et al. (1989), and Ausubel et al, (1992)), given the nucleic acid sequences and clones available. These techniques include (i) the use of the polymerase chain reaction (PCR) to amplify samples of such nucleic acid, e.g. from genomic sources, (ii) chemical synthesis, or (iii) preparing cDNA sequences. DNA encoding antibody fragments may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the sequences can be made, e.g. using site directed mutagenesis, to lead to the expression of modified peptide or to take account of codon preferences in the host cells used to express the nucleic acid.

The nucleic acid may be comprised as constructs in the form of a plasmid, vector, transcription or expression cassette which comprises at least one nucleic acid as described above. The construct may be comprised within a recombinant host cell which comprises one or more constructs as above. Expression may conveniently be achieved by culturing under appropriate conditions recombinant host cells containing the nucleic acid. Following production by expression the antibody or antibody fragments may be isolated and/or purified using any suitable technique, then used as appropriate.

Systems for cloning and expression of a polypeptide in a variety of different host cells are well known. Suitable host cells include bacteria, mammalian cells, yeast, insect and baculovirus systems. Mammalian cell lines available in the art for expression of a heterologous polypeptide include Chinese hamster ovary (CHO) cells, HeLa cells, baby hamster kidney cells, NS0 mouse myeloma cells. A common, preferred bacterial host is $E.\ coli$. The expression of antibodies and antibody fragments in prokaryotic cells such as $E.\ coli$ is well established in the art. Expression in eukaryotic cells in culture is also available to those skilled in the art as an option for production of a binding member.

General techniques for the production of antibodies are well known to the person skilled in the field, with such methods being discussed in, for example, Kohler and Milstein (1975) Nature 256: 495-497; U.S. Pat. No. 4,376,110; Harlow and Lane, Antibodies: a Laboratory Manual, (1988) Cold Spring Harbor, the contents of which are incorporated herein by reference. Techniques for the preparation of recombinant antibody molecules are described in the above references and also in, for example, EP 0,623,679 and EP 0,368,684, which are incorporated herein by reference.

In certain embodiments of the invention, recombinant nucleic acids comprising an insert coding for a heavy chain variable domain and/or for a light chain variable domain of antibodies are employed. By definition such nucleic acids comprise coding single stranded nucleic acids, double stranded nucleic acids consisting of said coding nucleic acids and of complementary nucleic acids thereto, or these complementary (single stranded) nucleic acids themselves.

Furthermore, nucleic acids encoding a heavy chain variable domain and/or a light chain variable domain of antibodies can be enzymatically or chemically synthesised nucleic acids having the authentic sequence coding for a naturally-occurring heavy chain variable domain and/or for the light chain variable domain, or a mutant thereof.

Recombinant DNA technology may be used to improve the antibodies of the invention. Thus, chimeric antibodies may be constructed in order to decrease the immunogenicity thereof in diagnostic or therapeutic applications. Moreover, immunogenicity within, for example, a transgenic organism such as a pig, may be minimised, by altering the antibodies by CDR grafting in a technique analogous to humanising antibodies. Examples of such techniques are described in EP 0,239,400 to Winter. In order to reduce immunogenicity within a recipient, the invention may employ recombinant nucleic acids comprising an insert coding for a heavy chain variable domain of an antibody fused to a human constant domain. Likewise the invention concerns recombinant DNAs comprising an insert coding for a light chain variable domain of an antibody fused to a human constant domain kappa or lambda region.

Antibodies may moreover be generated by mutagenesis of antibody genes to produce 5 artificial repertoires of antibodies. This technique allows the preparation of antibody libraries. Antibody libraries are also available commercially. Hence, the present invention advantageously employs artificial repertoires of immunoglobulins, preferably artificial scFv repertoires, as an immunoglobulin source in order to identify binding molecules which have specificity for the epitope of the present invention.

Antibody Selection Systems

Immunoglobulins which are able to bind to the epitope of the present invention and which accordingly may be used in the methods of the invention can be identified using any technique known to the skilled person. Such immunoglobulins may be conveniently isolated from libraries comprising artificial repertoires of immunoglobulin polypeptides. A "repertoire" refers to a set of molecules generated by random, semi-random or directed variation of one or more template molecules, at the nucleic acid level, in order to provide a multiplicity of binding specificities. Methods for generating repertoires are well characterised in the art.

Any library selection system may be used in conjunction with the invention. Selection protocols for isolating desired members of large libraries are known in the art, as typified by phage display techniques. Such systems, in which diverse peptide sequences are displayed on the surface of filamentous bacteriophage, have proven useful for creating libraries of antibody fragments (and the nucleotide sequences that encode them) for the in-vitro selection and amplification of specific antibody fragments that bind a target antigen. The nucleotide sequences encoding the VH and VL regions are linked to gene fragments which encode leader signals that direct them to the periplasmic space of E. coli and as a result the resultant antibody fragments are displayed on the surface of the bacteriophage, typically as fusions to bacteriophage coat proteins (for example pIII or pVIII). Alternatively, antibody fragments are displayed externally on lambda phage capsids (phage bodies). An advantage of phage-based display systems is that, because they are biological systems, selected library members can be amplified simply by growing the phage containing the selected library member in bacterial cells. Furthermore, since the nucleotide sequence that encodes the polypeptide library member is contained on a phage or phagemid vector, sequencing, expression and subsequent genetic manipulation is relatively straight forward.

Methods for the construction of bacteriophage antibody display libraries and lambda phage expression libraries are well known in the art (for example, McCafferty et al. (1990) Nature 348 552-554. One particularly advantageous approach has been the use of scFv phage-libraries (see for example Huston et al., 1988, Proc. Natl. Acad. Sci USA).

An alternative to the use of phage or other cloned libraries is to use nucleic acid, preferably RNA, derived from the B cells of an animal which has been immunised with the selected target, e.g. the TLR2 epitope of the present invention.

Isolation of V-region and C-region mRNA permits antibody fragments, such as Fab or Fv, to be expressed intracellularly. Briefly, RNA is isolated from the B cells of an immunised animal, for example from the spleen of an immunised mouse or the circulating B cells of a llama, and PCR primers used to amplify VH and VL cDNA selectively from the RNA pool. The VH and VL sequences thus obtained are joined to make scFv antibodies. PCR primer sequences may be based on published VH and VL sequences.

Peptidomimetics

Peptide analogues, such as peptidomimetics or peptide mimetics are non-peptide compounds with properties representative of a template peptide. Such peptide analogues are typically developed using computerised molecular modelling. Peptidomimetics which are structurally similar to peptides which have affinity and binding specificity to the TLR2 binding epitope of the present invention may be used to mediate similar diagnostic, prophylactic and therapeutic effects.

Peptidomimetics are typically structurally similar to a template peptide, but have one or more peptide linkages replaced by an alternative linkage, by methods which are well known in the art. For example, a peptide which has a binding specificity for the TLR2 epitope of the invention may be modified such that it comprises amide bond replacement, incorporation of non peptide moieties, or backbone cyclisation. Suitably if cysteine is present the thiol of this residue is capped to prevent damage of the free sulphate group. A peptide may further be modified from the natural sequence to protect the peptides from protease attack.

Suitably a peptide of and for use in the present invention may be further modified using at least one of C and/or N-terminal capping, and/or cysteine residue capping. Suitably, a peptide of and for use in the present invention may be capped at the N terminal residue with an acetyl group. Suitably, a peptide of and for use in the present invention may be capped at the C terminal with an amide group. Suitably, the thiol groups of cysteines are capped with acetamido methyl groups.

Expression, isolation and purification of polypeptides defining the epitope of the invention and fragments thereof may be accomplished by any suitable technique. A method for producing polypeptides comprises culturing host cells transformed with a recombinant expression vector encoding a polypeptide under conditions that promote expression of the polypeptide, then recovering the expressed polypeptides from the culture. The person skilled in the art will recognise that the procedure for purifying the expressed polypeptides will vary according to such factors as the type of host cells employed, and whether the polypeptide is intracellular, membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, avian, microbial, viral, bacterial, or insect gene. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired (E. coli) host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide during translation, but allows secretion of polypeptide from the cell.

Suitable host cells for expression of polypeptides include higher eukaryotic cells and yeast. Prokaryotic systems are also suitable. Mammalian cells, and in particular CHO cells are particularly preferred for use as host cells. Appropriate cloning and expression vectors for use with mammalian, prokaryotic, yeast, fungal and insect cellular hosts are described, for example, in Pouwels et al. Cloning Vectors: A Laboratory Manual, Elsevier, New York, (1986) (ISBN 0444904018).

Small Molecules

In various further aspects, the present invention relates to screening and assay methods for use in identifying small molecule compounds which antagonise TLR2 activity or expression. Certain further aspects extend to the compounds identified thereby, wherein said binding compounds have affinity and binding specificity for an epitope which, when bound, inhibits TLR2 functional activity.

A substance identified as an antagonist of the TLR2 receptor may be a peptide or may be non-peptide in nature, for example a peptidomimetic as described hereinbefore. However, non-peptide "small molecules" are often preferred for many in-vivo pharmaceutical uses. Accordingly, a mimetic or mimic of a TLR2 binding compound for use in the present invention may be designed for pharmaceutical uses.

The designing of mimetics to a known pharmaceutically active compound is a known approach to the development of pharmaceuticals based on a "lead" compound. This might be desirable where the active compound is difficult or expensive to synthesise, or where it is unsuitable for a particular method of administration. For example, peptides are not well suited as active agents for oral compositions and administration as they are degraded by proteases present in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, for example by substituting each amino acid residue in turn. These parts or residues constituting the active region of the compound are known as its "pharmacophore".

Once the pharmacophore has been determined, its structure is modelled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can also be used in this modelling process.

In a variant of this approach, the three-dimensional structure of the TLR2 binding compound is modelled. This can be especially useful where the ligand and/or binding partner change conformation on binding, allowing the model to take account of the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in-vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in-vivo or clinical testing.

In certain embodiments, the mimetic binding compound may be a natural or synthetic chemical compound used in drug screening programmes. Extracts of plants which contain several characterised or uncharacterised components may also be used.

In yet further aspects, the invention extends to the use of combinatorial library technology (Schultz, J S (1996) Biotechnol. Prog. 12:729-743) which provides an efficient way of testing a potentially vast number of different substances for ability their ability to bind to an epitope or to modulate the activity of a ligand which binds to an epitope. Prior to, or as well as, being screened for modulation of activity, test substances may be screened for ability to interact with the polypeptide, e.g. in a yeast two-hybrid system (which requires that both the polypeptide and the test substance can be expressed in yeast from encoding nucleic acid). This may be used as a coarse screen prior to testing a substance for actual ability to modulate activity of the polypeptide.

The amount of test substance or compound which may be added to an assay of the invention will normally be determined by trial and error depending upon the type of compound used. Typically, from about 0.01 to 100 nM concentrations of putative inhibitor compound may be used, for example from 0.1 to 10 nM. Greater concentrations may be used when a peptide is the test substance.

Combination Medicaments

As described hereinbefore, the present invention extends to combinational therapies wherein compositions or methods relates to the administration of a binding compound which inhibits the functional activity of TLR2 are administered in combination with at least one further therapeutic compound which serves to suppress the immune response that may contribute to reperfusion injury, or treat a cardiac disease.

Typically the primary and secondary therapeutic compositions are given contemporaneously. In certain embodiments, the primary therapeutic composition (i.e. the binding compound which antagonises the functional activity of TLR2) and the secondary therapeutic compounds are administered simultaneously. In certain further embodiments, they are administered sequentially.

In certain embodiments, the combination therapy may comprise a TLR2 functional inhibitor that is co-administered to a subject along with at least one of: a cytokine inhibitor (such as, but not limited to an inhibitor of IL-1, IL-6, IL-8 and IL-15), and inhibitor of tumour necrosis factor, a growth factor inhibitor, an immunosuppressor, an anti-inflammatory, an enzymatic inhibitor, a metabolic inhibitor, a cytotoxic agent or a cytostatic agent.

A person of relevant skill in the field will recognise that the administration to a subject of a combination therapy can be advantageous in that it permits administration of a lower dose of therapeutic to a subject in order to achieve and associated therapeutically effective effect. The administration of a lower combined dose also results in the subject being exposed to a lower toxicity level derived from the administered compound. Furthermore, as the secondary therapeutic compounds which are administered as part of the combination therapy provided by the invention target different pathways, there is likely to be a synergistic improvement in the overall efficacy of the therapy. An improvement in efficacy would again result in the need for a lower dose to be administered and as such an associated reduction in toxicity.

In identifying and selecting suitable secondary therapeutic compounds for administration along with the TLR2 inhibitory compounds of the present invention, said secondary therapeutic compounds may be selected on the basis of such compounds modulating the immune response at a different stage of the inflammatory response which results in inflammation associated with reperfusion injury. Such secondary compounds may include, but are not limited to; soluble receptors, peptide inhibitor compound, small molecule, fusion proteins or ligands, antibodies, and cytokines which mediate an anti-inflammatory effect.

Administration

The monoclonal antibody or fusion protein of the present invention may be administered alone but will preferably be administered as a pharmaceutical composition, which will generally comprise a suitable pharmaceutically acceptable excipient, diluent or carrier selected depending on the intended route of administration. Examples of suitable pharmaceutical carriers include; water, glycerol, ethanol and other GRAS reagents.

The monoclonal antibody or fusion protein of the present invention may be administered to a patient in need of treatment via any suitable route. As detailed herein, it is preferred that the composition is administered parenterally by injection or infusion. Examples of preferred routes for parenteral administration include, but are not limited to; intravenous, intracardial, intraarterial, intraperitoneal, intramuscular, intracavity, subcutaneous, transmucosal, inhalation or transdermal.

Routes of administration may further include topical and enteral, for example, mucosal (including pulmonary), oral, nasal, rectal.

In certain embodiments, the composition is deliverable as an injectable composition. For intravenous, intramuscular, intradermal or subcutaneous application, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection or, Lactated Ringer's injection. Preservatives, stabilisers, buffers, antioxidants and/or other additives may be included, as required.

The composition may also be administered via microspheres, liposomes, other microparticulate delivery systems or sustained release formulations placed in certain tissues including blood.

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition ISBN 0-912734-04-3 and Pharmaceutical Dosage Forms and Drug Delivery Systems; Ansel, H. C. et al. 7th Edition ISBN 0-683305-72-7, the entire disclosures of which is herein incorporated by reference.

The composition is preferably administered to an individual in a "therapeutically effective amount", this being sufficient to show benefit to the individual to whom the composition is administered. The actual dose administered, and rate and time-course of administration, will depend on, and can be determined with due reference to, the nature and severity of the condition which is being treated, as well as factors such as the age, sex and weight of the patient to be treated and the route of administration. Further due consideration should be given to the properties of the composition, for example, its binding activity and in-vivo plasma life, the concentration of the fusion protein in the formulation, as well as the route, site and rate of delivery.

Dosage regimens can include a single administration of the composition of the invention, or multiple administrative doses of the composition. The compositions can further be administered sequentially or separately with other therapeutics and medicaments which are used for the treatment of the condition for which the fusion protein of the present invention is being administered to treat.

Examples of dosage regimens which can be administered to a subject can be selected from the group comprising, but not limited to; 1 μg/kg/day through to 20 mg/kg/day, 1 μg/kg/day through to 10 mg/kg/day, 10 μg/kg/day through to 1 mg/kg/day.

The TLR2 modulator agent of the present invention is preferably administered to an individual in a "therapeutically effective amount", this being sufficient to show benefit to the individual. The actual amount administered, and rate and time-course of administration, will depend on the nature and severity of what is being treated. Prescription of treatment, e.g. decisions on dosage etc, is ultimately within the responsibility and at the discretion of general practitioners and other medical doctors, and typically takes account of the disorder to be treated, the condition of the individual patient, the site of delivery, the method of administration and other factors known to practitioners.

Unless otherwise defined, all technical and scientific terms used herein have the meaning commonly understood by a person who is skilled in the art in the field of the present invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

As used herein, terms such as "a", "an" and "the" include singular and plural referents unless the context clearly demands otherwise. Thus, for example, reference to "an active agent" or "a pharmacologically active agent" includes a single active agent as well as two or more different active agents in combination, while references to "a carrier" includes mixtures of two or more carriers as well as a single carrier, and the like.

The nomenclature used to describe the polypeptide constituents of the fusion protein of the present invention follows the conventional practice wherein the amino group (N) is presented to the left and the carboxy group to the right of each amino acid residue.

The expression "amino acid" as used herein is intended to include both natural and synthetic amino acids, and both D and L amino acids. A synthetic amino acid also encompasses chemically modified amino acids, including, but not limited to salts, and amino acid derivatives such as amides. Amino acids present within the polypeptides of the present invention can be modified by methylation, amidation, acetylation or substitution with other chemical groups which can change the circulating half life without adversely affecting their biological activity.

The terms "peptide", "polypeptide" and "protein" are used herein interchangeably to describe a series of at least two amino acids covalently linked by peptide bonds or modified peptide bonds such as isosteres. No limitation is placed on the maximum number of amino acids which may comprise a peptide or protein. Furthermore, the term polypeptide extends to fragments, analogues and derivatives of a peptide, wherein said fragment, analogue or derivative retains the same biological functional activity as the peptide from which the fragment, derivative or analogue is derived Furthermore the term "fusion protein" as used herein can also be taken to mean a fusion polypeptide, fusion peptide or the like, or may also be referred to as an immunoconjugate. The term "fusion protein" refers to a molecule in which two or more subunit molecules, typically polypeptides, are covalently or non-covalently linked.

As used herein, the term "therapeutically effective amount" means the amount of an agent, binding compound, small molecule, fusion protein or peptidomimetic of the invention which is required to suppress TLR2-mediated inflammation which is causative of reperfusion injury which result from at least one condition selected from the group comprising, but not limited to: hypoxia, stroke, heart attack, chronic kidney failure or organ transplantation in a subject.

As used herein, the term "prophylactically effective amount" relates to the amount of a composition which is required to prevent the initial onset, progression or recurrence of TLR2-mediated inflammation which is causative of reperfusion injury which result from at least one condition selected from the group comprising, but not limited to: hypoxia, stroke, heart attack, chronic kidney failure or organ transplantation in a subject.

As used herein, the term "treatment" and associated terms such as "treat" and "treating" means the reduction of the progression, severity and/or duration of a TLR2 mediated condition of at least one symptom thereof, wherein said reduction or amelioration results from the administration of a binding compound which has specificity for the TLR2 binding epitope of the present invention. The term 'treatment' therefore refers to any regimen that can benefit a subject. The treatment may be in respect of an existing condition or may be prophylactic (preventative treatment). Treatment may include curative, alleviative or prophylactic effects. References herein to "therapeutic" and "prophylactic" treatments are to be considered in their broadest context. The term "therapeutic" does not necessarily imply that a subject is treated until total recovery. Similarly, "prophylactic" does not necessarily mean that the subject will not eventually contract a disease condition.

As used herein, the term "subject" refers to an animal, preferably a mammal and in particular a human. In a particular embodiment, the subject is a mammal, in particular a human. The term "subject" is interchangeable with the term "patient" as used herein.

EXAMPLES

Example 1

Effect of TLR2 Antagonistic Antibody on Reperfusion Injury in the Heart

Materials and Methods:
(i) Animals & Experimental design.

Male C57BL6 mice (8-12 weeks old, 25-30 grams of weight) underwent 30 minutes of ischemia followed by 24 hours of reperfusion.

Experimental compounds were administered 5 minutes prior to reperfusion via the tail vein. Mice were given 400-450 µl of stock with either an antibody of the IgG isotype 10 mg/kg as a negative control (n=10), SB239063 0.5 mg/kg ((Alexis Corporation, catalogue number ALX-270-351) SB239063 is also known as trans-1-(4-Hydroxycyclohexyl)-4-(fluorophenyl)-5-(2-methoxypyrimidin-4-yl) imidazole a potent, cell permeable inhibitor of p38 MAP kinase (IC50=44 nM for recombinant purified human p38alpha) which Inhibits IL-1 and TNF-α production in LPS-stimulated human peripheral blood monocytes ($IC_{50}$=120 nM and 350 nM, respectively)) as a positive control (n=10), PBS (n=11) and experimental OPN-301 monoclonal antibody 15 mg/kg (n=6) 10 mg/kg (n=10, n=5), 10 mg/kg (n=5). OPN-301 (OPN301) is a murine IgG1 anti-TLR2 antibody (mouse Toll-like Receptor 2 (TLR2) antibody, clone T2.5, HyCult Biotechnology b.v., Cell Sciences, Canton, USA: catalogue number 1054).

Mice were anesthetized with a mixture of FENTANYL™ (N-(1-phenethyl-4-piperidyl)-N-phenyl-propanamide) 0.05 mg/kg, DORMICUM™ (Midazolum, 8-chloro-6-(2-fluorophenyl)-1-methyl-4H-imidazo[1,5-a][1,4]benzodiazepine) 5 mg/kg and DOMITOR™ (medetomidine hydrochlorine) 0.5 mg/kg (intraperitoneal injection). Atropine ((8-methyl-8-azabicyclo[3.2.1]oct-3-yl) 3-hydroxy-2-phenylpropanoate) 0.05 mg/kg was subcutaneously administered before coronary ligation. Core body temperature was maintained between 36° C. and 37.5° C. during surgery by continuous monitoring with a rectal thermometer and automatic heating blanket. Mice were incubated and ventilated (Harvard Apparatus Inc.) with 100% oxygen. The left anterior descending (LAD) coronary artery was ligated using an 8-0 vicryl suture with a section of polyethylene-10 tubing placed over the LAD.

Ischemia was confirmed by bleaching of the myocardium. Reperfusion was initiated by releasing the ligature and removing the polyethylene-10 tubing. Reperfusion of the endangered myocardium is characterized by typical hyperaemia in the first few minutes. A piece of the loosened suture was left in place in order to determine ischemic area. The chest wall was closed and the animals received subcutaneously ANTISEDAN™ (atipamezole hydrochloride, a sedation reversal agent for DOMITOR™ (medetomidine hydrochlorine)) 2.5 mg/kg, ANEXATE™ (Flumazenil (also known as flumazepil)) 0.5 mg/kg and TEMGESIC™ (buprenorphine) 0.1 mg/kg.

Infarct Size

Infarct Size (IS) is expressed as a percentage of the Area-At-Risk (AAR) and total Left Ventricle (LV). The ratio of AAR/LV is a measure for the extent of myocardial tissue that underwent ischemia and reperfusion (i.e. endangered area). The ratio IS/AAR is an accurate measurement to determine infarct size within endangered myocardium and is the primary endpoint from which the efficacy of treatment is addressed. The secondary endpoint IS/LV ratio is the percentage infarcted area within the total left ventricular wall.

To determine the AAR, the LAD was ligated once again (at the level marked by the suture left in place) and 4% Evans blue dye was injected via the thoracic aorta in a retrograde fashion. Hearts were rapidly explanted, rinsed in 0.9% saline and wrapped in a clear food wrap and frozen at −20° C. for 1 hour. Hearts were then mechanically sliced into five 1 mm cross sections. Heart sections were incubated in 1% triphenyltetrazolium chloride (Sigma-Aldrich) at 37° C. for 15 minutes before placing them in formaldehyde for another 15 minutes. Viable tissue stained red and infarcted tissue appeared white. Heart sections were digitally photographed (CANON EOS 400D) under a microscope (CARL ZEISS™). IS, MR and total LV area were measured using ImageJ software (version 1.34).

Statistical Analysis

All data are expressed as Mean±SD. After skewness±SD and kurtosis±SD confirmed normality, a one-way ANOVA with Bonferroni adjustment (Table 2) and a Dunnett's T test (2 sided) (Table 4). was used to test differences between groups. Kolmogorov-Smirnov test performed if abnormal distribution was suspected (i.e. when kurtosis and skewness values are twice their standard deviations). All statistical analyses were performed using SPSS version 13.0 for Windows (SPSS, Chicago, USA) and $p<0.05$ was considered significant.

Results

Survival—All animals survived 30 minutes of ischemia followed by 24 hours of reperfusion.

Cross sections of the heart—FIGS. 1 to 4 show representative examples of cross sections of the heart in the different groups.

Descriptive Statistics—Table 1, Table 3 and FIGS. 5, 6, 7, 8 and 9 show the data and their distributions. All data are normally distributed. The p38 inhibitor group was suspected for abnormal distribution, but the Kolmogorov-Smirnov test showed its normality (p=0.077).

Area At Risk (AAR) within total Left Ventricle—The AAR/LV did not statistically differ amongst the groups, meaning that the left ventricle was equally affected by the operation between the groups (FIG. 5).

Infarct Size—Table 2 and Table 4 shows comparison of means between the experimental groups. The mAb is the only group which shows significant differences in mean IS/AAR compared to the other groups. Treatment with the OPN-301 monoclonal antibody results in a reduction of infarct size within the AAR (IS/AAR) of 43% compared to both IgG isotype (p=0.007) and p38 inhibitor treated mice (p=0.006). The reduction of IS/AAR is even more pronounced compared to PBS treated mice, 50% (p<0.001) (FIG. 6).

Infarct size as a percentage of the total Left Ventricle (IS/LV) is also reduced in the experimental anti-TLR2 OPN-301 monoclonal antibody treated mice: 53% reduction compared to IgG isotype (p=0.01), 49% reduction compared to p38 inhibitor (p=0.032) and 65% reduction compared to PBS (p<0.001) treated mice (FIG. 7).

The difference in mean IS/LV between the p38 inhibitor and IgG isotype treated mice and PBS treated mice (resp. −26% and −31%) were not statistically significant (FIG. 7).

TABLE 1

Descriptive Statistics of Dependent Variables

| | Group | N | Mean | Std. Deviation | Kurtosis | Std. Error of Kurtosis | Skewness | Std. Error of Skewness |
|---|---|---|---|---|---|---|---|---|
| AAR_LV | IgG isotype | 10 | 42.4650 | 9.68402 | −.700 | 1.334 | .836 | .687 |
| | p38 inhibitor | 10 | 40.3380 | 11.83944 | 6.996 | 1.334 | 2.559 | .687 |
| | PBS | 11 | 46.8518 | 10.25579 | .135 | 1.279 | −.607 | .661 |
| | exp. mAB | 10 | 36.7580 | 10.17614 | 2.510 | 1.334 | .792 | .687 |
| | Total | 41 | 41.7312 | 10.78184 | .446 | .724 | .750 | .369 |
| IS_AAR | IgG isotype | 10 | 31.1460 | 8.87645 | −.854 | 1.334 | −.906 | .687 |
| | p38 inhibitor | 10 | 31.4000 | 7.53476 | 2.766 | 1.334 | −.868 | .687 |
| | PBS | 11 | 35.5845 | 9.74227 | −.738 | 1.279 | −.418 | .661 |
| | exp. mAB | 10 | 17.8940 | 7.32916 | −1.163 | 1.334 | .454 | .687 |
| | Total | 41 | 29.1666 | 10.56588 | −.835 | .724 | −.240 | .369 |
| IS_LV | IgG isotype | 10 | 12.8620 | 3.50649 | .877 | 1.334 | −.388 | .687 |
| | p38 inhibitor | 10 | 12.0100 | 2.36137 | 1.693 | 1.334 | 1.265 | .687 |
| | PBS | 11 | 17.3100 | 7.41934 | −1.614 | 1.279 | −.101 | .661 |
| | exp. mAB | 10 | 6.1020 | 1.67206 | .617 | 1.334 | .023 | .687 |
| | Total | 41 | 12.1988 | 5.91672 | .388 | .724 | .893 | .389 |

TABLE 2

One-way ANOVA Post hoc test With Bonferroni adjustment for multiple comparisons.

| Bonferroni Dependent Variable | (I) Group | (J) Group | Mean Difference (I-J) | Std. Error | Sign. | 95% Confidence interval Lower Bound | 95% Confidence interval Upper Bound |
|---|---|---|---|---|---|---|---|
| AAR_LV | IgG isotype | p38 inhibitor | 2.12700 | 4.70156 | 1.000 | −10.9791 | 15.2331 |
| | | PBS | −4.38682 | 4.59347 | 1.000 | −17.1916 | 8.4179 |
| | | exp. mAB | 5.70700 | 4.70156 | 1.000 | −7.3991 | 18.8131 |
| | p38 inhibitor | IgG isotype | −2.12700 | 4.70156 | 1.000 | −15.2331 | 10.9791 |
| | | PBS | −6.51382 | 4.59347 | .987 | −19.3186 | 6.2909 |
| | | exp. mAB | 3.58000 | 4.70156 | 1.000 | −9.5261 | 16.6861 |
| | PBS | IgG isotype | 4.38682 | 4.59347 | 1.000 | −8.4179 | 17.1916 |
| | | p38 inhibitor | 6.51382 | 4.59347 | .987 | −6.2909 | 19.3186 |
| | | exp. mAB | 10.09382 | 4.59347 | .206 | −2.7109 | 22.8986 |
| | exp. mAB | IgG isotype | −5.70700 | 4.70156 | 1.000 | −18.8131 | 7.3991 |
| | | p38 inhibitor | −3.58000 | 4.70156 | 1.000 | −16.6861 | 9.5261 |
| | | PBS | −10.09382 | 4.59347 | .206 | −22.8986 | 2.7109 |
| IS_AAR | IgG isotype | p38 inhibitor | −.25400 | 3.78664 | 1.000 | −10.8096 | 10.3016 |
| | | PBS | −4.43855 | 3.69957 | 1.000 | −14.7515 | 5.8744 |
| | | exp. mAB | 13.25200(*) | 3.78664 | .007 | 2.6964 | 23.8076 |
| | p38 inhibitor | IgG isotype | .25400 | 3.78664 | 1.000 | −10.3016 | 10.8096 |
| | | PBS | −4.18455 | 3.69957 | 1.000 | −14.4975 | 6.1284 |
| | | exp. mAB | 13.50600(*) | 3.78664 | .006 | 2.9504 | 24.0616 |
| | PBS | IgG isotype | 4.43855 | 3.69957 | 1.000 | −5.8744 | 14.7515 |
| | | p38 inhibitor | 4.18455 | 3.69957 | 1.000 | −6.1284 | 14.4975 |
| | | exp. mAB | 17.69055(*) | 3.69957 | .000 | 7.3776 | 28.0035 |

TABLE 2-continued

One-way ANOVA Post hoc test With Bonferroni adjustment for multiple comparisons.

| Bonferroni | | | Mean | | | 95% Confidence interval | |
|---|---|---|---|---|---|---|---|
| Dependent Variable | (I) Group | (J) Group | Difference (I-J) | Std. Error | Sign. | Lower Bound | Upper Bound |
| | exp. mAB | IgG isotype | −13.25200(*) | 3.78664 | .007 | −23.8076 | −2.6964 |
| | | p38 inhibitor | −13.50600(*) | 3.78664 | .006 | −24.0616 | −2.9504 |
| | | PBS | −17.69055(*) | 3.69957 | .000 | −28.0035 | −7.3776 |
| IS_LV | IgG isotype | p38 inhibitor | .85200 | 1.99523 | 1.000 | −4.7099 | 6.4139 |
| | | PBS | −4.44800 | 1.94935 | .170 | −9.8820 | .9860 |
| | | exp. mAB | 6.76000(*) | 1.99523 | .010 | 1.1981 | 12.3219 |
| | p38 inhibitor | IgG isotype | −.85200 | 1.99523 | 1.000 | −6.4139 | 4.7099 |
| | | PBS | −5.30000 | 1.94935 | .059 | −10.7340 | .1340 |
| | | exp. mAB | 5.90800(*) | 1.99523 | .032 | .3461 | 11.4699 |
| | PBS | IgG isotype | 4.44800 | 1.94935 | .170 | −.9860 | 9.8820 |
| | | p38 inhibitor | 5.30000 | 1.94935 | .059 | −.1340 | 10.7340 |
| | | exp. mAB | 11.20800(*) | 1.94935 | .000 | 5.7740 | 16.6420 |
| | exp. mAB | IgG isotype | −6.76000(*) | 1.99523 | .010 | −12.3219 | −1.1981 |
| | | p38 inhibitor | −5.90800(*) | 1.99523 | .032 | −11.4699 | −.3461 |
| | | PBS | −11.20800(*) | 1.94935 | .000 | −16.6420 | −5.7740 |

*The mean difference is significant at the .05 level.

TABLE 3

Descriptive statistics of dependent variables (amended table to include IS/LV data and TLR2KO, Blood KO an Organ KO data not previously included in table 3)

| | Group | N | Mean | Std. Error of Mean | Kurtosis | Std. Error of Kurtosis | Skewness | Std. Error of Skewness |
|---|---|---|---|---|---|---|---|---|
| AAR/LV | Saline | 10 | 40.7550 | 3.72254 | 2.342 | 1.334 | −1.361 | .687 |
| | p38 inhibitor | 10 | 40.8740 | 3.75393 | 6.945 | 1.334 | 2.526 | .687 |
| | IgG isotype | 10 | 44.0190 | 2.99674 | −.421 | 1.334 | .954 | .687 |
| | OPN-301 | 10 | 38.0840 | 3.18762 | 2.583 | 1.334 | .856 | .687 |
| | TLR2 KO | 10 | 41.4090 | 5.72911 | −.113 | 1.334 | 1.020 | .687 |
| | Blood KO | 11 | 40.6355 | 1.46900 | −.349 | 1.279 | −.035 | .661 |
| | Organ KO | 9 | 41.6533 | 2.63617 | 3.751 | 1.400 | 1.196 | .717 |
| IS/AAR | Saline | 10 | 34.5010 | 3.25153 | −1.895 | 1.334 | −.201 | .687 |
| | p38 inhibitor | 10 | 31.7250 | 2.39083 | 2.860 | 1.334 | −.922 | .687 |
| | IgG isotype | 10 | 31.4300 | 2.72385 | −.762 | 1.334 | −.921 | .687 |
| | OPN-301 | 10 | 18.9490 | 2.16521 | −.800 | 1.334 | .420 | .687 |
| | TLR2 KO | 10 | 23.0090 | 2.92849 | −.755 | 1.334 | .647 | .687 |
| | Blood KO | 11 | 22.9055 | 2.74268 | −.628 | 1.279 | .278 | .661 |
| | Organ KO | 9 | 33.9011 | 3.23683 | −1.309 | 1.400 | .411 | .717 |
| IS/LV | Saline | 10 | 14.0620 | 2.00624 | −1.153 | 1.334 | .659 | .687 |
| | p38 inhibitor | 10 | 12.3220 | .76883 | .882 | 1.334 | .999 | .687 |
| | IgG isotype | 10 | 13.5420 | 1.16046 | .889 | 1.334 | −.485 | .687 |
| | OPN-301 | 10 | 6.8170 | .55525 | .382 | 1.334 | −.418 | .687 |
| | TLR2KO | 10 | 8.7470 | .99411 | −1.124 | 1.334 | .000 | .687 |
| | Blood KO | 11 | 9.0845 | .93461 | −.907 | 1.279 | −.110 | .661 |
| | Organ KO | 9 | 13.7856 | 1.12967 | −.869 | 1.400 | .242 | .717 |

TABLE 4

Multiple Comparisons

| Dunnett t (2-sided) | | | Mean | | | 95% Confidence Interval | |
|---|---|---|---|---|---|---|---|
| Dependent Variable | (I) Group | (J) Group | Difference (I-J) | Std. Error | Sig. | Upper Bound | Lower Bound |
| AAR_LV | pos. control | Saline | .11900 | 5.30600 | 1.000 | −14.2877 | 14.5257 |
| | neg. control | Saline | 3.26400 | 5.30600 | .989 | −11.1427 | 17.6707 |
| | exp. mAB | Saline | −2.67100 | 5.30600 | .996 | −17.0777 | 11.7357 |
| | TLR2 KO | Saline | .65400 | 5.30600 | 1.000 | −13.7527 | 15.0667 |
| | 10 mg/kg | Saline | −4.36100 | 6.49850 | .982 | −22.0055 | 13.2835 |
| | 5 mg/kg | Saline | −1.58333 | 6.12685 | 1.000 | −18.2187 | 15.0521 |
| | 15 mg/kg | Saline | −5.66300 | 6.49850 | .931 | −23.3075 | 11.9815 |
| IS_AAR | pos. control | Saline | −2.77600 | 3.72697 | .968 | −12.8953 | 7.3433 |
| | neg. control | Saline | −3.07100 | 3.72697 | .947 | −13.1903 | 7.0483 |

TABLE 4-continued

Multiple Comparisons

| Dependent Variable | (I) Group | (J) Group | Mean Difference (I-J) | Std. Error | Sig. | 95% Confidence Interval Upper Bound | Lower Bound |
|---|---|---|---|---|---|---|---|
| | exp. mAB | Saline | −15.55200(*) | 3.72697 | .001 | −25.6713 | −5.4327 |
| | TLR2 KO | Saline | −11.49200(*) | 3.72697 | .019 | −21.6113 | −1.3727 |
| | 10 mg/kg | Saline | −13.72900(*) | 4.56459 | .023 | −26.1226 | −1.3354 |
| | 5 mg/kg | Saline | −9.74100 | 4.30353 | .142 | −25.4258 | 1.9438 |
| | 15 mg/kg | Saline | −13.71900(*) | 4.56456 | .024 | −26.1126 | −1.3254 |

*The mean difference is significant at the .05 level.
a Dunnett t-tests treat one group as a control, and compare all other groups against it.

It is shown that the experimental OPN-301 monoclonal antibody which has binding specificity for TLR 2 results in remarkable reduction of infarct size.

The experimental compounds were administered 5 minutes prior to reperfusion. This could explain why the positive control (SB239063) did not reduce infarct size. In studies in which the positive control was shown to be effective, a p38 inhibitor (either SB239063 or SB203580) was administered before ischemia and/or during reperfusion. In clinical settings this protocol is not possible for several reasons. Firstly, myocardial infarctions are unpredictable, thus a patient cannot take a p38 inhibitor before the ischemic period. It is likely that p38 inhibitors need a long time to exert their action, since they were also given the entire ischemic period. This makes it unsuitable as a therapy for myocardial ischemia/reperfusion, in which early restoration of blood flow is beneficial for the patient: the drug would not have enough time to be effective. The anti-TLR2 monoclonal antibody OPN-301 was able to reduce infarct size, even under these circumstances.

There was a trend towards an effect of the p38 inhibitor SB239063 in reducing infarct size as a percentage of the total Left Ventricle (IS/LV) (p=0.059, Table 2). This may be caused by a) the spread of the data in the PBS group; b) SB239063 does have a slight effect, but not as much when given before the ischemic period as in previous studies or c) variability in responsiveness among animals to SB239063.

FIG. 9 indicates that administration of 15 mg/kg, 10 mg/kg and 5 mg/kg of the anti-TLR2 monoclonal antibody OPN-301 results in 21%, 21% and 25% infarction of the area at risk respectively, compared to 34.5% in the saline group. The administration of 10 mg/kg at n=5 is statistically similar to the results obtained in FIG. 6 (19% infarction with OPN-301 monoclonal antibody). However, the difference in infarct size between the 5 mg/kg and the saline group did not reach statistical significance (p=0.131).

In summary, 5 mg/kg of murine IgG1 anti-TLR2 antibody OPN-301 did not significantly reduce infarct size compared to a dose of 10 mg/kg or 15 mg/kg of murine IgG1 anti-TLR2 antibody OPN-301. The effect of 15 mg/kg of murine IgG1 anti-TLR2 antibody OPN-301 indicates a potent efficacy of the antibody since a relatively low number of mice i.e. n=5 compared to n=10 for 10 mg/kg, was enough to obtain normally distributed data with equal size of standard deviations. Thus, 15 mg/kg of of murine IgG1 anti-TLR2 antibody OPN-301 is equally as effective as 10 mg/kg of of murine IgG1 anti-TLR2 antibody OPN-301.

Example 2

Further Investigations into the Effect of TLR2 Antagonistic Antibody on Reperfusion Injury in the Heart The experiments of example 1 were repeated., as shown below and further as represented in FIGS. 15 to 23.

Survival.

All animals survived 30 minutes of ischemia/24 hours of reperfusion. With the exception of 2 mice treated With IgG isotype, all animals also survived 28 days after MI/R injury. The cause of death was not related to procedural and/or infectious causes.

Cross sections of the Heart

FIGS. 15, 16, 17 and 18 show representative examples of cross sections of the heart in the different groups.

Descriptive Statistics.

Table 5 and FIGS. 19, 20 and 21 shows the data and their distributions. All data are normally distributed. The p38 inhibitor group was suspected for abnormal distribution, but the Kolmogorov-Smirnov test showed its normality (p=0.077).

Area At Risk within Total Left Ventricle.

The AAR/LV did not differ among the groups, meaning that the left ventricle was equally affected by the operation between the groups (FIG. 1).

Infarct Size.

Table 5 shows multiple comparisons to PBS treatment. TLR2 knock out and murine IgG1 anti-TLR2 antibody OPN-301 treatment results in significant infarct size reduction. Treatment with the murine IgG1 anti-TLR2 antibody OPN-301 reduces infarct size within the AAR (IS/AAR) with 45% (p=0.001). TLR2 knock out (KO) mice show a reduction of 33.3% (p=0.025). The intended positive control p38 inhibitor treated mice show no reduction of infarct size (p=0.956). (FIG. 20).

The infarct size as a percentage of the total Left Ventricle (IS/LV) is also reduced in OPN-301 treated mice: 52% reduction compared to saline treatment (p<0.001). Again, no difference in infarct size was observed with the IgG isotype and p38 inhibitor treatment (FIG. 21).

Mice lacking TLR2 on solely circulating cells benefit from a similar degree of cardioprotection as the total knock-out. Infarct size in blood knock outs is similar to total TLR2 knock out mice (33.3% reduction of infarction within the AAR; p=0.019). In contrary, mice lacking TLR2 on parenchymal cells are not protected against MIR injury (FIG. 22). In concordance with our hypothesis that TLR2 mediates the inflammatory response in MI/R injury, Blood knock out mice show 2.5 fold less macrophage influx in the myocardium after 24 hours of reperfusion (p=0.0005; FIG. 23). These data support the notion that TLR2 expression on circulating cells mediates MIR injury.

Cardiac Function & Geometry.

FIG. 24 and Table 6 shows changes in cardiac function and geometry after 28 days post-infarction. Both end diastolic and end systolic volumes increase with saline and IgG isotype treatment, while OPN-301 treatment results in a decrease of both parameters. In addition, ejection fraction worsens in mice treated with saline and IgG isotype. In contrary, the murine IgG1 anti-TLR2 antibody OPN-301 preserves cardiac function after 28 days post-infarction as demonstrated by a slight increase in ejection fraction. These data suggest that the infarct size reduction with OPN-301 treatment translates into preserved heart function as well as cardiac geometry after MI/R injury.

Example 3

Inhibition of TLR2 Activity in Porcine Blood Samples

Pig blood samples will be provided (n=4-5), in heparinized tubes, with the samples being stored at room temperature. The inhibitory potential of the OPN-301 monoclonal antibody to antagonise TLR2 function will be determined. TLR-2/TLR-4 inhibitory peptides and TLR-4 inhibitory peptides will also be assessed following stimulation of purified pig PBMC with defined TLR agonists.

Experimental Protocol

Pig PBMC will be stimulated with TLR-2 agonists Pam3CSK4 and FSL-1 or TLR-4 agonist LPS in the presence or absence of a dose range of murine IgG1 anti-TLR2 antibody OPN-301 (1000-0.01 ng/ml) or TLR blocking peptides. Cells will be stimulated for 6 and 24 hours and supernatants tested for the presence of TNF-alpha.

TABLE 5

Multiple comparisons of areas at risk and infarct size.

| Dependent Variable | Dunnett t (2-sided) (I) Group | (J) Group | Mean Difference (I-J) | Std. Error | Sig. | 95% Confidence Interval Upper Bound | Lower Bound |
|---|---|---|---|---|---|---|---|
| AAR_LV | p38 inhibitor | Saline | .11900 | 5.01741 | 1.000 | −13.1178 | 13.3558 |
|  | IgG isotype | Saline | 3.26400 | 5.01741 | .969 | −9.9728 | 16.5008 |
|  | OPN-301 | Saline | −2.67100 | 5.01741 | .988 | −15.9078 | 10.5658 |
|  | TLR2 KO | Saline | .65400 | 5.01741 | 1.000 | −12.5828 | 13.8908 |
|  | Blood KO | Saline | −.11955 | 4.90205 | 1.000 | −13.0520 | 12.8129 |
|  | Organ KO | Saline | .89833 | 5.15490 | 1.000 | −12.7012 | 14.4978 |
| IS_AAR | p38 inhibitor | Saline | −2.77600 | 3.94779 | .956 | −13.1910 | 7.6390 |
|  | IgG isotype | Saline | −3.07100 | 3.94779 | .931 | −13.4860 | 7.3440 |
|  | OPN-301 | Saline | −15.55200(*) | 3.94779 | .001 | −25.9670 | −5.1370 |
|  | TLR2 KO | Saline | −11.49200(*) | 3.94779 | .025 | −21.9070 | −1.0770 |
|  | Blood KO | Saline | −11.59555(*) | 3.85703 | .019 | −21.7710 | −1.4200 |
|  | Organ KO | Saline | −.59989 | 4.05597 | 1.000 | −11.3002 | 10.1005 |
| IS_LV | p38 inhibitor | Saline | −1.74000 | 1.63426 | .780 | −6.0515 | 2.5715 |
|  | IgG isotype | Saline | −.52000 | 1.63426 | .999 | −4.8315 | 3.7915 |
|  | OPN-301 | Saline | −7.24500(*) | 1.63426 | .000 | −11.5565 | −2.9335 |
|  | TLR2 KO | Saline | −5.31500(*) | 1.63426 | .010 | −9.6265 | −1.0035 |
|  | Blood KO | Saline | −4.97745(*) | 1.59669 | .014 | −9.1898 | −.7651 |
|  | Organ KO | Saline | −.27644 | 1.67904 | 1.000 | −4.7061 | 4.1532 |

*The mean difference is significant at the .05 level.
a Dunnett t-tests treat one group as a control, and compare all other groups against it.

TABLE 6

Cardiac function & geometry at baseline (t = 0) and post-infarction (t = 28)

|  | EDV, µl | | | ESV, µl | | | EF, % | | |
|---|---|---|---|---|---|---|---|---|---|
|  | Baseline | Post-infarction | ΔEDV, % | Baseline | Post-infarction | ΔESV, % | Baseline | Post-infarction | ΔEF, % |
| Saline | 68.4 ± 3.4 | 76.8 ± 3.5 | 13.9 ± 6.9 | 39.7 ± 3.5 | 46.4 ± 3.1 | 22.8 ± 12.3 | 42.6 ± 2.1 | 39.9 ± 2.2 | −3.8 ± 9.2 |
| OPN301 | 70.05 ± 3.09 | 68.2 ± 2.5 | −1.9 ± 4.2† | 38.0 ± 2.5 | 33.7 ± 2.5 | −10.9 ± 5.0† | 45.8 ± 2.4 | 51.0 ± 2.1 | 12.6 ± 5.0† |
| IgG isotype | 59.97 ± 5.9 | 72.1 ± 6.1 | 22.4 ± 9.8$^{NS}$ | 27.9 ± 4.6 | 38.7 ± 6.4 | 43.0 ± 21.4$^{NS}$ | 55.0 ± 3.9 | 48.3 ± 6.2 | −13.1 ± 7.3$^{NS}$ |
| Sham | 63.4 ± 3.9 | 63.0 ± 3.5 | 0.6 ± 5.5 | 29.6 ± 2.2 | 29.6 ± 3.3 | 2.0 ± 11.8 | 53.6 ± 1.2 | 54.0 ± 2.8 | 1.0 ± 5.3 |

Functional outcomes were compared to saline treatment.
†p < 0.05; significant difference compared to saline treatment;
NS: no significant difference compared to saline treatment.

Significant differences can exist between strains of pig, i.e. in thrombosis studies mini-pigs may not respond to murine IgG1 anti-TLR2 antibody OPN-301, whereas other strains of pig may do.

The murine IgG1 anti-TLR2 antibody OPN-301 showed little or no inhibition of TLR2 ligand induced TNF-alpha production in PBMC's from rats or rhesus monkeys. However, results in cynomolgus monkey PBMC's were inconsistent in the first study conducted reference, so further work was conducted with cynomolgus PBMC's.

These additional studies did show that murine IgG1 anti-TLR2 antibody OPN-301 binds to TLR2 on cynomolgus monkey monocytes (by FACS analysis), with poor expression of TLR2 being observed on monkey lymphocytes. In addition, very weak or no inhibition of TLR2 ligand-induced TNF-alpha production was observed in cynomolgus money PBMC's at concentration up to 2000 ng/ml. Therefore, there appears to be rather weak cross reactivity of murine IgG1 anti-TLR2 antibody OPN-301 in the cynomolgus monkey, and the low activity seen in potency assays in PBMC's from this species indicate very low biological activity compared to human and mouse preparations.

As mice are not the usual species for conducting safety studies, the murine IgG1 anti-TLR2 antibody OPN-301 will require a more extensive toxicology programme to satisfy regulatory authorities. Acute conditions such as ischemia in pigs and safety studies are more relevant to the human condition due to similar organ size and metabolism. Therefore, the present experimentation establishes that the murine IgG1 anti-TLR2 antibody OPN-301 is a suitable therapeutic agent for use in a porcine model of ischemia reperfusion injury and possible future toxicology studies.

Example 4

Inhibition of TLR2 Activity in Rabbit

Rabbit PBMC will be stimulated with TLR-2 agonists Pam3CSK4 and FSL-1 or TLR-4 agonist LPS in the presence or absence of a dose range of the murine IgG1 anti-TLR2 antibody OPN-301 (1000-0.01 ng/ml) or TLR blocking peptides. Cells will be stimulated for 6 and 24 hours and supernatants tested for the presence of TNF-alpha.

This experiment will establish whether the murine IgG1 anti-TLR2 antibody OPN-301 is a suitable therapeutic agents for use in a rabbit model of arteriogenesis.

Mice can be used for these studies but rabbits are considered a more relevant model for the disease condition in humans. However, in order for rabbit arteriogenesis to be performed the antibody or peptides must be showed in vitro to be capable of blocking TLR agonist mediated inflammatory responses from rabbit PBMC.

Example 5

Ischemia Murine Mechanistic Studies

Previous experiments have demonstrated a therapeutic effect of the murine IgG1 anti-TLR2 antibody OPN-301 in murine ischemia reperfusion injury. A study that more fully determines the mechanism of action of the murine IgG1 anti-TLR2 antibody OPN-301 would be beneficial. The same protocol as the previous ischemia studies conducted in mice will be used but other parameters such as immunohistochemistry, inflammation, neutrophils, cytokines, apoptosis and matrix turnover will be examined.

This experimentation will establish the mechanism of action of the therapeutic murine IgG1 anti-TLR2 antibody OPN-301 on the immune system. Furthermore, chimeric mice studies will be used which will establish the best route of drug administration. TLR2 knockout mice with blood from wilf type mice will be compared with TLR2 knockout mice with wild type hearts to establish whether the antibody/peptides are having their therapeutic effects by acting on immune cells in the blood (infiltrating monocytes etc) or on heart epithelial cells. The outcome of these studies will determine whether an intravenous (i.v.) or intracoronary route of administration of the therapeutic compounds of the invention is optimal.

Example 6

Double Intervention Study

Ischemia reperfusion will be assessed using a combination of TLR-2 and

TLR4 inhibitors. This will be performed in pigs providing that murine IgG1 anti-TLR2 antibody OPN-301 demonstrates functionality in this animal model. Studies previously conducted have clearly demonstrated a role for TLR4 in heart ischemic inflammatory responses. Given that the previous studies conducted with murine IgG1 anti-TLR2 antibody OPN-301 have demonstrated a therapeutic effect of blocking TLR2 a combined therapeutic approach may be of further benefit.

Example 7

Effect of TLR-2 Blocking on Atherosclerosis

Experimentation will assess whether murine IgG1 anti-TLR2 antibody OPN-301 has a therapeutic effect in specific mouse model (ApoE–/– cuff model). One of the first steps in the series of events underlying atherosclerotic plaque formation is the recruitment of monocytes to the site of vascular damage. Of the ten members of the TLR-family, the expression of TLR1, TLR2, and TLR4 is markedly enhanced in human atherosclerotic plaques. Recently, it has been observed that TLR4 and TLR2 ligation accelerates neointima formation in arteries of mice. Furthermore, enhanced TLR2 expression has been shown to destabilize plaques. Therefore, this experimentation will examine the therapeutic potential of OPN-301 and TLR blocking peptides in reducing plaque size and formation and assess plaque stability in a mouse model of atherosclerosis.

Example 8

Stent Coated with TLR2 Antagonistic Compound

Following stenting, an inflammatory response is typical mounted by the immune system of the subject who has been implanted with the stent to the stent. Typically arterial occlusion will result as a result of this inflammatory immune response. These experiment will examine the therapeutic potential of a novel treatment regime wherein a stent is coated with murine IgG1 anti-TLR2 antibody OPN-301 or similar TLR blocking peptides. The advantage to this approach is that it will provide an acutely high local to the local site of inflammation and prevent neointima formation and possibly stabilize other plaques further downstream.

Example 9

Effect of anti-TLR2 Monoclonal Antibody Treatment on Infarct Size

This example considers the mechanisms by which the anti-TLR2 monoclonal antibody OPN-301 is effective in reducing infarct size in mice. The experimentation will consider markers for inflammation, the extent of apoptosis and the activation of survival pathways.

Chimeric mice experiments will evaluate whether local or systemic Toll-like receptor inhibition is more effective in reducing infarct size. Control and experimental groups of mice will be evaluated for the above mentioned purposes, after 1, 24 and 72 hours of reperfusion. Finally, heart function prior to and 28 days following treatment is evaluated.

The experimental monoclonal antibody against Toll-like receptor 2 (TLR2) significantly reduces infarct size in mice after 30 minutes of ischemia followed by 24 hours of reperfusion. Toll-like Receptors initiate an inflammatory cascade upon activation; release of cytokine and other pro-inflammatory chemo-attractant factors, activation of neutrophils and macrophages. Cross-talk between TLRs and pro-survival pathway PI3K/Akt has also been described.

Since Toll-like Receptors are expressed on both circulating (inflammatory) and resident (organ-specific) cells, those responsible for the detrimental effects in I/R injury remain to be addressed. This question is also important from a clinical perspective, since Toll-like Receptor inhibition can occur systemically and locally. Systemic administration of anti-TLR2 OPN-301 will inhibit both circulating and resident cells, but will require more compound. Locally (i.e. intracoronary) injection of monoclonal antibody inhibits mainly TLRs on coronary endothelial cells and cardiomyocytes and requires less compound.

The objective of this study is to clarify the underlying processes of infarct size reduction with OPN-301 administration. Control and experimental groups will be studied for differences in inflammatory activity, apoptosis and survival pathway activation. Mice hearts are explanted for immunohistochemistry and cytokine analysis at two time points to study time-dependent biochemical processes. Chimeric mice experiments will address the relative contribution of TLR 2 expression by parenchymal or circulating cell to myocardial reperfusion injury. Furthermore, we will address the impact on cardiac function of the anti-TLR monoclonal antibody OPN-301 treatment using magnetic resonance imaging (MRI) technology.

Materials and Methods

Groups of six mice per group were administered 10 mg/kg of isotype control or experimental anti-TLR2 OPN-301 monoclonal antibody (mAb) via the tail vein 5 minutes prior to reperfusion.

The treatment groups were as follows:

| Group | Treatment |
|---|---|
| 1. Vehicle Control | PBS |
| 2. Experimental mAb | 10 mg/kg OPN 301 |
| 3. Negative Control | 10 mg/kg IgG isotype |
| 4. Sham operated | PBS |
| 5. Chimera-systemic | 10 mg/kg OPN 301 |
| 6. Chimera-heart | 10 mg/kg OPN 301 |

Mice were sacrificed 1, 24 and 72 hours post-reperfusion for immunohistochemical, cytokine and chemokine analyses. Heart function is assessed before and after myocardial ischemia/reperfusion injury in saline treated, OPN-301 anti-TLR monoclonal antibody treated and sham operated mice.

Procedure for Ischemia Reperfusion in Mice

C57/BL6 mice (25 to 30 g) were subjected to 30 minutes of myocardial ischemia and 24 hours of reperfusion or sham operation. Briefly, mice were anesthetized with a mixture of Fentanyl-Dormicum-Domitor (as previously described). Additional doses were given as needed to maintain anesthesia. Mice were intubated and ventilated with 100% oxygen. Ischemia was achieved by ligating the left coronary artery (LCA) using an 8-0 silk suture with a section of PE-10 tubing placed over the LCA, 1 mm from the tip of the normally positioned left atrium. After occlusion for 30 minutes, reperfusion was initiated by releasing the ligature and removing the PE-10 tubing. In sham operated mice, the silk suture was placed without ligating the LCA.

Mice are kept under anaesthesia during the reperfusion phase for 1 hour. Hereafter, the heart was explanted and quickly rinsed in saline. The heart was cut into 2 halves through the infarcted area: one half was embedded in paraffin for immunohistochemical analysis. The infracted area and the remote area of the other half was separated again and stored in liquid nitrogen for protein/RNA/cDNA isolation.

In mice surviving for 24 and 72 hours, the chest wall was closed after releasing the ligature, the animal was extubated and body temperature maintained by use of a 37° C. warm plate. The above mentioned termination procedure was repeated in these animals after 24 and 72 hours of survival.

Immunohistochemistry Analysis

For immunohistochemistry analysis, hearts were fixed in 4% formol saline overnight and embedded in paraffin. 4 µm sections were cut and stained with hematoxylin and eosin to assess morphology and evidence of injury. Immuno-histological stains included; anti-mouse MAC-3 (#550292, Pharmingen, Clone M3/84, Rat anti-mouse IgG1), CD45 antibody (#550539, Pharmingen, Clone 30-F11, Rat anti-mouse IgG2b) and neutrophil-specific marker GR-1 (#Ab34345, Abcam, Clone 7/4, Rat anti-mouse IgG2a). Appropriate stand alone secondary antibodies were used to detect positive binding. The specificity of the primary antibodies was checked by using species and isotype-matched antibodies.

Nuclear oxidative stress was assessed using an immunostain specific for 8-hydroxy-2'-deoxyguanosine (8-OHdG), a product of oxidative stress to DNA. Tissue sections were incubated with 10% normal horse serum for 30 minutes, mouse-anti-8-OHdG (OXIS internat., Foster City, Calif., USA) 1:20 in 0.1% PBSA over night at 4° C., biotin labeled horse-anti-mouse (Vector Lab., Burlingame, Calif., USA) 1:500 for 1 hour and with streptavidin-HRPO 1:1000 for 1 hour. Finally, the sections were incubated with $H_2O_2$-diaminebenzidine for 10 minutes. The amount of 8-OHdG positive nuclei was quantified in 4 randomly picked fields per sections with digital image microscopy software (Olympos, Munster, Germany) at 200× magnification.

Cytokine Analysis

The expression of key biomarkers for TNF-alpha, IL-1 b/6/8, ICAM-1 and VCAM-1 were measured by qRT-PCRs. Other relevant analyses included the evaluation of macrophage inflammatory protein (MIP), monocyte chemoattractant protein (MCP)-1, and the phosphorylation of survival pathway proteins (e.g. MAPK, PI3K/Akt).

Total RNA was extracted from infarcted and remote myocardium using Tripure reagent (Roche) according to the manufacturer's instructions, converted into cDNA and subjected to quantitative reverse transcriptase polymerase chain reaction (RT-PCR). TNF alpha, ICAM and VCAM were determined on the mRNA level using primer from Superarray Bioscience Corporation. MCP-1, interleukins and MIP were determined on the protein level (also following Tripure isolation, Roche) using a commercially available cytoflowmix multiplex array (Bender MedSystems). Phosphorylation of Akt and the amount of TLR2 protein upon inhibition with OPN-301 monoclonal antibody will be quantified using Western Blotting.

Chimeric Mice Experiments

Total bone marrow was collected from male TLR2+/+ or TLR2−/− mice by flushing femurs and tibiae with sterile PBS containing 10% FCS, 100 IU/ml penicillin, and 100 ug/ml streptomycin (Invitrogen Corp.). To ensure short-term survival of the recipients, single cell suspension of a syngeneic spleen from a male TLR2+/+ or TLR2−/− mice were obtained by crushing spleens in PBS containing 10% FCS, penicillin, and streptomycin through a 40 μm cell strainer. Male TLR2+/+ and TLR2−/− mice were lethally irradiated with 1 dose of 7 Gy in a human computer tomography scan. After the irradiation, $5\times10^6$ TLR2+/+ or TLR2−/− bone marrow cells and $2\times10^5$ TLR2+/+ or TLR2−/− spleen cells in sterile PBS were injected into the tail vein of recipient irradiated mice. The mice were kept in microisolator cages for 6 weeks to complete engraftment with donor bone marrow, after which myocardial I/R injury is induced and infarct size is determined after 24 hours using TTC staining. Pathophysiological evaluation using above mentioned immunohistochemical analysis could also be performed.

Magnetic Resonance Imaging

Serial assessment of cardiac dimensions and function by high resolution magnetic resonance imaging (MRI, 9.4 T, Bruker, Rheinstetten, Germany) were performed before and 28 days after myocardial ischemia/reperfusion injury. Long axis and short axis images with 1.0 mm interval between the slices were obtained and used to compute end-diastolic volume (EDV), end-systolic volume (ESV), stroke volume (SV) and cardiac output (CO). The ejection fraction (EF) is calculated as 100*(EDV-ESV)/EDV, whereas SV is the absolute difference between EDV and ESV. Cardiac output is the total volumic output within 1 minute, calculated as SV*average heart beats per minute. All MRI data were analyzed using Qmass digital imaging software (Medis, Leiden, the Netherlands).

Results

Data will be analysed and statistical analysis performed by using SPSS software package for Windows v15.0.

(i) MRI Heart Function Post-Infarction

There is no difference at baseline. After 28 days post-infarction, heart function in mice treated with the OPN-301 anti-TLR2 monoclonal antibody is better compared to saline treatment, as end-diastolic and systolic volumes (EDV, ESV) are lower and stroke volume (SV) and ejection fraction (EF) are higher in OPN-301 treated mice. Left ventricular (LV-mass) did not differ between the groups (which is good, because otherwise the enhanced function could be caused by bigger hearts).

However, the sham group was excluded from the analyses, because at baseline they were so different compared to the other groups. It cannot be explained by biological variation. We suspect that an error in the calculations or a different batch/background of mice may be responsible for this. We will check for errors or just order a new batch of C57Bl6J mice for sham operation.

TABLE 7

Group Statistics:

| | Treatment | N | Mean | Std. Deviation | Std. Error Mean |
|---|---|---|---|---|---|
| EDV | Saline | 8 | 68.405 | 9.6401 | 3.4083 |
| | mAb | 8 | 70.049 | 8.7510 | 3.0940 |
| ESV | Saline | 8 | 39.714 | 9.9343 | 3.5123 |
| | mAb | 8 | 38.020 | 7.0095 | 2.4782 |
| SV | Saline | 8 | 28.690 | 1.9269 | .6813 |
| | mAb | 8 | 32.028 | 5.7211 | 2.0227 |
| EF | Saline | 8 | 42.618 | 6.0618 | 2.1432 |
| | mAb | 8 | 45.828 | 6.8354 | 2.4167 |
| LVmass | Saline | 8 | 73.909 | 9.2857 | 3.2830 |
| | mAb | 8 | 69.253 | 6.1860 | 2.1871 |
| EDV28 | Saline | 8 | 76.801 | 9.9619 | 3.5221 |
| | mAb | 8 | 68.158 | 7.0632 | 2.4972 |
| ESV28 | Saline | 8 | 46.360 | 8.7689 | 3.1003 |
| | mAb | 8 | 33.720 | 7.1595 | 2.5312 |
| SV28 | Saline | 8 | 30.440 | 4.6195 | 1.6332 |
| | mAb | 8 | 34.440 | 1.2395 | .4382 |
| EF28 | Saline | 8 | 39.893 | 6.1642 | 2.1794 |
| | mAb | 8 | 51.035 | 5.9714 | 2.1112 |
| LVmass28 | Saline | 8 | 79.123 | 9.9238 | 3.5086 |
| | mAb | 8 | 75.975 | 6.4139 | 2.2676 |

TABLE 8

(Independent Samples Test)

| | | Levene's Test for Equality of Variances | | t-test for Equality of Means | | | | | | |
|---|---|---|---|---|---|---|---|---|---|---|
| | | F | Sig. | t | df | Sig. (2-tailed) | Mean Difference | Std. Error Difference | 95% Confidence Interval of the Difference | |
| | | Lower | Upper | Lower | Upper | Lower | Upper | Lower | Upper | Lower |
| EDV28 | Equal variances assumed | 2.129 | .167 | 2.002 | 14 | .065 | 8.6438 | 4.3175 | −.6165 | 17.9040 |
| | Equal variances not assumed | | | 2.002 | 12.618 | .067 | 8.6438 | 4.3175 | −.7125 | 18.0000 |
| ESV28 | Equal variances assumed | 1.929 | .187 | 3.158 | 14 | .007 | 12.6400 | 4.0024 | 4.0558 | 21.2242 |

TABLE 8-continued (Independent Samples Test)

| | | Levene's Test for Equality of Variances | | t-test for Equality of Means | | | | | 95% Confidence Interval of the Difference | |
|---|---|---|---|---|---|---|---|---|---|---|
| | | F | Sig. | t | df | Sig. (2-tailed) | Mean Difference | Std. Error Difference | Lower | Upper |
| | Equal variances not assumed | | | 3.158 | 13.461 | .007 | 12.6400 | 4.0024 | 4.0234 | 21.2566 |
| SV28 | Equal variances assumed | 5.682 | .032 | −2.365 | 14 | .033 | −4.0000 | 1.6910 | −7.6268 | −.3732 |
| | Equal variances not assumed | | | −2.365 | 8.003 | .046 | −4.0000 | 1.6910 | −7.8992 | −.1008 |
| EF28 | Equal variances assumed | .037 | .851 | −3.672 | 14 | .003 | −11.1425 | 3.0343 | −17.6504 | −4.6346 |
| | Equal variances not assumed | | | −3.672 | 13.986 | .003 | −11.1425 | 3.0343 | −17.6510 | −4.6340 |
| LVmass28 | Equal variances assumed | 1.597 | .227 | .753 | 14 | .464 | 3.1475 | 4.1776 | −5.8126 | 12.1076 |
| | Equal variances not assumed | | | .753 | 11.979 | .466 | 3.1475 | 4.1776 | −5.9565 | 12.2515 |

(ii) Results of Chimeric Mice Experiments

Chimerization was shown to be sucessful. One mouse was excluded in the analyses due to very low infarction. Infarct size reduction was observed in both groups. However mice lacking TLR2 in the blood showed greater reduction. It seems that circulating cells positive for TLR2 are more responsible for the reperfusion injury. The differences in infarct size reduction did not reach statistical difference, due to low sample size.

TABLE 9

| | | N | Mean | Std. Deviation | Std. Error | 95% Confidence Interval for Mean | | Minimum | Maximum |
|---|---|---|---|---|---|---|---|---|---|
| | | | | | | Lower Bound | Upper Bound | | |
| AAR_LV | Saline | 10 | 40.7550 | 11.77170 | 3.72254 | 32.3340 | 49.1760 | 13.93 | 54.21 |
| | TLR2 KO | 10 | 41.4090 | 18.11703 | 5.72911 | 28.4489 | 54.3691 | 21.76 | 75.09 |
| | Blood KO | 7 | 40.2071 | 5.82204 | 2.20052 | 34.8227 | 45.5916 | 32.75 | 49.18 |
| | Organ KO | 6 | 43.6033 | 7.95412 | 3.24726 | 35.2560 | 51.9507 | 37.05 | 59.39 |
| | Total | 33 | 41.3548 | 12.20156 | 2.12402 | 37.0284 | 45.6813 | 13.93 | 75.09 |
| IS_AAR | Saline | 10 | 34.5010 | 10.28226 | 3.25153 | 27.1455 | 41.8565 | 20.99 | 48.26 |
| | TLR2 KO | 10 | 23.0090 | 9.26069 | 2.92849 | 16.3843 | 29.6337 | 11.62 | 38.98 |
| | Blood KO | 7 | 23.6871 | 9.01528 | 3.40746 | 15.3494 | 32.0249 | 11.00 | 39.50 |
| | Organ KO | 6 | 28.2333 | 5.29739 | 2.16265 | 22.6741 | 33.7926 | 21.48 | 36.62 |
| | Total | 33 | 27.5852 | 9.91828 | 1.72655 | 24.0683 | 31.1020 | 11.00 | 48.26 |

TABLE 10

(Multiple Comparisons)

| Dependent Variable | (I) Group | (J) Group | Mean Difference (I-J) | Std. Error | Sig. | 95% Confidence Interval Lower Bound | 95% Confidence Interval Upper Bound |
|---|---|---|---|---|---|---|---|
| AAR_LV | TLR2 KO | Saline | .65400 | 5.70596 | .999 | −13.5676 | 14.8756 |
|  | Blood KO | Saline | −.54786 | 6.28767 | 1.000 | −16.2193 | 15.1236 |
|  | Organ KO | Saline | 2.84833 | 6.58868 | .953 | −13.5734 | 19.2700 |
| ISAAR | TLR2 KO | Saline | −11.49200(*) | 4.02692 | .022 | −21.5287 | −1.4553 |
|  | Blood KO | Saline | −10.81386 | 4.43745 | .056 | −21.8738 | .2461 |
|  | Organ KO | Saline | −6.26767 | 4.64988 | .419 | −17.8571 | 5.3218 |

*The mean difference is significant at the .05 level.
a Dunnett t-tests treat one group as a control, and compare all other groups against it.

The results shown in Table 9 are further illustrated in FIGS. 10 and 11. FIG. 10 shows the area at risk (AAR_LV) as a percentage of the left ventricle. FIG. 11 shows infarct size (IS_AAR) as a percentage of the area at risk.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. A method for the treatment of a reperfusion induced cardiac inflammatory condition, the method comprising the steps of:
    administering a therapeutically effective amount of an antibody or an antigen-binding fragment thereof which is an antagonist of the function of Toll-like Receptor 2 (TLR2), to a subject in need of such treatment.

2. The method as claimed in claim 1, wherein the antibody is selected from the group consisting of a monoclonal antibody, a polyclonal antibody and a synthetic antibody, or an antigen-binding fragment of any of same.

3. The method as claimed in claim 1, wherein the antibody is selected from the group consisting of a human antibody, a humanised antibody, a camelid antibody and an in vitro generated antibody to human TLR2, or an antigen-binding fragment of any of same.

4. The method as claimed in claim 1, wherein the antibody is of an isotype selected from the group consisting of IgG, IgA, IgM and IgE.

5. The method as claimed in claim 1, wherein the antibody or antigen-binding fragment binds to an epitope present on TLR2 with a dissociation constant (Kd) of from about 10-7M to about $10^{-11}$ M.

6. The method as claimed in claim 1, wherein the antibody or antigen-binding fragment binds to an epitope comprising amino acid residues of the extracellular domain of human TLR2.

7. The method as claimed in claim 1, wherein the condition is selected from the group consisting of myocardial ischemia, ischemic heart disease, hypertension myocardial ischemia, congestive heart failure, acute coronary syndrome and myocardial infarction, and arrhythmia.

8. The method as claimed in claim 1, wherein the TLR2 is human TLR2 or murine TLR2.

9. The method as claimed in claim 1, further comprising the step of administering a therapeutically effective amount of at least one secondary therapeutic compound, said secondary therapeutic compound being an immunosuppressant compound.

10. The method as claimed in claim 9, wherein the secondary therapeutic compound is selected from the group consisting of a glucocorticoid, a cytostatic, an anti-metabolite, an anti-CD2 antibody or antigen-binding fragment thereof, an anti-CD20 antibody, an anti-TNF-alpha antibody, cyclosporine, tacrolimus, sirolimus and FTY720.

11. The method as claimed in claim 1, further comprising the step of administering a therapeutically effective amount of at least one secondary therapeutic compound wherein the secondary therapeutic compound is selected from the group consisting of an HMG-CoA reductase inhibitor, a vasodilatory agent, a diuretic, an angiotensin converting enzyme inhibitor, a beta-blocker, an angiotensin II receptor antagonist, a calcium channel blocker, an anticoagulant, an adenosine diphosphate receptor antagonist, ticlopidine, clopidogrel bisulfate, a glycoprotein IIb/IIIa receptor antagonist, bivalirudin, argatroban, heparin, a beta adrenergic receptor agonist, an antithrombolytic agent, an antioxidant, and an alpha blocker.

12. The method as claimed in claim 9, wherein the antibody or antigen-binding fragment is administered simultaneously with the secondary therapeutic compound.

13. The method as claimed in claim 9, wherein the antibody or antigen-binding fragment is administered sequentially to the administration of the secondary therapeutic compound.

14. The method as claimed in claim 1, wherein the antibody or antigen-binding fragment is administered prior to, during, or following the subject undergoing a surgical procedure selected from the group consisting of angioplasty, cardiac bypass surgery, thrombolysis, endarterectomy, heart transplantation and coronary artery bypass grafting (CABG).

15. The method as claimed in claim 1, wherein said method is performed on the subject prior to, during or following the occurrence of an ischemic event in a cell or tissue.

16. The method as claimed in claim 1, wherein the method is performed on the subject during or following the occurrence of reperfusion.

17. The method as claimed in claim 1, wherein the antibody or antigen-binding fragment suppresses the function of TLR2 irrespective of whether TLR2 forms a heterodimer with Toll-like Receptor 1 (TLR1), Toll-like Receptor 4 (TLR4), Toll-like Receptor 6 (TLR6) or Toll-like Receptor 10 (TLR10).

18. The method as claimed in claim 1, wherein the condition results from stroke or hypertrophy.

19. The method as claimed in claim 1, wherein the method is performed on the subject following the occurrence of ischemia.

20. A method for the prophylaxis of a reperfusion induced cardiac inflammatory condition, the method comprising the steps of:
    administering a therapeutically effective amount of an antibody or an antigen-binding fragment thereof which is an antagonist of the function of Toll-like Receptor 2 (TLR2) to a subject in need of such treatment wherein the antibody or antigen-binding fragment is administered prior to, during or following the subject undergoing a surgical procedure selected from the group consisting of angioplasty, cardiac bypass surgery, thrombolysis, endarterectomy, heart transplantation and coronary artery bypass grafting (CABG).

* * * * *

UNITED STATES PATENT AND TRADEMARK OFFICE
CERTIFICATE OF CORRECTION

PATENT NO. : 8,734,788 B2  
APPLICATION NO. : 12/671810  
DATED : May 27, 2014  
INVENTOR(S) : Mark Heffernan et al.

Page 1 of 1

It is certified that error appears in the above-identified patent and that said Letters Patent is hereby corrected as shown below:

In the Claims:

Column 59, claim 7, line 47, delete ", and arrhythmia"

Signed and Sealed this
Twenty-ninth Day of July, 2014

Michelle K. Lee
*Deputy Director of the United States Patent and Trademark Office*

```
                        SEQUENCE LISTING

<160> NUMBER OF SEQ ID NOS: 5

<210> SEQ ID NO 1
<211> LENGTH: 784
<212> TYPE: PRT
<213> ORGANISM: Homo sapiens

<400> SEQUENCE: 1

Met Pro His Thr Leu Trp Met Val Trp Val Leu Gly Val Ile Ile Ser
1               5                   10                  15

Leu Ser Lys Glu Glu Ser Ser Asn Gln Ala Ser Leu Ser Cys Asp Arg
            20                  25                  30

Asn Gly Ile Cys Lys Gly Ser Ser Gly Ser Leu Asn Ser Ile Pro Ser
        35                  40                  45

Gly Leu Thr Glu Ala Val Lys Ser Leu Asp Leu Ser Asn Asn Arg Ile
    50                  55                  60

Thr Tyr Ile Ser Asn Ser Asp Leu Gln Arg Cys Val Asn Leu Gln Ala
65                  70                  75                  80

Leu Val Leu Thr Ser Asn Gly Ile Asn Thr Ile Glu Glu Asp Ser Phe
                85                  90                  95

Ser Ser Leu Gly Ser Leu Glu His Leu Asp Leu Ser Tyr Asn Tyr Leu
            100                 105                 110

Ser Asn Leu Ser Ser Ser Trp Phe Lys Pro Leu Ser Ser Leu Thr Phe
        115                 120                 125

Leu Asn Leu Leu Gly Asn Pro Tyr Lys Thr Leu Gly Glu Thr Ser Leu
    130                 135                 140

Phe Ser His Leu Thr Lys Leu Gln Ile Leu Arg Val Gly Asn Met Asp
145                 150                 155                 160

Thr Phe Thr Lys Ile Gln Arg Lys Asp Phe Ala Gly Leu Thr Phe Leu
                165                 170                 175
```

-continued

```
Glu Glu Leu Glu Ile Asp Ala Ser Asp Leu Gln Ser Tyr Glu Pro Lys
            180                 185                 190

Ser Leu Lys Ser Ile Gln Asn Val Ser His Leu Ile Leu His Met Lys
        195                 200                 205

Gln His Ile Leu Leu Glu Ile Phe Val Asp Val Thr Ser Ser Val
    210                 215                 220

Glu Cys Leu Glu Leu Arg Asp Thr Asp Leu Asp Thr Phe His Phe Ser
225                 230                 235                 240

Glu Leu Ser Thr Gly Glu Thr Asn Ser Leu Ile Lys Lys Phe Thr Phe
                245                 250                 255

Arg Asn Val Lys Ile Thr Asp Glu Ser Leu Phe Gln Val Met Lys Leu
            260                 265                 270

Leu Asn Gln Ile Ser Gly Leu Leu Glu Leu Glu Phe Asp Asp Cys Thr
        275                 280                 285

Leu Asn Gly Val Gly Asn Phe Arg Ala Ser Asp Asn Asp Arg Val Ile
    290                 295                 300

Asp Pro Gly Lys Val Glu Thr Leu Thr Ile Arg Arg Leu His Ile Pro
305                 310                 315                 320

Arg Phe Tyr Leu Phe Tyr Asp Leu Ser Thr Leu Tyr Ser Leu Thr Glu
                325                 330                 335

Arg Val Lys Arg Ile Thr Val Glu Asn Ser Lys Val Phe Leu Val Pro
            340                 345                 350

Cys Leu Leu Ser Gln His Leu Lys Ser Leu Glu Tyr Leu Asp Leu Ser
        355                 360                 365

Glu Asn Leu Met Val Glu Glu Tyr Leu Lys Asn Ser Ala Cys Glu Asp
    370                 375                 380

Ala Trp Pro Ser Leu Gln Thr Leu Ile Leu Arg Gln Asn His Leu Ala
385                 390                 395                 400

Ser Leu Glu Lys Thr Gly Glu Thr Leu Leu Thr Leu Lys Asn Leu Thr
                405                 410                 415

Asn Ile Asp Ile Ser Lys Asn Ser Phe His Ser Met Pro Glu Thr Cys
            420                 425                 430

Gln Trp Pro Glu Lys Met Lys Tyr Leu Asn Leu Ser Ser Thr Arg Ile
        435                 440                 445

His Ser Val Thr Gly Cys Ile Pro Lys Thr Leu Glu Ile Leu Asp Val
    450                 455                 460

Ser Asn Asn Asn Leu Asn Leu Phe Ser Leu Asn Leu Pro Gln Leu Lys
465                 470                 475                 480

Glu Leu Tyr Ile Ser Arg Asn Lys Leu Met Thr Leu Pro Asp Ala Ser
                485                 490                 495

Leu Leu Pro Met Leu Leu Val Leu Lys Ile Ser Arg Asn Ala Ile Thr
            500                 505                 510

Thr Phe Ser Lys Glu Gln Leu Asp Ser Phe His Thr Leu Lys Thr Leu
        515                 520                 525

Glu Ala Gly Gly Asn Asn Phe Ile Cys Ser Cys Glu Phe Leu Ser Phe
    530                 535                 540

Thr Gln Glu Gln Gln Ala Leu Ala Lys Val Leu Ile Asp Trp Pro Ala
545                 550                 555                 560

Asn Tyr Leu Cys Asp Ser Pro Ser His Val Arg Gly Gln Gln Val Gln
                565                 570                 575

Asp Val Arg Leu Ser Val Ser Glu Cys His Arg Thr Ala Leu Val Ser
            580                 585                 590

Gly Met Cys Cys Ala Leu Phe Leu Leu Ile Leu Leu Thr Gly Val Leu
        595                 600                 605
```

```
Cys His Arg Phe His Gly Leu Trp Tyr Met Lys Met Met Trp Ala Trp
    610                 615                 620
Leu Gln Ala Lys Arg Lys Pro Arg Lys Ala Pro Ser Arg Asn Ile Cys
625                 630                 635                 640
Tyr Asp Ala Phe Val Ser Tyr Ser Glu Arg Asp Ala Tyr Trp Val Glu
                645                 650                 655
Asn Leu Met Val Gln Glu Leu Glu Asn Phe Asn Pro Pro Phe Lys Leu
                660                 665                 670
Cys Leu His Lys Arg Asp Phe Ile Pro Gly Lys Trp Ile Ile Asp Asn
            675                 680                 685
Ile Ile Asp Ser Ile Glu Lys Ser His Lys Thr Val Phe Val Leu Ser
    690                 695                 700
Glu Asn Phe Val Lys Ser Glu Trp Cys Lys Tyr Glu Leu Asp Phe Ser
705                 710                 715                 720
His Phe Arg Leu Phe Glu Glu Asn Asn Asp Ala Ala Ile Leu Ile Leu
                725                 730                 735
Leu Glu Pro Ile Glu Lys Lys Ala Ile Pro Gln Arg Phe Cys Lys Leu
                740                 745                 750
Arg Lys Ile Met Asn Thr Lys Thr Tyr Leu Glu Trp Pro Met Asp Glu
            755                 760                 765
Ala Gln Arg Glu Gly Phe Trp Val Asn Leu Arg Ala Ala Ile Lys Ser
    770                 775                 780
```

<210> SEQ ID NO 2
<211> LENGTH: 784
<212> TYPE: PRT
<213> ORGANISM: Mus musculus

<400> SEQUENCE: 2

```
Met Leu Arg Ala Leu Trp Leu Phe Trp Ile Leu Val Ala Ile Thr Val
1                 5                  10                  15
Leu Phe Ser Lys Arg Cys Ser Ala Gln Glu Ser Leu Ser Cys Asp Ala
                20                  25                  30
Ser Gly Val Cys Asp Gly Arg Ser Arg Ser Phe Thr Ser Ile Pro Ser
            35                  40                  45
Gly Leu Thr Ala Ala Met Lys Ser Leu Asp Leu Ser Phe Asn Lys Ile
        50                  55                  60
Thr Tyr Ile Gly His Gly Asp Leu Arg Ala Cys Ala Asn Leu Gln Val
65                  70                  75                  80
Leu Met Leu Lys Ser Ser Arg Ile Asn Thr Ile Glu Gly Asp Ala Phe
                85                  90                  95
Tyr Ser Leu Gly Ser Leu Glu His Leu Asp Leu Ser Asp Asn His Leu
                100                 105                 110
Ser Ser Leu Ser Ser Ser Trp Phe Gly Pro Leu Ser Ser Leu Lys Tyr
            115                 120                 125
Leu Asn Leu Met Gly Asn Pro Tyr Gln Thr Leu Gly Val Thr Ser Leu
        130                 135                 140
Phe Pro Asn Leu Thr Asn Leu Gln Thr Leu Arg Ile Gly Asn Val Glu
145                 150                 155                 160
Thr Phe Ser Glu Ile Arg Arg Ile Asp Phe Ala Gly Leu Thr Ser Leu
                165                 170                 175
Asn Glu Leu Glu Ile Lys Ala Leu Ser Leu Arg Asn Tyr Gln Ser Gln
                180                 185                 190
Ser Leu Lys Ser Ile Arg Asp Ile His His Leu Thr Leu His Leu Ser
            195                 200                 205
```

-continued

```
Glu Ser Ala Phe Leu Leu Glu Ile Phe Ala Asp Ile Leu Ser Ser Val
    210                 215                 220
Arg Tyr Leu Glu Leu Arg Asp Thr Asn Leu Ala Arg Phe Gln Phe Ser
225                 230                 235                 240
Pro Leu Pro Val Asp Glu Val Ser Ser Pro Met Lys Lys Leu Ala Phe
                245                 250                 255
Arg Gly Ser Val Leu Thr Asp Glu Ser Phe Asn Glu Leu Leu Lys Leu
                260                 265                 270
Leu Arg Tyr Ile Leu Glu Leu Ser Glu Val Glu Phe Asp Asp Cys Thr
            275                 280                 285
Leu Asn Gly Leu Gly Asp Phe Asn Pro Ser Glu Ser Asp Val Val Ser
    290                 295                 300
Glu Leu Gly Lys Val Thr Val Thr Ile Arg Arg Leu His Ile Pro
305                 310                 315                 320
Gln Phe Tyr Leu Phe Tyr Asp Leu Ser Thr Val Tyr Ser Leu Leu Glu
                325                 330                 335
Lys Val Lys Arg Ile Thr Val Glu Asn Ser Lys Val Phe Leu Val Pro
                340                 345                 350
Cys Ser Phe Ser Gln His Leu Lys Ser Leu Glu Phe Leu Asp Leu Ser
    355                 360                 365
Glu Asn Leu Met Val Glu Glu Tyr Leu Lys Asn Ser Ala Cys Lys Gly
370                 375                 380
Ala Trp Pro Ser Leu Gln Thr Leu Val Leu Ser Gln Asn His Leu Arg
385                 390                 395                 400
Ser Met Gln Lys Thr Gly Glu Ile Leu Leu Thr Leu Lys Asn Leu Thr
                405                 410                 415
Ser Leu Asp Ile Ser Arg Asn Thr Phe His Pro Met Pro Asp Ser Cys
            420                 425                 430
Gln Trp Pro Glu Lys Met Arg Phe Leu Asn Leu Ser Ser Thr Gly Ile
            435                 440                 445
Arg Val Val Lys Thr Cys Ile Pro Gln Thr Leu Glu Val Leu Asp Val
    450                 455                 460
Ser Asn Asn Asn Leu Asp Ser Phe Ser Leu Phe Leu Pro Arg Leu Gln
465                 470                 475                 480
Glu Leu Tyr Ile Ser Arg Asn Lys Leu Lys Thr Leu Pro Asp Ala Ser
                485                 490                 495
Leu Phe Pro Val Leu Leu Val Met Lys Ile Arg Glu Asn Ala Val Ser
                500                 505                 510
Thr Phe Ser Lys Asp Gln Leu Gly Ser Phe Pro Lys Leu Glu Thr Leu
            515                 520                 525
Glu Ala Gly Asp Asn His Phe Val Cys Ser Cys Glu Leu Leu Ser Phe
    530                 535                 540
Thr Met Glu Thr Pro Ala Leu Ala Gln Ile Leu Val Asp Trp Pro Asp
545                 550                 555                 560
Ser Tyr Leu Cys Asp Ser Pro Arg Leu His Gly His Arg Leu Gln
                565                 570                 575
Asp Ala Arg Pro Ser Val Leu Glu Cys His Gln Ala Ala Leu Val Ser
                580                 585                 590
Gly Val Cys Cys Ala Leu Leu Leu Ile Leu Leu Val Gly Ala Leu
            595                 600                 605
Cys His His Phe His Gly Leu Trp Tyr Leu Arg Met Met Trp Ala Trp
    610                 615                 620
Leu Gln Ala Lys Arg Lys Pro Lys Lys Ala Pro Cys Arg Asp Val Cys
```

```
              625                 630                 635                 640
Tyr Asp Ala Phe Val Ser Tyr Ser Glu Gln Asp Ser His Trp Val Glu
                    645                 650                 655
Asn Leu Met Val Gln Gln Leu Glu Asn Ser Asp Pro Pro Phe Lys Leu
                660                 665                 670
Cys Leu His Lys Arg Asp Phe Val Pro Gly Lys Trp Ile Ile Asp Asn
                675                 680                 685
Ile Ile Asp Ser Ile Glu Lys Ser His Lys Thr Val Phe Val Leu Ser
            690                 695                 700
Glu Asn Phe Val Arg Ser Glu Trp Cys Lys Tyr Glu Leu Asp Phe Ser
705                 710                 715                 720
His Phe Arg Leu Phe Asp Glu Asn Asn Asp Ala Ala Ile Leu Val Leu
                    725                 730                 735
Leu Glu Pro Ile Glu Arg Lys Ala Ile Pro Gln Arg Phe Cys Lys Leu
                740                 745                 750
Arg Lys Ile Met Asn Thr Lys Thr Tyr Leu Glu Trp Pro Leu Asp Glu
                755                 760                 765
Gly Gln Gln Glu Val Phe Trp Val Asn Leu Arg Thr Ala Ile Lys Ser
            770                 775                 780

<210> SEQ ID NO 3
<211> LENGTH: 586
<212> TYPE: PRT
<213> ORGANISM: Homo sapiens

<400> SEQUENCE: 3

Met Pro His Thr Leu Trp Met Val Trp Val Leu Gly Val Ile Ile Ser
1               5                   10                  15
Leu Ser Lys Glu Glu Ser Ser Asn Gln Ala Ser Leu Ser Cys Asp Arg
                20                  25                  30
Asn Gly Ile Cys Lys Gly Ser Ser Gly Ser Leu Asn Ser Ile Pro Ser
            35                  40                  45
Gly Leu Thr Glu Ala Val Lys Ser Leu Asp Leu Ser Asn Asn Arg Ile
        50                  55                  60
Thr Tyr Ile Ser Asn Ser Asp Leu Gln Arg Cys Val Asn Leu Gln Ala
65                  70                  75                  80
Leu Val Leu Thr Ser Asn Gly Ile Asn Thr Ile Glu Glu Asp Ser Phe
                85                  90                  95
Ser Ser Leu Gly Ser Leu Glu His Leu Asp Leu Ser Tyr Asn Tyr Leu
                100                 105                 110
Ser Asn Leu Ser Ser Ser Trp Phe Lys Pro Leu Ser Ser Leu Thr Phe
            115                 120                 125
Leu Asn Leu Leu Gly Asn Pro Tyr Lys Thr Leu Gly Glu Thr Ser Leu
        130                 135                 140
Phe Ser His Leu Thr Lys Leu Gln Ile Leu Arg Val Gly Asn Met Asp
145                 150                 155                 160
Thr Phe Thr Lys Ile Gln Arg Lys Asp Phe Ala Gly Leu Thr Phe Leu
                165                 170                 175
Glu Glu Leu Glu Ile Asp Ala Ser Asp Leu Gln Ser Tyr Glu Pro Lys
                180                 185                 190
Ser Leu Lys Ser Ile Gln Asn Val Ser His Leu Ile Leu His Met Lys
            195                 200                 205
Gln His Ile Leu Leu Leu Glu Ile Phe Val Asp Val Thr Ser Ser Val
        210                 215                 220
Glu Cys Leu Glu Leu Arg Asp Thr Asp Leu Asp Thr Phe His Phe Ser
```

```
                225                 230                 235                 240
Glu Leu Ser Thr Gly Glu Thr Asn Ser Leu Ile Lys Lys Phe Thr Phe
                    245                 250                 255

Arg Asn Val Lys Ile Thr Asp Glu Ser Leu Phe Gln Val Met Lys Leu
                260                 265                 270

Leu Asn Gln Ile Ser Gly Leu Leu Glu Leu Glu Phe Asp Asp Cys Thr
            275                 280                 285

Leu Asn Gly Val Gly Asn Phe Arg Ala Ser Asp Asn Asp Arg Val Ile
        290                 295                 300

Asp Pro Gly Lys Val Glu Thr Leu Thr Ile Arg Arg Leu His Ile Pro
305                 310                 315                 320

Arg Phe Tyr Leu Phe Tyr Asp Leu Ser Thr Leu Tyr Ser Leu Thr Glu
                325                 330                 335

Arg Val Lys Arg Ile Thr Val Glu Asn Ser Lys Val Phe Leu Val Pro
                340                 345                 350

Cys Leu Leu Ser Gln His Leu Lys Ser Leu Glu Tyr Leu Asp Leu Ser
            355                 360                 365

Glu Asn Leu Met Val Glu Glu Tyr Leu Lys Asn Ser Ala Cys Glu Asp
        370                 375                 380

Ala Trp Pro Ser Leu Gln Thr Leu Ile Leu Arg Gln Asn His Leu Ala
385                 390                 395                 400

Ser Leu Glu Lys Thr Gly Glu Thr Leu Leu Thr Leu Lys Asn Leu Thr
                405                 410                 415

Asn Ile Asp Ile Ser Lys Asn Ser Phe His Ser Met Pro Glu Thr Cys
                420                 425                 430

Gln Trp Pro Glu Lys Met Lys Tyr Leu Asn Leu Ser Ser Thr Arg Ile
            435                 440                 445

His Ser Val Thr Gly Cys Ile Pro Lys Thr Leu Glu Ile Leu Asp Val
        450                 455                 460

Ser Asn Asn Asn Leu Asn Leu Phe Ser Leu Asn Leu Pro Gln Leu Lys
465                 470                 475                 480

Glu Leu Tyr Ile Ser Arg Asn Lys Leu Met Thr Leu Pro Asp Ala Ser
                485                 490                 495

Leu Leu Pro Met Leu Leu Val Leu Lys Ile Ser Arg Asn Ala Ile Thr
                500                 505                 510

Thr Phe Ser Lys Glu Gln Leu Asp Ser Phe His Thr Leu Lys Thr Leu
            515                 520                 525

Glu Ala Gly Gly Asn Asn Phe Ile Cys Ser Cys Glu Phe Leu Ser Phe
        530                 535                 540

Thr Gln Glu Gln Gln Ala Leu Ala Lys Val Leu Ile Asp Trp Pro Ala
545                 550                 555                 560

Asn Tyr Leu Cys Asp Ser Pro Ser His Val Arg Gly Gln Gln Val Gln
                565                 570                 575

Asp Val Arg Leu Ser Val Ser Glu Cys His
            580                 585

<210> SEQ ID NO 4
<211> LENGTH: 21
<212> TYPE: PRT
<213> ORGANISM: Homo sapiens

<400> SEQUENCE: 4

Lys Glu Glu Ser Ser Asn Gln Ala Ser Leu Ser Cys Asp Arg Asn Gly
1               5                   10                  15

Ile Cys Lys Gly Ser
```

```
                        20

<210> SEQ ID NO 5
<211> LENGTH: 13
<212> TYPE: PRT
<213> ORGANISM: Homo sapiens

<400> SEQUENCE: 5

Cys Ser Cys Glu Phe Leu Ser Phe Thr Gln Glu Gln Gln
1               5                   10
```